(12) United States Patent
Leung et al.

(10) Patent No.: US 9,382,525 B2
(45) Date of Patent: Jul. 5, 2016

(54) SITE-DIRECTED PEGYLATION OF ARGINASES AND THE USE THEREOF AS ANTI-CANCER AND ANTI-VIRAL AGENTS

(71) Applicant: The Hong Kong Polytechnic University, Hong Kong (HK)

(72) Inventors: Yun Chung Leung, Hong Kong (HK); Wai-hung Lo, Hong Kong (HK)

(73) Assignee: The Hong Kong Polytechnic University, Hung Hom, Kowloon (HK)

(*) Notice: Subject to any disclaimer, the term of this patent is extended or adjusted under 35 U.S.C. 154(b) by 150 days.

(21) Appl. No.: 13/945,938

(22) Filed: Jul. 19, 2013

(65) Prior Publication Data

US 2014/0023628 A1    Jan. 23, 2014

Related U.S. Application Data

(63) Continuation-in-part of application No. 12/732,188, filed on Mar. 26, 2010, now Pat. No. 8,507,245.

(51) Int. Cl.
| | | |
|---|---|---|
| *C12N 9/78* | (2006.01) | |
| *A61K 47/48* | (2006.01) | |
| *A61K 38/00* | (2006.01) | |

(52) U.S. Cl.
CPC ............ *C12N 9/78* (2013.01); *A61K 47/48215* (2013.01); *C12Y 305/03001* (2013.01); *A61K 38/00* (2013.01)

(58) Field of Classification Search
CPC ... A61K 38/00; A61K 47/48215; C12N 9/78; C12Y 305/03001
See application file for complete search history.

(56) References Cited

U.S. PATENT DOCUMENTS

| 2010/0247508 A1* | 9/2010 | Leung et al. .................. 424/94.6 |
| 2011/0300109 A1* | 12/2011 | Tepic et al. ................... 424/93.4 |

FOREIGN PATENT DOCUMENTS

| WO | WO 03/063780 | * | 8/2003 |
| WO | WO 2004/022004 | * | 3/2004 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Cheng et al., Cancer Research 67(1):309-317, 2007.*
Kepka-Lenhart et al., GenBank accession No. Q95JC8, 2004.*
Stone et al., ACS Chemical Biology 5(3):333-342, published online Jan. 5, 2010.*
Stone et al., Journal of Controlled Release 158:171-179, 2012.*

* cited by examiner

*Primary Examiner* — Delia Ramirez
(74) *Attorney, Agent, or Firm* — Ella Cheong Hong Kong; Sam T. Yip

(57) ABSTRACT

The present invention provides a site-specific pegylated arginase conjugate and method for producing thereof. The site-specific pegylated arginase is homogeneous in molecular weight and shows therapeutic effect for treating cancers and viral infections. The method for producing the arginase conjugate comprises genetically modifying the gene encoding an arginase so that the PEG moiety can be attached to the enzyme at a predetermined, specific intended sites. This is achieved by removing the PEG-attaching amino acid residue(s) at undesirable site(s) while keeping or adding cysteine(s) at the desirable site(s) of the enzyme. Two exemplary embodiments of the pegylated arginase conjugate are directed to human arginase I (HAI) where a polyethylene glycol (PEG) moiety is site-specific covalently bonded to $Cys^{45}$ of the enzyme and *Bacillus caldovelox* arginase (BCA) where a polyethylene glycol (PEG) moiety is site-specific covalently bonded to $Cys^{161}$ of the enzyme.

5 Claims, 50 Drawing Sheets
(23 of 50 Drawing Sheet(s) Filed in Color)

```
ATGAGCGCCAAGTCCAGAACCATAGGGATTATTGGAGCTCCTTTCTCAAAGGGACAGCCA 60
CGAGGAGGGGTGGAAGAAGGCCCTACAGTATTGAGAAAGGCTGGTCTGCTTGAGAAACTT 120
AAAGAACAAGAGTGTGATGTGAAGGATTATGGGGACCTGCCCTTTGCTGACATCCCTAAT 180
GACAGTCCCTTTCAAATTGTGAAGAATCCAAGGTCTGTGGGAAAAGCAAGCGAGCAGCTG 240
GCTGGCAAGGTGGCAGAAGTCAAGAAGAACGGAAGAATCAGCCTGGTGCTGGGCGGAGAC 300
CACAGTTTGGCAATTGGAAGCATCTCTGGCCATGCCAGGGTCCACCCTGATCTTGGAGTC 360
ATCTGGGTGGATGCTCACACTGATATCAACACTCCACTGACAACCACAAGTGGAAACTTG 420
CATGGACAACCTGTATCTTTCCTCCTGAAGGAACTAAAAGGAAAGATTCCCGATGTGCCA 480
GGATTCTCCTGGGTGACTCCCTGTATATCTGCCAAGGATATTGTGTATATTGGCTTGAGA 540
GACGTGGACCCTGGGGAACACTACATTTTGAAAACTCTAGGCATTAAATACTTTTCAATG 600
ACTGAAGTGGACAGACTAGGAATTGGCAAGGTGATGGAAGAAACACTCAGCTATCTACTA 660
GGAAGAAAGAAAGGCCAATTCATCTAAGTTTTGATGTTGACGGACTGGACCCATCTTTC 720
ACACCAGCTACTGGCACACCAGTCGTGGGAGGTCTGACATACAGAGAAGGTCTCTACATC 780
ACAGAAGAAATCTACAAAACAGGGCTACTCTCAGGATTAGATATAATGGAAGTGAACCCA 840
TCCCTGGGGAAGACACCAGAAGAAGTAACTCGAACAGTGAACACAGCAGTTGCAATAACC 900
TTGGCTTGTTTCGGACTTGCTCGGGAGGGTAATCACAAGCCTATTGACTACCTTAACCCA 960
CCTAAGTAA 969
```

FIG. 1A

```
ATGAGCGCCAAGTCCAGAACCATAGGGATTATTGGAGCTCCTTTCTCAAAGGGACAGCCA  60
CGAGGAGGGGTGGAAGAAGGCCCTACAGTATTGAGAAAGGCTGGTCTGCTTGAGAAACTT 120
AAAGAACAAGAGTGTGATGTGAAGGATTATGGGGACCTGCCCTTTGCTGACATCCCTAAT 180
GACAGTCCCTTTCAAATTGTGAAGAATCCAAGGTCTGTGGGAAAAGCAAGCGAGCAGCTG 240
GCTGGCAAGGTGGCAGAAGTCAAGAAGAACGGAAGAATCAGCCTGGTGCTGGGCGGAGAC 300
CACAGTTTGGCAATTGGAAGCATCTCTGGCCATGCCAGGGTCCACCCTGATCTTGGAGTC 360
ATCTGGGTGGATGCTCACACTGATATCAACACTCCACTGACAACCACAAGTGGAAACTTG 420
CATGGACAACCTGTATCTTTCCTCCTGAAGGAACTAAAAGGAAAGATTCCCGATGTGCCA 480
GGATTCTCCTGGGTGACTCCCTATATCTGCCAAGGATATTGTGTATATTGGCTTGAGA 540
GACGTGGACCCTGGGGAACACTACATTTTGAAAACTCTAGGCATTAAATACTTTTCAATG 600
ACTGAAGTGGACAGACTAGGAATTGGCAAGGTGATGGAAGAAACACTCAGCTATCTACTA 660
GGAAGAAAGAAAAGGCCAATTCATCTAAGTTTTGATGTTGACGGACTGGACCCATCTTTC 720
ACACCAGCTACTGGCACACCAGTCGTGGGAGGTCTGACATACAGAGAAGGTCTCTACATC 780
ACAGAAGAAATCTACAAAACAGGGCTACTCTCAGGATTAGATATAATGGAAGTGAACCCA 840
TCCCTGGGGAAGACACCAGAAGAAGTAACTCGAACAGTGAACACAGCAGTTGCAATAACC 900
TTGGCTTTTTCGGACTTGCTCGGGAGGGTAATCACAAGCCTATTGACTACCTTAACCCA 960
CCTAAGTAA 969
```

FIG. 1B

```
ATGAAGCCAATTTCAATTATCGGGGTTCCGATGGATTTAGGGCAGACACG      50
CCGCGGCGTTGATATGGGGCCGAGCGCAATGCGTTATGCAGGCGTCATCG     100
AACGTCTGGAACGTCTTCATTACGATATTGAAGATTTGGGAGATATTCCG     150
ATTGGAAAAGCAGAGCGGTTGCACGAGCAAGGAGATTCACGGTTGCGCAA     200
TTTGAAAGCGGTTGCGGAAGCGAACGAGAAACTTGCGGCGGCGGTTGACC     250
AAGTCGTTCAGCGGGGCGATTTCCGCTTGTGTTGGGCGGCGACCATAGC     300
ATCGCCATTGGCACGCTCGCCGGGGTGGCGAAACATTATGAGCGGCTTGG     350
AGTGATCTGGTATGACGCGCATGGCGACGTCAACACCGCGGAAACGTCGC     400
CGTCTGGAAACATTCATGGCATGCCGCTGGCGGCGAGCCTCGGGTTTGGC     450
CATCCGGCGCTGACGCAAATCGGCGGATACAGCCCCAAAATCAAGCCGGA     500
ACATGTCGTGTTGATCGGCGTCCGTTCCCTTGATGAAGGGGAGAAGAAGT     550
TTATTCGCGAAAAAGGAATCAAAATTTACACGATGCATGAGGTTGATCGG     600
CTCGGAATGACAAGGGTGATGGAAGAAACGATCGCCTATTTAAAAGAACG     650
AACGGATGGCGTTCATTTGTCGCTTGACTTGGATGGCCTTGACCCAAGCG     700
ACGCACCGGGAGTCGGAACGCCTGTCATTGGAGGATTGACATACCGCGAA     750
AGCCATTTGGCGATGGAGATGCTGGCCGAGGCACAAATCATCACTTCAGC     800
GGAATTTGTCGAAGTGAACCCGATCTTGGATGAGCGGAACAAAACAGCAT     850
CAGTGGCTGTAGCGCTGATGGGGTCGTTGTTTGGTGAAAAACTCATGTAA     900
```

FIG. 1C

```
ATGAAGCCAATTTCAATTATCGGGGTTCCGATGGATTTAGGGCAGACACG      50
CCGCGGCGTTGATATGGGGCCGAGCGCAATGCGTTATGCAGGCGTCATCG     100
AACGTCTGGAACGTCTTCATTACGATATTGAAGATTTGGGAGATATTCCG     150
ATTGGAAAAGCAGAGCGGTTGCACGAGCAAGGAGATTCACGGTTGCGCAA     200
TTTGAAAGCGGTTGCGGAAGCGAACGAGAAACTTGCGGCGGCGGTTGACC     250
AAGTCGTTCAGCGGGGCGATTTCCGCTTGTGTTGGGCGGCGACCATAGC      300
ATCGCCATTGGCACGCTCGCCGGGGTGGCGAAACATTATGAGCGGCTTGG     350
AGTGATCTGGTATGACGCGCATGGCGACGTCAACACCGCGGAAACGTCGC     400
CGTCTGGAAACATTCATGGCATGCCGCTGGCGGCGAGCCTCGGGTTTGGC     450
CATCCGGCGCTGACGCAAATCGGCGGATAC GCCCCAAAATCAAGCCGGA     500
ACATGTCGTGTTGATCGGCGTCCGTTCCCTTGATGAAGGGGAGAAGAAGT     550
TTATTCGCGAAAAAGGAATCAAAATTTACACGATGCATGAGGTTGATCGG     600
CTCGGAATGACAAGGGTGATGGAAGAAACGATCGCCTATTTAAAAGAACG     650
AACGGATGGCGTTCATTTGTCGCTTGACTTGGATGGCCTTGACCCAAGCG     700
ACGCACCGGGAGTCGGAACGCCTGTCATTGGAGGATTGACATACCGCGAA     750
AGCCATTTGGCGATGGAGATGCTGGCCGAGGCACAAATCATCACTTCAGC     800
GGAATTTGTCGAAGTGAACCCGATCTTGGATGAGCGGAACAAAACAGCAT     850
CAGTGGCTGTAGCGCTGATGGGGTCGTTGTTTGGTGAAAAACTCATGCAT     900
CACCATCACCATCACTAA      918
```

FIG. 1D

```
MSAKSRTIGIIGAPFSKGQPRGGVEEGPTVLRKAGLLEKLKEQE DVKDYGDLPFADIPN  60
DSPFQIVKNPRSVGKASEQLAGKVAEVKKNGRISLVLGGDHSLAIGSISGHARVHPDLGV 120
IWVDAHTDINTPLTTTSGNLHGQPVSFLLKELKGKIPDVPGFSWVTP ISAKDIVYIGLR 180
DVDPGEHYILKTLGIKYFSMTEVDRLGIGKVMEETLSYLLGRKKRPIHLSFDVDGLDPSF 240
TPATGTPVVGGLTYREGLYITEEIYKTGLLSGLDIMEVNPSLGKTPEEVTRTVNTAVAIT 300
LA FGLAREGNHKPIDYLNPPK 322
```

FIG. 2A

```
MSAKSRTIGIIGAPFSKGQPRGGVEEGPTVLRKAGLLEKLKEQE DVKDYGDLPFADIPN  60
DSPFQIVKNPRSVGKASEQLAGKVAEVKKNGRISLVLGGDHSLAIGSISGHARVHPDLGV 120
IWVDAHTDINTPLTTTSGNLHGQPVSFLLKELKGKIPDVPGFSWVTP ISAKDIVYIGLR 180
DVDPGEHYILKTLGIKYFSMTEVDRLGIGKVMEETLSYLLGRKKRPIHLSFDVDGLDPSF 240
TPATGTPVVGGLTYREGLYITEEIYKTGLLSGLDIMEVNPSLGKTPEEVTRTVNTAVAIT 300
LA FGLAREGNHKPIDYLNPPK 322
```

FIG. 2B

MKPISIIGVPMDLGQTRRGVDMGPSAMRYAGVIERLERLHYDIEDLGDIP    50
IGKAERLHEQGDSRLRNLKAVAEANEKLAAAVDQVVQRGRFPLVLGGDHS   100
IAIGTLAGVAKHYERLGVIWYDAHGDVNTAETSPSGNIHGMPLAASLGFG   150
HPALTQIGGYSPKIKPEHVVLIGVRSLDEGEKKFIREKGIKIYTMHEVDR   200
LGMTRVMEETIAYLKERTDGVHLSLDLDGLDPSDAPGVGTPVIGGLTYRE   250
SHLAMEMLAEAQIITSAEFVEVNPILDERNKTASVAVALMGSLFGEKLM    299

FIG. 2C

MKPISIIGVPMDLGQTRRGVDMGPSAMRYAGVIERLERLHYDIEDLGDIP    50
IGKAERLHEQGDSRLRNLKAVAEANEKLAAAVDQVVQRGRFPLVLGGDHS   100
IAIGTLAGVAKHYERLGVIWYDAHGDVNTAETSPSGNIHGMPLAASLGFG   150
HPALTQIGGY PKIKPEHVVLIGVRSLDEGEKKFIREKGIKIYTMHEVDR   200
LGMTRVMEETIAYLKERTDGVHLSLDLDGLDPSDAPGVGTPVIGGLTYRE   250
SHLAMEMLAEAQIITSAEFVEVNPILDERNKTASVAVALMGSLFGEKLM   300
 305

FIG. 2D

```
atgagcgccaagtccagaaccatagggattattggagctcctttctcaaagggacagcca
 M  S  A  K  S  R  T  I  G  I  I  G  A  P  F  S  K  G  Q  P
cgaggaggggtggaagaaggccctacagtattgagaaaggctggtctgcttgagaaactt
 R  G  G  V  E  E  G  P  T  V  L  R  K  A  G  L  L  E  K  L
aaagaacaagagtgtgatgtgaaggattatggggacctgccctttgctgacatccctaat
 K  E  Q  E  C  D  V  K  D  Y  G  D  L  P  F  A  D  I  P  N
gacagtcccttcaaattgtgaagaatccaaggtctgtgggaaaagcaagcgagcagctg
 D  S  P  F  Q  I  V  K  N  P  R  S  V  G  K  A  S  E  Q  L
gctggcaaggtggcagaagtcaagaagaacggaagaatcagcctggtgctgggcggagac
 A  G  K  V  A  E  V  K  K  N  G  R  I  S  L  V  L  G  G  D
cacagtttggcaattggaagcatctctggccatgccagggtccaccctgatcttggagtc
 H  S  L  A  I  G  S  I  S  G  H  A  R  V  H  P  D  L  G  V
atctgggtggatgctcacactgatatcaacactccactgacaaccacaagtggaaacttg
 I  W  V  D  A  H  T  D  I  N  T  P  L  T  T  T  S  G  N  L
catggacaacctgtatctttcctcctgaaggaactaaaaggaaagattcccgatgtgcca
 H  G  Q  P  V  S  F  L  L  K  E  L  K  G  I  P  D  V  P
ggattctctgggtgactccctctatatctgccaaggatattgtgtatattggcttgaga
 G  F  S  W  V  T  P  S  I  S  A  K  D  I  V  Y  I  G  L  R
gacgtggaccctggggaacactacattttgaaaactctaggcattaaatacttttcaatg
 D  V  D  P  G  E  H  Y  I  L  K  T  L  G  I  K  Y  F  S  M
actgaagtggacagactaggaattggcaaggtgatggaagaaacactcagctatctacta
 T  E  V  D  R  L  G  I  G  K  V  M  E  E  T  L  S  Y  L  L
ggaagaaagaaaaggccaattcatctaagttttgatgttgacggactggacccatctttc
 G  R  K  K  R  P  I  H  L  S  F  D  V  D  G  L  D  P  S  F
acaccagctactggcacaccagtcgtgggaggtctgacatacagagaaggtctctacatc
 T  P  A  T  G  T  P  V  V  G  G  L  T  Y  R  E  G  L  Y  I
acagaagaaatctacaaaacagggctactctcaggattagatataatggaagtgaaccca
 T  E  E  I  Y  K  T  G  L  L  S  G  L  D  I  M  E  V  N  P
tccctggggaagacaccagaagaagtaactcgaacagtgaacacagcagttgcaataacc
 S  L  G  K  T  P  E  E  V  T  R  T  V  N  T  A  V  A  I  T
ttggcttctttcggacttgctcggggagggtaatcacaagcctattgactaccttaaccca
 L  A  S  F  G  L  A  R  E  G  N  H  K  P  I  D  Y  L  N  P
cctaagtaa
 P  K  -
```

FIG. 3A

```
atgcatcaccatcaccatcacatgagcgccaagtccagaaccatagggattattggagct
 M  H  H  H  H  H  H  M  S  A  K  S  R  T  I  G  I  I  G  A
cctttctcaaagggacagccacgaggaggggtggaagaaggccctacagtattgagaaag
 P  F  S  K  G  Q  P  R  G  G  V  E  E  G  P  T  V  L  R  K
gctggtctgcttgagaaacttaaagaacaagagtgtgatgtgaaggattatggggacctg
 A  G  L  L  E  K  L  K  E  Q  E  C  D  V  K  D  Y  G  D  L
ccctttgctgacatccctaatgacagtcccttcaaattgtgaagaatccaaggtctgtg
 P  F  A  D  I  P  N  D  S  P  F  Q  I  V  K  N  P  R  S  V
ggaaaagcaagcgagcagctggctggcaaggtggcagaagtcaagaagaacggaagaatc
 G  K  A  S  E  Q  L  A  G  K  V  A  E  V  K  K  N  G  R  I
agcctggtgctgggcggagaccacagtttggcaattggaagcatctctggccatgccagg
 S  L  V  L  G  G  D  H  S  L  A  I  G  S  I  S  G  H  A  R
gtccaccctgatcttggagtcatctgggtggatgctcacactgatatcaacactccactg
 V  H  P  D  L  G  V  I  W  V  D  A  H  T  D  I  N  T  P  L
acaaccacaagtggaaacttgcatggacaacctgtatctttcctcctgaaggaactaaaa
 T  T  T  S  G  N  L  H  G  Q  P  V  S  F  L  L  K  E  L  K
ggaaagattcccgatgtgccaggattctcctgggtgactccctctatatctgccaaggat
 G  K  I  P  D  V  P  G  F  S  W  V  T  P  S  I  S  A  K  D
attgtgtatattggcttgagagacgtggaccctggggaacactacattttgaaaactcta
 I  V  Y  I  G  L  R  D  V  D  P  G  E  H  Y  I  L  K  T  L
ggcattaaatacttttcaatgactgaagtggacagactaggaattggcaaggtgatggaa
 G  I  K  Y  F  S  M  T  E  V  D  R  L  G  I  G  K  V  M  E
gaaacactcagctatctactaggaagaaagaaaaggccaattcatctaagttttgatgtt
 E  T  L  S  Y  L  L  G  R  K  K  R  P  I  H  L  S  F  D  V
gacggactggacccatctttcacaccagctactggcacaccagtcgtgggaggtctgaca
 D  G  L  D  P  S  F  T  P  A  T  G  T  P  V  V  G  L  T
tacagagaaggtctctacatcacagaagaaatctacaaaacagggctactctcaggatta
 Y  R  E  G  L  Y  I  T  E  E  I  Y  K  T  G  L  L  S  G  L
gatataatggaagtgaacccatccctggggaagacaccagaagaagtaactcgaacagtg
 D  I  M  E  V  N  P  S  L  G  K  T  P  E  E  V  T  R  T  V
aacacagcagttgcaataaccttggcttctttcggacttgctcgggagggtaatcacaag
 N  T  A  V  A  I  T  L  A  S  F  G  L  A  R  E  G  N  H  K
cctattgactaccttaacccacctaagtaa
 P  I  D  Y  L  N  P  P  K  -
```

FIG. 3B

```
atgaagccaatttcaattatcggggttccgatggatttagggcagacacgccgcggcgtt
 M  K  P  I  S  I  I  G  V  P  M  D  L  G  Q  T  R  R  G  V
gatatggggccgagcgcaatgcgttatgcaggcgtcatcgaacgtctggaacgtcttcat
 D  M  G  P  S  A  M  R  Y  A  G  V  I  E  R  L  E  R  L  H
tacgatattgaagatttggagatattccgattggaaaagcagagcggttgcacgagcaa
 Y  D  I  E  D  L  G  D  I  P  I  G  K  A  E  R  L  H  E  Q
ggagattcacggttgcgcaatttgaaagcggttgcggaagcgaacgagaaacttgcggcg
 G  D  S  R  L  R  N  L  K  A  V  A  E  A  N  E  K  L  A  A
gcggttgaccaagtcgttcagcgggggcgatttccgcttgtgttgggcggcgaccatagc
 A  V  D  Q  V  V  Q  R  G  R  F  P  L  V  L  G  G  D  H  S
atcgccattggcacgctcgccggggtggcgaaacattatgagcggcttggagtgatctgg
 I  A  I  G  T  L  A  G  V  A  K  H  Y  E  R  L  G  V  I  W
tatgacgcgcatggcgacgtcaacaccgcggaaacgtcgccgtctggaaacattcatggc
 Y  D  A  H  G  D  V  N  T  A  E  T  S  P  S  G  N  I  H  G
atgccgctggcggcgagcctcgggtttggccatccggcgctgacgcaaatcggcggatac
 M  P  L  A  A  S  L  G  F  G  H  P  A  L  T  Q  I  G  G  Y
tgccccaaaatcaagccggaacatgtcgtgttgatcggcgtccgttcccttgatgaaggg
 C  P  K  I  K  P  E  H  V  V  L  I  G  V  R  S  L  D  E  G
gagaagaagtttattcgcgaaaaaggaatcaaaatttacacgatgcatgaggttgatcgg
 E  K  K  F  I  R  E  K  G  I  K  I  Y  T  M  H  E  V  D  R
ctcggaatgacaagggtgatggaagaaacgatcgcctatttaaaagaacgaacggatggc
 L  G  M  T  R  V  M  E  E  T  I  A  Y  L  K  E  R  T  D  G
gttcatttgtcgcttgacttggatggccttgacccaagcgacgcaccgggagtcggaacg
 V  H  L  S  L  D  L  D  G  L  D  P  S  D  A  P  G  V  G  T
cctgtcattggaggattgacataccgcgaaagccatttggcgatggagatgctggccgag
 P  V  I  G  G  L  T  Y  R  E  S  H  L  A  M  E  M  L  A  E
gcacaaatcatcacttcagcggaatttgtcgaagtgaacccgatcttggatgagcggaac
 A  Q  I  I  T  S  A  E  F  V  E  V  N  P  I  L  D  E  R  N
aaaacagcatcagtggctgtagcgctgatggggtcgttgtttggtgaaaaactcatgtaa
 K  T  A  S  V  A  V  A  L  M  G  S  L  F  G  E  K  L  M  -
```

FIG. 3C

```
atgaagccaatttcaattatcggggttccgatggatttagggcagacacgccgcggcgtt
 M  K  P  I  S  I  I  G  V  P  M  D  L  G  Q  T  R  R  G  V
gatatggggccgagcgcaatgcgttatgcaggcgtcatcgaacgtctggaacgtcttcat
 D  M  G  P  S  A  M  R  Y  A  G  V  I  E  R  L  E  R  L  H
tacgatattgaagatttgggagatattccgattggaaaagcagagcggttgcacgagcaa
 Y  D  I  E  D  L  G  D  I  P  I  G  K  A  E  R  L  H  E  Q
ggagattcacggttgcgcaatttgaaagcggttgcggaagcgaacgagaaacttgcggcg
 G  D  S  R  L  R  N  L  K  A  V  A  E  A  N  E  K  L  A  A
gcggttgaccaagtcgttcagcgggggcgatttccgcttgtgttgggcggcgaccatagc
 A  V  D  Q  V  V  Q  R  G  R  F  P  L  V  L  G  G  D  H  S
atcgccattggcacgctcgccggggtggcgaaacattatgagcggcttggagtgatctgg
 I  A  I  G  T  L  A  G  V  A  K  H  Y  E  R  L  G  V  I  W
tatgacgcgcatggcgacgtcaacaccgcggaaacgtcgccgtctggaaacattcatggc
 Y  D  A  H  G  D  V  N  T  A  E  T  S  P  S  G  N  I  H  G
atgccgctggcggcgagcctcgggtttggccatccggcgctgacgcaaatcggcggatac
 M  P  L  A  A  S  L  G  F  G  H  P  A  L  T  Q  I  G  G  Y
tgccccaaaatcaagccggaacatgtcgtgttgatcggcgtccgttcccttgatgaaggg
 C  P  K  I  K  P  E  H  V  V  L  I  G  V  R  S  L  D  E  G
gagaagaagtttattcgcgaaaaaggaatcaaaatttacacgatgcatgaggttgatcgg
 E  K  K  F  I  R  E  K  G  I  K  I  Y  T  M  H  E  V  D  R
ctcggaatgacaagggtgatggaagaaacgatcgcctatttaaaagaacgaacggatggc
 L  G  M  T  R  V  M  E  E  T  I  A  Y  L  K  E  R  T  D  G
gttcatttgtcgcttgacttggatggccttgacccaagcgacgcaccgggagtcggaacg
 V  H  L  S  L  D  L  D  G  L  D  P  S  D  A  P  G  V  G  T
cctgtcattggaggattgacataccgcgaaagccatttggcgatggagatgctggccgag
 P  V  I  G  G  L  T  Y  R  E  S  H  L  A  M  E  M  L  A  E
gcacaaatcatcacttcagcggaatttgtcgaagtgaacccgatcttggatgagcgaac
 A  Q  I  I  T  S  A  E  F  V  E  V  N  P  I  L  D  E  R  N
aaaacagcatcagtggctgtagcgctgatggggtcgttgtttggtgaaaaactcatg
 K  T  A  S  V  A  V  A  L  M  G  S  L  F  G  E  K  L  M  H
                      taa
 H  H  H  H           -
          ↑
```

FIG. 3D

| Lane 1: Low-range protein marker, Bio-Rad |
| Lane 2: Before chelating FF sepharose column (2.5 µL) |
| Lane 3: Flowthrough (2.5 µL) |
| Lane 4: Fraction A8 (10 µL) |
| Lane 5: Fraction C2 (10 µL) |
| Lane 6: Fraction C5 (10 µL) |
| Lane 7: Fraction C8 (10 µL) |
| Lane 8: Fraction C11 (10 µL) |
| Lane 9: Fraction D11 (10 µL) |
| Lane 10: Fraction D7 (10 µL) |

| Lane 1: Low-range marker, Bio-Rad |
| Lane 2: Before chelating FF sepharose column (2.5 µL) |
| Lane 3: Flowthrough (5 µL) |
| Lane 4: Fraction C1 (10 µL) |
| Lane 5: Fraction E7 (10 µL) |
| Lane 6: Fraction F7 (10 µL) |
| Lane 7: Fraction F6 (10 µL) |
| Lane 8: Fraction F3 (10 µL) |
| Lane 9: Fraction G2 (10 µL) |
| Lane 10: Fraction G5 (10 µL) |

| Lane 1: Low-range marker, Bio-Rad |
| Lane 2: Unpegylated human arginase I |
| Lane 3: Cys$^{45}$ pegylated human arginase I |

| Lane 1: Low-range marker, Bio-Rad |
| Lane 2: Unpegylated *Bacillus caldovelox* arginase |
| Lane 3: Cys$^{161}$ pegylated *Bacillus caldovelox* arginase |

(A)

Group 1

| | |
|---|---|
| Human ArgI (HAI) | LKEQECDVKDYGDLPFADIPNDSP---FQI-VKNPRSVGKASEQLAGKVAEVKKNGRISL 95 |
| Capra hircus ArgI | LKELECDVKDYGDLSFADNLDDSP---FQM-VKNPRCVGKANEKLADVVAEVKKTGRISL 95 |
| Heterocephalus glaber ArgI | LKEQECDVQDYGDLSFTDVPNDAP---FGI-MKNPRTVGKATEELAHMVAKVQKSGRVSL 91 |
| Bos taurus ArgI | LKELECDVKDYGDLSFADNLDDSP---FQI-VKNPRCVGKASEKLADVVAEVKKTGRISL 95 |
| Sus scrofa ArgI | LKEQECDVKDYGDLCFADVPNDTP---FQI-VKNPRSVGKANQQLADVVAEIKKNGRISL 95 |
| Plecoglossus altivelis ArgI | LKAQGCDVKDYGNLTFEEFSSDEP---IGR-VKRPRAVGRANERLAGAVDEVKKEGRTCV 103 |
| Salmo salar ArgI | LKAQGCAVKDYGNVTFEEVANDEP---IGN-VKRPRAVGSANQRLSAAVHAVKNDGHTCV 111 |
| Oncorhynchus mykiss ArgI | LRAQGCAVKDYGNVTFEEVANDEP---IGN-VKRPRAVGSANQRLSAAVHAVKNDGHTCV 112 |
| Osmerus mordax ArgI | LKAQGCDVKDYGNLMFEEFSSDEP---ISR-VKRPRAVGRANERLAGAVEEVKKEGRTCV 103 |
| Byriopsis cumingii Arg | LQNLGCHVQDEGDVEVIQVEKDDP----EEM-AKNPRTVGLTSKLIADKVERVLRSEDICL 103 |
| Rattus norvegicus ArgII | LSMLGCHLKDFGDLSFTNVPKDDP---YNMLVVYPRSVGIANQELAEVVSRAVSGGYSCV 114 |
| Mus musculus ArgII | LSRLGCHLKDFGDLSFTNVPQDDP---YNMLVVYPRSVGLANQELAEVVSRAVSGGYSCV 114 |
| Human ArgII | LSSLGCHLKDFGDLSFTPVPKDDL---YNMLIVNPRSVGLANQELAEVVSRAVSDGYSCV 114 |
| Bos taurus ArgII | LSDLGCHLKDFGDLNFTPVPKDDL---YNNLIVNPRSVGLANQELAEVVSRAVSGGYSCV 114 |
| Heterocephalus glaber ArgII | LSGLGCSLKDFGDLSFTPVAKDDP---FNNLVMNPRSVGLANQELTEVVSRAVSDGYSCV 114 |
| Pan troglodytes ArgII | LSSLGCHLKDFGDLSFTPVPKDDL---YNNLIVNPRSVGLANQELAEVVSRAVSDGYSCV 114 |
| Oryctolagus cuniculus ArgII | LSDLGCRLKDFGDLSFTPVPKDDL---YNNLIVNPRSVGLANQELAEVVKRAVSGGYSCV 114 |
| Delftia Arg | LPQLGCQVSDIGNLAGPPNDQTPP---EQG-LRHLAPARAMMDAVHQAVGPAIDDGELPI 109 |
| Bacillus coagulans Arg | LEHLGCAVTDLGNIEIGRAEQLPD--DEVN-ARNLKTIAKASQFIAEHTDEIVKSNRFPL 93 |
| Hoeflea phototrophica Arg | LAELGCSVEDRGDLAPRP--LAPENCANAA-VHHLAETIANTQALTSAAEAAM-AEGFPV 92 |
| Roseiflexus castenholzii Arg | IVALGCQVRDLGNISVPLAZQIEPPTPDER-LRYLQPIAHAVRDLAQRVRDVVASGALPL 94 |

(B)

Group 2

| | |
|---|---|
| Bacillus caldovelox (BCA) | IGGYSPKIKPEHVVLIGVRSLDE-GEKKFIREKGIKIYTMHEVDRLGMTRVMEEPIAYL 214 |
| Bacillus methanolicus | IGGYSPKVKPENIVIIGARSLDE-GERAAIKEKGIKVFTMHEIDRLGMSRVMEEPINYL 213 |
| Bacillus sp. NRRL B-14911 | IGGYSPKVKPENIVIIGARSLDE-GEKELVKEHGIKVYTMHEIDRLGMARVMEEAIEYL 213 |
| Planococcus donghaensis | IRGYSPKVKPENIVIIGARSVDP-GEREKLKEHGINRVYSMHEIDKMGMHAVIEEPSIKYL 215 |
| Paenibacillus dendritiformis | IRRQSSRIDPAKVVIIGARSLDE-GERAYIRQAGITCFTMRDIDRKGMPYVMEQALRIL 216 |
| Desmospora sp. | IGGYSPKVRPENVVIIGLRSLDE-GERVLIREQGIKVFTMRDIDRLGMGAVMEEPTLCIV 215 |
| Methylobacter tundripaludum | MYPGCDFIKPENLILIGVRSYEN-EEYDLLKQAKVEIIFAEQID--GLAQVLTKAIDKL 204 |
| Stenotrophomonas sp. | LGGTSPAITPAQMHQIGIRSVDP-EERKLIKTHKVRVYLMRYIDENCGMKRFVEAALAGI 219 |
| Microbacterium laevaniformans | ---PGCGAVTADRLVLVGARDLDP-GEAAHLAESEIRSVAAEAICDG----AAIAAAVA--- 189 |
| Porphyromonas uenonis | FWGYSPLIKPQNIYFLGARALDP-GEIEMAAKLNMYIRSSEQLNASDPAEVIVDILSDI 216 |
| Azorhizobium sp. | PPPLSHAVARENIGMIGIRSVDP-AEHAALEKSGITVHDMRSIDEBCVAVILREPIARV 214 |
| Octadecabacter arcticus | PPIVSNFVPTENICMIGLRSVDP-AEHAALANTPVEIALMRAIDEGGIRAPLAEPIAKV 215 |
| Agrobacterium tumefaciens | PPPLSHAVARENIGMIGIRSVDP-AERAALEKSGITVHDMRSIDEBCVAVITLREPIARV 214 |
| Anoxybacillus flavithermus | IGGYSPKVKPENIVIIGARSLDE-GEKQLIKEKGIHIVYTMHEIDRLGMTRVMEERTIAYL 213 |
| Bacillus pumilus | IGGYSPKIKPENVVLIGARSLDE-GERALIKEEGIKVFTMHEIDRLGMTRVMERAISYL 218 |
| Geobacillus thermoglucosidasius | IGGYSPKVKPENVVLIGVRSLDE-GEKQLIKEKGIKVYTMHEVDRLGMAAVMEETIAYL 221 |
| Geobacillus thermoglucosidans | IGGYSPKVKPENVVLIGVRSLDE-GEKQLIKEKGIKVYTMHEVDRLGMAAVMEETIAYL 221 |
| Brevibacillus laterosporus | IGGYSPKIKPESVVIIGARDLDE-GERELIKELGIKVYTMHEIDRLGMTRVMEETIEYV 213 |
| Desulfotomaculum ruminis | LGGLSPVQEDKTVLIGVRDLDY-NEKISLKNSRVVYSMKKIDELGMARVVKEAIAIA 212 |
| Geobacillus kaustophilus | IGGYSPKIKPESVVLIGVRSLDE-GEKKFIREKGIKIYTMHEVDRLGMTRVMEETITYL 214 |
| Geobacillus thermoleovorans | IGGYSPKVKPESVVLIGVRSLDE-GEKKFIREKGIKIYTMHEVDRLGMTRVMEETIAYL 214 |
| Geobacillus thermodenitrificans | IGGYSPKVKPESVVLIGVRSLDD-GEKKFIREKGIKIYTMHEVDRLGMTRVMEETIAYL 214 |
| Staphylococcus aureus | L---NNVIKPENIVLIGMRDLDK-GERQFIKDRNIKTFMSDIDKLGIKEVIENTIEYL 216 |
| Halophilic archaeon DL31 | ---ADREFADYANVSQVGIRGYTESPAFTEFADETGINLFTMHEVNEBGIGPVTEAAVEAA 252 |
| Halorisor xundwensis | N-AHSPRLREESVAYVGLRSIDERER-ELVRESEMTAFTMSDIEQBSMTAVVEDAIAVA 230 |
| Natrialba asyudii | ---ADSPHGSYETHAMIGLRAFEDPEYPSPVDESGLYVDYAHDVEHEGIEAVILADAIDRV 236 |

FIG. 19

(C)
Group 3

| | |
|---|---|
| Human ArgI (HAI) | LRGKIPDVPGFSWVTPCISAKDIVYIGLRDVDPGEHYILKTLGIKYFSMTEVDRLGIGKV 211 |
| Capra hircus ArgI | LKEKMPEVPGFHWLAPCISAKDIVYIGLRDVDPGEHYILKTLGIKYFSMTEVDRLGIGKV 211 |
| Heterocephalus glaber ArgI | LKEKMPDVPGFSWLTPCLSAKDIVYIGLRDVDPGEHHIVKTLGIKYFSMTEVDRLGIGKV 207 |
| Bos taurus ArgI | LKEKMPEVPGFYWVAPCISAKDIVYIGLRDVDPGEHYILKTLGIKYFSMTEVDRLGIGKV 211 |
| Sus scrofa ArgI | LKEKIPEVPGLSWVTPCLSAKDIVYIGLRDVDPAEHYILKTLGIKYFSMIEVDRLGIGKV 211 |
| Plecoglossus altivelis ArgI | LHSKIPVMPNFSWIKPCISAKDVVYIGLRDVDPEEHYILK-------------------- 199 |
| Salmo salar ArgI | LQSKIPVLPNFSWIKPCVSAKDIVYIGLRDVDPEEHHILKLLGIEVYSMTEVDRLGIAKV 227 |
| Oncorhynchus mykiss ArgI | LHSKIPVLPNFSWIKPCVSAKDIVYIGLRDVDPEEHHILTLLGVHGYSMTEVDRLGISKV 228 |
| Osmerus mordax ArgI | LHSKIPVIPNFSWIKPCVSAKDVVYIGLRDVDPEEHYILKYLGIKVFSMTDVDHLGIARV 225 |
| Hyriopsis cumingii Arg | LESYVTKLPGFEWLSPCIHAKDIAYIGLRDVDAGERKIIEKFGITAFSMQEVDKYGINEV 219 |
| Rattus norvegicus ArgII | LQDKVPQLPGFSWIKPCLSPPNIVYIGLRDVEPAEHFILKSFDIQYFSMDIDRLGIQKV 230 |
| Mus musculus ArgII | LQDKVPQLPGFSWIKPCLSPPNIVYIGLRDVEPPEHFILENYDIQYFSMDEIDRLGIQKV 230 |
| Human ArgII | LQDKVPQLPGFSWIKPCISSASIVYIGLRDVDPPEHFILENYDIQYFSMEDIDRLGIQKV 230 |
| Bos taurus ArgII | LQDKVPQLPGFSWIKPCISSPSIVYIGLRDVDPPEHFILKNYDIQYFSMDIDRLGIQKV 230 |
| Heterocephalus glaber ArgII | LQDKIPSLPGFSWIKPCISTPSIVYIGLRDVDPPEHFILKNYDIQYFSMRDIDQLGIKKV 230 |
| Pan troglodytes ArgII | LQDKVPQLPGFSWIKPCISSASIVYIGLRDVDPPEHFILENYDIQYFSMEDIDRLGIQKV 230 |
| Oryctolagus cuniculus ArgII | LQDKVPQLPGFSWIKPCISSPSIVYIGLRDVDPPEHFILKKYDIQYFSMRDIDRLGIQKV 230 |

(D)
Group 4

| | |
|---|---|
| Bacillus caldovelox (BCA) | ------MKPISIIGVPMDLGQTRRGVDMGPSAMRYAGVIERLERLHYDIEDLGDIPIGKA 54 |
| Bacillus methanolicus | ------MKKISIIGVPMDLGQMRRGVDMGPSAMRYAGINERLRNLKYEIEDLGDIPIGRP 54 |
| Desmospora sp. | -----MBNMNITIVGVPMDLGADRRGVDMGPSAIRIASLKEKLTGLGYVKDSGNLAVPTP 56 |
| Geobacillus thermoglucosidasius | MERGNSVKKVSIIGVPMELGQTRRGVDMGPSAMRIAGIIERLERLHYEIEDLGDVSIGKM 60 |
| Geobacillus thermoglucosidans | MERGNSVKKVSIIGVPMELGQTRRGVDMGPSAMRIAGIIERLERLHYEIEDLGDVSIGKM 60 |
| Brevibacillus laterosporus | -------MNKKISLIGVPLDLGADRRGVDMGPSAIRIAGVVKRLEGLGYSVKDLGDIPVIBF 55 |
| Geobacillus kaustophilus | ------MKPISIIGVPMDLGQTRRGVDMGPSAMRIAGIIERLERLHYEIEDLGDIPIGKA 54 |
| Geobacillus thermoleovorans | ------MKPISIIGVPMDLGQTRRGVDMGPSAMRYAGVIERLERLHYEIEDLGDIPIGKA 54 |
| Geobacillus thermodenitrificans | ------MKPISIIGVPMDLGQTRRGVDMGPSAIRYAGVIERLERLHYEIEDLGDIPIGKV 54 |

FIG. 19 (Cont'd)

(A)
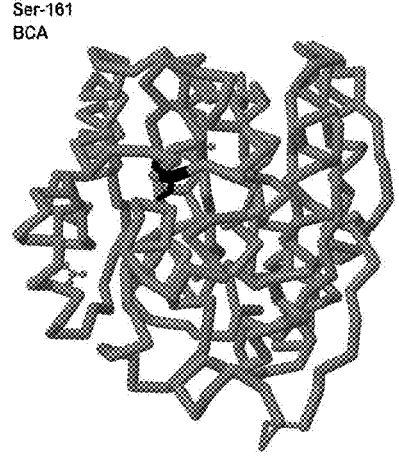
(B)
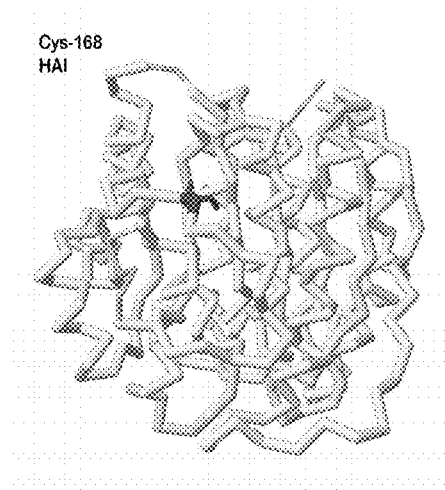
(C)
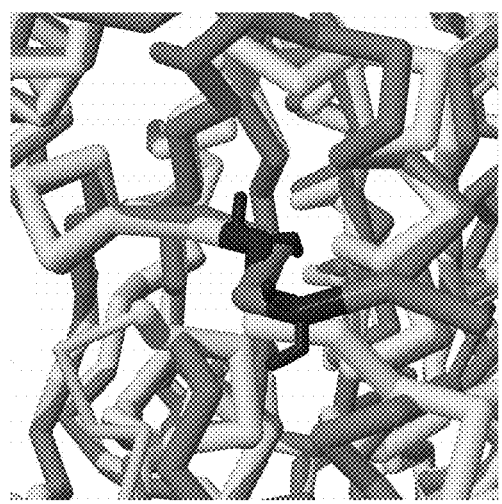
FIG.20

(A)
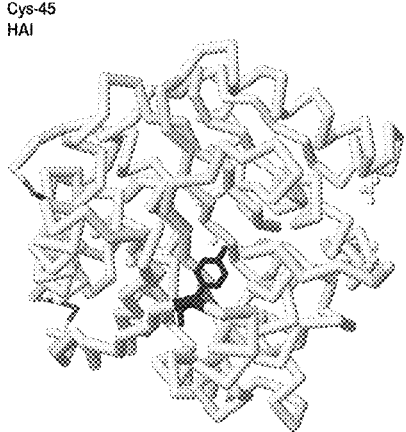
(B)
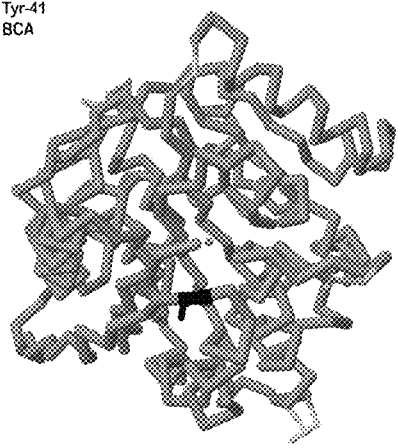
(C)
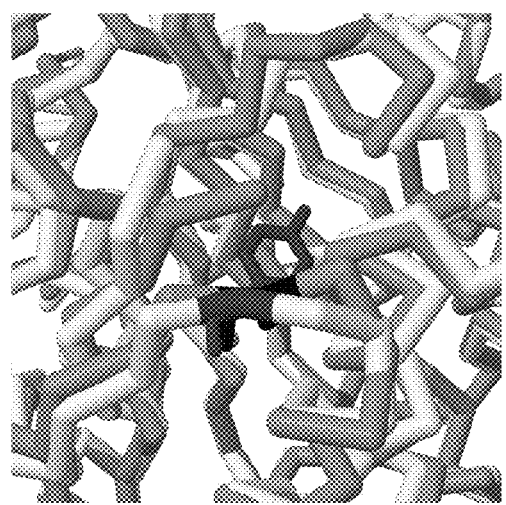
FIG.21

SEQUENCE LISTING

```
<160> NUMBER OF SEQ ID NOS: 67

<210> SEQ ID NO 1
<211> LENGTH: 969
<212> TYPE: DNA
<213> ORGANISM: Homo sapiens

<400> SEQUENCE: 1
atgagcgcca agtccagaac catagggatt attggagctc ctttctcaaa gggacagcca      60
cgaggagggg tggaagaagg ccctacagta ttgagaaagg ctggtctgct tgagaaactt     120
aaagaacaag agtgtgatgt gaaggattat ggggacctgc cctttgctga catccctaat     180
gacagtccct ttcaaattgt gaagaatcca aggtctgtgg gaaaagcaag cgagcagctg     240
gctggcaagg tggcagaagt caagaagaac ggaagaatca gcctggtgct gggcggagac     300
cacagtttgg caattggaag catctctggc catgccaggg tccaccctga tcttggagtc     360
atctgggtgg atgctcacac tgatatcaac actccactga caaccacaag tggaaacttg     420
catggacaac ctgtatcttt cctcctgaag gaactaaaag gaaagattcc cgatgtgcca     480
ggattctcct gggtgactcc ctgtatatct gccaaggata ttgtgtatat tggcttgaga     540
gacgtggacc ctggggaaca ctacattttg aaaactctag gcattaaata cttttcaatg     600
actgaagtgg acagactagg aattggcaag gtgatggaag aaacactcag ctatctacta     660
ggaagaaaga aaaggccaat tcatctaagt tttgatgttg acggactgga cccatctttc     720
acaccagcta ctggcacacc agtcgtggga ggtctgacat acagagaagg tctctacatc     780
acagaagaaa tctacaaaac agggctactc tcaggattag atataatgga agtgaaccca     840
tccctgggga agacaccaga agaagtaact cgaacagtga acacagcagt tgcaataacc     900
ttggcttgtt tcggacttgc tcgggagggt aatcacaagc ctattgacta ccttaaccca     960
cctaagtaa                                                             969

<210> SEQ ID NO 2
<211> LENGTH: 969
<212> TYPE: DNA
<213> ORGANISM: artificial sequence
<220> FEATURE:
<223> OTHER INFORMATION: Human arginase I designed for site-directed
      pegylation

<400> SEQUENCE: 2
atgagcgcca agtccagaac catagggatt attggagctc ctttctcaaa gggacagcca      60
cgaggagggg tggaagaagg ccctacagta ttgagaaagg ctggtctgct tgagaaactt     120
aaagaacaag agtgtgatgt gaaggattat ggggacctgc cctttgctga catccctaat     180
gacagtccct ttcaaattgt gaagaatcca aggtctgtgg gaaaagcaag cgagcagctg     240
gctggcaagg tggcagaagt caagaagaac ggaagaatca gcctggtgct gggcggagac     300
```

```
cacagtttgg caattggaag catctctggc catgccaggg tccaccctga tcttggagtc    360
atctgggtgg atgctcacac tgatatcaac actccactga caaccacaag tggaaacttg    420
catggacaac ctgtatcttt cctcctgaag gaactaaaag gaaagattcc cgatgtgcca    480
ggattctcct gggtgactcc ctctatatct gccaaggata ttgtgtatat tggcttgaga    540
gacgtggacc ctggggaaca ctacattttg aaaactctag cattaaata cttttcaatg     600 actgaagtgg acagactagg aattggcaag gtgatggaag aaacactcag ctatctacta    660
ggaagaaaga aaaggccaat tcatctaagt tttgatgttg acggactgga cccatctttc    720
acaccagcta ctggcacacc agtcgtggga ggtctgacat acagaaagg tctctacatc     780 acagaagaaa tctacaaaac agggctactc tcaggattag atataatgga agtgaaccca    840
tccctgggga agacaccaga agaagtaact cgaacagtga acacagcagt tgcaataacc    900
ttggcttctt tcggacttgc tcgggagggt aatcacaagc ctattgacta ccttaaccca    960
cctaagtaa                                                             969

<210> SEQ ID NO 3
<211> LENGTH: 900
<212> TYPE: DNA
<213> ORGANISM: Bacillus caldovelox

<400> SEQUENCE: 3
atgaagccaa tttcaattat cggggttccg atggatttag gcagacacg ccgcggcgtt      60 gatatggggc cgagcgcaat gcgttatgca ggcgtcatcg aacgtctgga acgtcttcat    120
tacgatattg aagatttggg agatattccg attggaaaag cagagcggtt gcacgagcaa    180
ggagattcac ggttgcgcaa tttgaaagcg gttgcggaag cgaacgagaa acttgcggcg    240
gcggttgacc aagtcgttca gcgggggcga tttccgcttg tgttgggcgg cgaccatagc    300
atcgccattg gcacgctcgc cggggtggcg aaacattatg agcggcttgg agtgatctgg    360
tatgacgcgc atgcgacgt caacaccgcg gaaacgtcgc cgtctggaaa cattcatggc    420
atgccgctgg cggcgagcct cggtttggc catccggcgc tgacgcaaat cggcggatac    480
agccccaaaa tcaagccgga acatgtcgtg ttgatcggcg tccgttccct tgatgaaggg    540
gagaagaagt ttattcgcga aaaggaatc aaaatttaca cgatgcatga ggttgatcgg     600
ctcggaatga caagggtgat ggaagaaacg atcgcctatt aaaagaacg aacgatggc      660 gttcatttgt cgcttgactt ggatggcctt gacccaagcg acgcaccggg agtcggaacg    720
cctgtcattg gaggattgac ataccgcgaa agccatttgg cgatggagat gctggccgag    780
gcacaaatca tcacttcagc ggaatttgtc gaagtgaacc cgatcttgga tgagcggaac    840
aaaacagcat cagtggctgt agcgctgatg gggtcgttgt ttggtgaaaa actcatgtaa    900

<210> SEQ ID NO 4
<211> LENGTH: 918
<212> TYPE: DNA
<213> ORGANISM: artificial sequence
<220> FEATURE:
<223> OTHER INFORMATION: Bacillus caldovelox arginase designed for
      site-directed pegylation

<400> SEQUENCE: 4
atgaagccaa tttcaattat cggggttccg atggatttag gcagacacg ccgcggcgtt      60 gatatggggc cgagcgcaat gcgttatgca ggcgtcatcg aacgtctgga acgtcttcat    120
tacgatattg aagatttggg agatattccg attggaaaag cagagcggtt gcacgagcaa    180
```

```
ggagattcac ggttgcgcaa tttgaaagcg gttgcggaag cgaacgagaa acttgcggcg    240
gcggttgacc aagtcgttca gcggggggcga tttccgcttg tgttgggcgg cgaccatagc   300
atcgccattg gcacgctcgc cggggtggcg aaacattatg agcggcttgg agtgatctgg   360
tatgacgcgc atggcgacgt caacaccgcg gaaacgtcgc cgtctggaaa cattcatggc   420
atgccgctgg cggcgagcct cgggtttggc catccggcgc tgacgcaaat cggcggatac   480
tgccccaaaa tcaagccgga acatgtcgtg ttgatcggcg tccgttccct tgatgaaggg   540
gagaagaagt ttattcgcga aaaggaatc aaaatttaca cgatgcatga ggttgatcgg    600
ctcggaatga caagggtgat ggaagaaacg atcgcctatt taaaagaacg aacggatggc   660
gttcatttgt cgcttgactt ggatggcctt gacccaagcg acgcaccggg agtcggaacg   720
cctgtcattg gaggattgac ataccgcgaa agccatttgg cgatggagat gctggccgag   780
gcacaaatca tcacttcagc ggaatttgtc gaagtgaacc cgatcttgga tgagcggaac   840
aaaacagcat cagtggctgt agcgctgatg gggtcgttgt ttggtgaaaa actcatgcat   900
caccatcacc atcactaa                                                 918
```

<210> SEQ ID NO 5
<211> LENGTH: 322
<212> TYPE: PRT
<213> ORGANISM: Homo sapiens

<400> SEQUENCE: 5

```
Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240
```

Thr Pro Ala Thr Gly Thr Pro Val Val Gly Leu Thr Tyr Arg Glu
            245                 250                 255

Gly Leu Tyr Ile Thr Glu Glu Ile Tyr Lys Thr Gly Leu Leu Ser Gly
        260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Cys Phe
290                 295                 300

Gly Leu Ala Arg Glu Gly Asn His Lys Pro Ile Asp Tyr Leu Asn Pro
305                 310                 315                 320

Pro Lys

<210> SEQ ID NO 6
<211> LENGTH: 322
<212> TYPE: PRT
<213> ORGANISM: artificial sequence
<220> FEATURE:
<223> OTHER INFORMATION: amino acid sequence of human arginase I with
      Cys168 and Cys303 replaced by Ser

<400> SEQUENCE: 6

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Ser Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Leu Thr Tyr Arg Glu
            245                 250                 255

Gly Leu Tyr Ile Thr Glu Glu Ile Tyr Lys Thr Gly Leu Leu Ser Gly
        260                 265                 270

```
Leu Asp Ile Met Glu Val Asn Pro Ser Leu Gly Lys Thr Pro Glu Glu
            275                 280                 285

Val Thr Arg Thr Val Asn Thr Ala Val Ala Ile Thr Leu Ala Ser Phe
        290                 295                 300

Gly Leu Ala Arg Glu Gly Asn His Lys Pro Ile Asp Tyr Leu Asn Pro
305                 310                 315                 320

Pro Lys

<210> SEQ ID NO 7
<211> LENGTH: 299
<212> TYPE: PRT
<213> ORGANISM: Bacillus caldovelox

<400> SEQUENCE: 7

Met Lys Pro Ile Ser Ile Ile Gly Val Pro Met Asp Leu Gly Gln Thr
1               5                   10                  15

Arg Arg Gly Val Asp Met Gly Pro Ser Ala Met Arg Tyr Ala Gly Val
            20                  25                  30

Ile Glu Arg Leu Glu Arg Leu His Tyr Asp Ile Glu Asp Leu Gly Asp
        35                  40                  45

Ile Pro Ile Gly Lys Ala Glu Arg Leu His Glu Gln Gly Asp Ser Arg
    50                  55                  60

Leu Arg Asn Leu Lys Ala Val Ala Glu Ala Asn Glu Lys Leu Ala Ala
65                  70                  75                  80

Ala Val Asp Gln Val Val Gln Arg Gly Arg Phe Pro Leu Val Leu Gly
                85                  90                  95

Gly Asp His Ser Ile Ala Ile Gly Thr Leu Ala Gly Val Ala Lys His
            100                 105                 110

Tyr Glu Arg Leu Gly Val Ile Trp Tyr Asp Ala His Gly Asp Val Asn
        115                 120                 125

Thr Ala Glu Thr Ser Pro Ser Gly Asn Ile His Gly Met Pro Leu Ala
    130                 135                 140

Ala Ser Leu Gly Phe Gly His Pro Ala Leu Thr Gln Ile Gly Gly Tyr
145                 150                 155                 160

Ser Pro Lys Ile Lys Pro Glu His Val Val Leu Ile Gly Val Arg Ser
                165                 170                 175

Leu Asp Glu Gly Glu Lys Lys Phe Ile Arg Glu Lys Gly Ile Lys Ile
            180                 185                 190

Tyr Thr Met His Glu Val Asp Arg Leu Gly Met Thr Arg Val Met Glu
        195                 200                 205

Glu Thr Ile Ala Tyr Leu Lys Glu Arg Thr Asp Gly Val His Leu Ser
    210                 215                 220

Leu Asp Leu Asp Gly Leu Asp Pro Ser Asp Ala Pro Gly Val Gly Thr
225                 230                 235                 240

Pro Val Ile Gly Gly Leu Thr Tyr Arg Glu Ser His Leu Ala Met Glu
                245                 250                 255

Met Leu Ala Glu Ala Gln Ile Ile Thr Ser Ala Glu Phe Val Glu Val
            260                 265                 270

Asn Pro Ile Leu Asp Glu Arg Asn Lys Thr Ala Ser Val Ala Val Ala
        275                 280                 285

Leu Met Gly Ser Leu Phe Gly Glu Lys Leu Met
    290                 295

<210> SEQ ID NO 8
<211> LENGTH: 305
```

<212> TYPE: PRT
<213> ORGANISM: artificial sequence
<220> FEATURE:
<223> OTHER INFORMATION: amino acid sequence of 6xHis-tagged Bacillus
      caldovelox arginase with Ser161 replaced by Cys.

<400> SEQUENCE: 8

Met Lys Pro Ile Ser Ile Ile Gly Val Pro Met Asp Leu Gly Gln Thr
1               5                   10                  15

Arg Arg Gly Val Asp Met Gly Pro Ser Ala Met Arg Tyr Ala Gly Val
            20                  25                  30

Ile Glu Arg Leu Glu Arg Leu His Tyr Asp Ile Glu Asp Leu Gly Asp
        35                  40                  45

Ile Pro Ile Gly Lys Ala Glu Arg Leu His Glu Gln Gly Asp Ser Arg
    50                  55                  60

Leu Arg Asn Leu Lys Ala Val Ala Glu Ala Asn Glu Lys Leu Ala Ala
65                  70                  75                  80

Ala Val Asp Gln Val Val Gln Arg Gly Arg Phe Pro Leu Val Leu Gly
                85                  90                  95

Gly Asp His Ser Ile Ala Ile Gly Thr Leu Ala Gly Val Ala Lys His
            100                 105                 110

Tyr Glu Arg Leu Gly Val Ile Trp Tyr Asp Ala His Gly Asp Val Asn
        115                 120                 125

Thr Ala Glu Thr Ser Pro Ser Gly Asn Ile His Gly Met Pro Leu Ala
    130                 135                 140

Ala Ser Leu Gly Phe Gly His Pro Ala Leu Thr Gln Ile Gly Gly Tyr
145                 150                 155                 160

Cys Pro Lys Ile Lys Pro Glu His Val Val Leu Ile Gly Val Arg Ser
                165                 170                 175

Leu Asp Glu Gly Glu Lys Lys Phe Ile Arg Glu Lys Gly Ile Lys Ile
            180                 185                 190

Tyr Thr Met His Glu Val Asp Arg Leu Gly Met Thr Arg Val Met Glu
        195                 200                 205

Glu Thr Ile Ala Tyr Leu Lys Glu Arg Thr Asp Gly Val His Leu Ser
    210                 215                 220

Leu Asp Leu Asp Gly Leu Asp Pro Ser Asp Ala Pro Gly Val Gly Thr
225                 230                 235                 240

Pro Val Ile Gly Gly Leu Thr Tyr Arg Glu Ser His Leu Ala Met Glu
                245                 250                 255

Met Leu Ala Glu Ala Gln Ile Ile Thr Ser Ala Glu Phe Val Glu Val
            260                 265                 270

Asn Pro Ile Leu Asp Glu Arg Asn Lys Thr Ala Ser Val Ala Val Ala
        275                 280                 285

Leu Met Gly Ser Leu Phe Gly Glu Lys Leu Met His His His His His
    290                 295                 300

His
305

<210> SEQ ID NO 9
<211> LENGTH: 969
<212> TYPE: DNA
<213> ORGANISM: artificial sequence
<220> FEATURE:
<223> OTHER INFORMATION: human arginase I mutant (C168S/C303S)

<400> SEQUENCE: 9
atgagcgcca agtccagaac catagggatt attggagctc ctttctcaaa gggacagcca      60

-continued

```
cgaggagggg tggaagaagg ccctacagta ttgagaaagg ctggtctgct tgagaaactt    120
aaagaacaag agtgtgatgt gaaggattat ggggaccctgc cctttgctga catccctaat    180
gacagtccct ttcaaattgt gaagaatcca aggtctgtgg aaaagcaag cgagcagctg    240
gctggcaagt ggcagaagt caagaagaac ggaagaatca gcctggtgct gggcggagac    300
cacagtttgg caattggaag catctctggc catgccaggg tccaccctga tcttggagtc    360
atctgggtgg atgctcacac tgatatcaac actccactga caaccacaag tggaaacttg    420
catggacaac ctgtatcttt cctcctgaag gaactaaaag gaaagattcc cgatgtgcca    480
ggattctcct gggtgactcc ctctatatct gccaaggata ttgtgtatat tggcttgaga    540
gacgtggacc ctggggaaca ctacattttg aaaactctag gcattaaata cttttcaatg    600
actgaagtgg acagactagg aattggcaag gtgatggaag aaacactcag ctatctacta    660
ggaagaaaga aaaggccaat tcatctaagt tttgatgttg acggactgga cccatctttc    720
acaccagcta ctggcacacc agtcgtggga ggtctgacat acagagaagg tctctacatc    780
acagaagaaa tctacaaaac agggctactc tcaggattag atataatgga agtgaaccca    840
tccctgggga agacaccaga agaagtaact cgaacagtga acacagcagt tgcaataacc    900
ttggcttctt tcggacttgc tcgggagggt aatcacaagc ctattgacta ccttaaccca    960
cctaagtaa                                                             969
```

```
<210> SEQ ID NO 10
<211> LENGTH: 322
<212> TYPE: PRT
<213> ORGANISM: artificial sequence
<220> FEATURE:
<223> OTHER INFORMATION: human arginase I mutant (C168S/C303S)

<400> SEQUENCE: 10

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Ser Ile Ser Ala Lys Asp Ile Val Tyr
                165                 170                 175

Ile Gly Leu Arg Asp Val Asp Pro Gly Glu His Tyr Ile Leu Lys Thr
            180                 185                 190
```

```
Leu Gly Ile Lys Tyr Phe Ser Met Thr Glu Val Asp Arg Leu Gly Ile
            195                 200                 205
Gly Lys Val Met Glu Glu Thr Leu Ser Tyr Leu Leu Gly Arg Lys Lys
        210                 215                 220
Arg Pro Ile His Leu Ser Phe Asp Val Asp Gly Leu Asp Pro Ser Phe
225                 230                 235                 240
Thr Pro Ala Thr Gly Thr Pro Val Val Gly Gly Leu Thr Tyr Arg Glu
                245                 250                 255
Gly Leu Tyr Ile Thr Glu Glu Ile Tyr Lys Thr Gly Leu Leu Ser Gly
            260                 265                 270
Leu Asp Ile Met Glu Val Asn Pro Ser Leu Gly Lys Thr Pro Glu Glu
        275                 280                 285
Val Thr Arg Thr Val Asn Thr Ala Val Ala Ile Thr Leu Ala Ser Phe
    290                 295                 300
Gly Leu Ala Arg Glu Gly Asn His Lys Pro Ile Asp Tyr Leu Asn Pro
305                 310                 315                 320
Pro Lys
```

<210> SEQ ID NO 11
<211> LENGTH: 990
<212> TYPE: DNA
<213> ORGANISM: artificial sequence
<220> FEATURE:
<223> OTHER INFORMATION: 6xHis-tagged human arginase I mutant
      (C168S/C303S)

<400> SEQUENCE: 11

```
atgcatcacc atcaccatca catgagcgcc aagtccagaa ccatagggat tattggagct    60
cctttctcaa agggacagcc acgaggaggg gtggaagaag ccctacagt  attgagaaag   120
gctggtctgc ttgagaaact taagaacaa  gagtgtgatg tgaaggatta tggggacctg   180
ccctttgctg acatccctaa tgacagtccc tttcaaattg tgaagaatcc aaggtctgtg   240
ggaaaagcaa gcgagcagct ggctggcaag gtggcagaag tcaagaagaa cggaagaatc   300
agcctggtgc tgggcggaga ccacagtttg gcaattggaa gcatctctgg ccatgccagg   360
gtccaccctg atcttggagt catctgggtg atgctcaca  ctgatatcaa cactccactg   420
acaaccacaa gtggaaactt gcatggacaa cctgtatctt cctcctgaa  ggaactaaaa   480
ggaaagattc ccgatgtgcc aggattctcc tgggtgactc cctctatatc tgccaaggat   540
attgtgtata ttggcttgag agacgtggac cctggggaac actacatttt gaaaactcta   600
ggcattaaat acttttcaat gactgaagtg gacagactag gaattggcaa ggtgatggaa   660
gaaacactca gctatctact aggaagaaag aaaaggccaa ttcatctaag ttttgatgtt   720
gacggactgg acccatcttt cacaccagct actggcacac cagtcgtggg aggtctgaca   780
tacagagaag gtctctacat cacagaagaa atctacaaaa cagggctact ctcaggatta   840
gatataatgg aagtgaaccc atccctgggg aagacaccag aagaagtaac tcgaacagtg   900
aacacagcag ttgcaataac cttggcttct ttcggacttg ctcgggaggg taatcacaag   960
cctattgact accttaaccc acctaagtaa                                    990
```

<210> SEQ ID NO 12
<211> LENGTH: 329
<212> TYPE: PRT
<213> ORGANISM: artificial sequence
<220> FEATURE:
<223> OTHER INFORMATION: 6xHis-tagged human arginase I mutant
      (C168S/C303S)

<400> SEQUENCE: 12

```
Met His His His His His Met Ser Ala Lys Ser Arg Thr Ile Gly
1               5                   10                  15

Ile Ile Gly Ala Pro Phe Ser Lys Gly Gln Pro Arg Gly Val Glu
            20                  25                  30

Glu Gly Pro Thr Val Leu Arg Lys Ala Gly Leu Leu Glu Lys Leu Lys
        35                  40                  45

Glu Gln Glu Cys Asp Val Lys Asp Tyr Gly Asp Leu Pro Phe Ala Asp
    50                  55                  60

Ile Pro Asn Asp Ser Pro Phe Gln Ile Val Lys Asn Pro Arg Ser Val
65                  70                  75                  80

Gly Lys Ala Ser Glu Gln Leu Ala Gly Lys Val Ala Glu Val Lys Lys
                85                  90                  95

Asn Gly Arg Ile Ser Leu Val Leu Gly Gly Asp His Ser Leu Ala Ile
            100                 105                 110

Gly Ser Ile Ser Gly His Ala Arg Val His Pro Asp Leu Gly Val Ile
        115                 120                 125

Trp Val Asp Ala His Thr Asp Ile Asn Thr Pro Leu Thr Thr Thr Ser
130                 135                 140

Gly Asn Leu His Gly Gln Pro Val Ser Phe Leu Leu Lys Glu Leu Lys
145                 150                 155                 160

Gly Lys Ile Pro Asp Val Pro Gly Phe Ser Trp Val Thr Pro Ser Ile
                165                 170                 175

Ser Ala Lys Asp Ile Val Tyr Ile Gly Leu Arg Asp Val Asp Pro Gly
            180                 185                 190

Glu His Tyr Ile Leu Lys Thr Leu Gly Ile Lys Tyr Phe Ser Met Thr
        195                 200                 205

Glu Val Asp Arg Leu Gly Ile Gly Lys Val Met Glu Glu Thr Leu Ser
    210                 215                 220

Tyr Leu Leu Gly Arg Lys Lys Arg Pro Ile His Leu Ser Phe Asp Val
225                 230                 235                 240

Asp Gly Leu Asp Pro Ser Phe Thr Pro Ala Thr Gly Thr Pro Val Val
                245                 250                 255

Gly Gly Leu Thr Tyr Arg Glu Gly Leu Tyr Ile Thr Glu Glu Ile Tyr
            260                 265                 270

Lys Thr Gly Leu Leu Ser Gly Leu Asp Ile Met Glu Val Asn Pro Ser
        275                 280                 285

Leu Gly Lys Thr Pro Glu Glu Val Thr Arg Thr Val Asn Thr Ala Val
    290                 295                 300

Ala Ile Thr Leu Ala Ser Phe Gly Leu Ala Arg Glu Gly Asn His Lys
305                 310                 315                 320

Pro Ile Asp Tyr Leu Asn Pro Pro Lys
                325
```

<210> SEQ ID NO 13
<211> LENGTH: 900
<212> TYPE: DNA
<213> ORGANISM: artificial sequence
<220> FEATURE:
<223> OTHER INFORMATION: Bacillus caldovelox arginase mutant (S161C)

<400> SEQUENCE: 13

```
atgaagccaa tttcaattat cggggttccg atggatttag gcagacacg  ccgcggcgtt    60 gatatggggc cgagcgcaat gcgttatgca ggcgtcatcg aacgtctgga acgtcttcat   120
```

```
tacgatattg aagatttggg agatattccg attggaaaag cagagcggtt gcacgagcaa    180
ggagattcac ggttgcgcaa tttgaaagcg gttgcggaag cgaacgagaa acttgcggcg    240
gcggttgacc aagtcgttca gcggggggcga tttccgcttg tgttgggcgg cgaccatagc    300
atcgccattg gcacgctcgc cggggtggcg aaacattatg agcggcttgg agtgatctgg    360
tatgacgcgc atggcgacgt caacaccgcg gaaacgtcgc cgtctggaaa cattcatggc    420
atgccgctgg cggcgagcct cgggtttggc catccggcgc tgacgcaaat cggcggatac    480
tgccccaaaa tcaagccgga acatgtcgtg ttgatcggcg tccgttccct tgatgaaggg    540
gagaagaagt ttattcgcga aaaggaatc aaaatttaca cgatgcatga ggttgatcgg    600
ctcggaatga caagggtgat ggaagaaacg atcgcctatt taaaagaacg aacggatggc    660
gttcatttgt cgcttgactt ggatggcctt gacccaagcg acgcaccggg agtcggaacg    720
cctgtcattg gaggattgac ataccgcgaa agccatttgg cgatggagat gctggccgag    780
gcacaaatca tcacttcagc ggaatttgtc gaagtgaacc cgatcttgga tgagcggaac    840
aaaacagcat cagtggctgt agcgctgatg gggtcgttgt ttggtgaaaa actcatgtaa    900
```

<210> SEQ ID NO 14
<211> LENGTH: 299
<212> TYPE: PRT
<213> ORGANISM: artificial sequence
<220> FEATURE:
<223> OTHER INFORMATION: Bacillus caldovelox arginase mutant (S161C)

<400> SEQUENCE: 14

```
Met Lys Pro Ile Ser Ile Ile Gly Val Pro Met Asp Leu Gly Gln Thr
1               5                   10                  15

Arg Arg Gly Val Asp Met Gly Pro Ser Ala Met Arg Tyr Ala Gly Val
            20                  25                  30

Ile Glu Arg Leu Glu Arg Leu His Tyr Asp Ile Glu Asp Leu Gly Asp
        35                  40                  45

Ile Pro Ile Gly Lys Ala Glu Arg Leu His Glu Gln Gly Asp Ser Arg
    50                  55                  60

Leu Arg Asn Leu Lys Ala Val Ala Glu Ala Asn Glu Lys Leu Ala Ala
65                  70                  75                  80

Ala Val Asp Gln Val Val Gln Arg Gly Arg Phe Pro Leu Val Leu Gly
                85                  90                  95

Gly Asp His Ser Ile Ala Ile Gly Thr Leu Ala Gly Val Ala Lys His
            100                 105                 110

Tyr Glu Arg Leu Gly Val Ile Trp Tyr Asp Ala His Gly Asp Val Asn
        115                 120                 125

Thr Ala Glu Thr Ser Pro Ser Gly Asn Ile His Gly Met Pro Leu Ala
    130                 135                 140

Ala Ser Leu Gly Phe Gly His Pro Ala Leu Thr Gln Ile Gly Gly Tyr
145                 150                 155                 160

Cys Pro Lys Ile Lys Pro Glu His Val Val Leu Ile Gly Val Arg Ser
                165                 170                 175

Leu Asp Glu Gly Glu Lys Lys Phe Ile Arg Glu Lys Gly Ile Lys Ile
            180                 185                 190

Tyr Thr Met His Glu Val Asp Arg Leu Gly Met Thr Arg Val Met Glu
        195                 200                 205

Glu Thr Ile Ala Tyr Leu Lys Glu Arg Thr Asp Gly Val His Leu Ser
    210                 215                 220
```

```
Leu Asp Leu Asp Gly Leu Asp Pro Ser Asp Ala Pro Gly Val Gly Thr
225                 230                 235                 240

Pro Val Ile Gly Gly Leu Thr Tyr Arg Glu Ser His Leu Ala Met Glu
            245                 250                 255

Met Leu Ala Glu Ala Gln Ile Ile Thr Ser Ala Glu Phe Val Glu Val
        260                 265                 270

Asn Pro Ile Leu Asp Glu Arg Asn Lys Thr Ala Ser Val Ala Val Ala
    275                 280                 285

Leu Met Gly Ser Leu Phe Gly Glu Lys Leu Met
    290                 295

<210> SEQ ID NO 15
<211> LENGTH: 918
<212> TYPE: DNA
<213> ORGANISM: artificial sequence
<220> FEATURE:
<223> OTHER INFORMATION: 6xHis-tagged Bacillus caldovelox arginase
      mutant (S161C)

<400> SEQUENCE: 15
atgaagccaa tttcaattat cggggttccg atggatttag ggcagacacg ccgcggcgtt      60
gatatgggc cgagcgcaat gcgttatgca ggcgtcatcg aacgtctgga acgtcttcat     120
tacgatattg aagatttggg agatattccg attggaaaag cagagcggtt gcacgagcaa     180
ggagattcac ggttgcgcaa tttgaaagcg gttgcgaaag cgaacgagaa acttgcggcg     240
gcggttgacc aagtcgttca gcggggcga tttccgcttg tgttgggcgg cgaccatagc     300
atcgccattg gcacgctcgc cggggtggcg aaacattatg agcggcttgg agtgatctgg     360
tatgacgcgc atggcgacgt caacaccgcg gaaacgtcgc cgtctggaaa cattcatggc     420
atgccgctgg cggcgagcct cgggtttggc catccggcgc tgacgcaaat cggcggatac     480
tgccccaaaa tcaagccgga acatgtcgtg ttgatcggcg tccgttccct tgatgaaggg     540
gagaagaagt ttattcgcga aaaggaatc aaaatttaca cgatgcatga ggttgatcgg     600
ctcggaatga caagggtgat ggaagaaacg atcgcctatt aaaagaacg aacggatggc     660
gttcatttgt cgcttgactt ggatggcctt gacccaagcg acgcaccggg agtcggaacg     720
cctgtcattg gaggattgac ataccgcgaa agccatttgg cgatggagat gctggccgag     780
gcacaaatca tcacttcagc ggaatttgtc gaagtgaacc cgatcttgga tgagcggaac     840
aaaacagcat cagtggctgt agcgctgatg gggtcgttgt ttggtgaaaa actcatgcat     900
caccatcacc atcactaa                                                  918

<210> SEQ ID NO 16
<211> LENGTH: 305
<212> TYPE: PRT
<213> ORGANISM: artificial sequence
<220> FEATURE:
<223> OTHER INFORMATION: 6xHis-tagged Bacillus caldovelox arginase
      mutant (S161C)

<400> SEQUENCE: 16

Met Lys Pro Ile Ser Ile Ile Gly Val Pro Met Asp Leu Gly Gln Thr
1               5                   10                  15

Arg Arg Gly Val Asp Met Gly Pro Ser Ala Met Arg Tyr Ala Gly Val
            20                  25                  30

Ile Glu Arg Leu Glu Arg Leu His Tyr Asp Ile Glu Asp Leu Gly Asp
        35                  40                  45

Ile Pro Ile Gly Lys Ala Glu Arg Leu His Glu Gln Gly Asp Ser Arg
```

```
            50                  55                  60
Leu Arg Asn Leu Lys Ala Val Ala Glu Ala Asn Glu Lys Leu Ala Ala
 65                  70                  75                  80

Ala Val Asp Gln Val Val Gln Arg Gly Arg Phe Pro Leu Val Leu Gly
                 85                  90                  95

Gly Asp His Ser Ile Ala Ile Gly Thr Leu Ala Gly Val Ala Lys His
            100                 105                 110

Tyr Glu Arg Leu Gly Val Ile Trp Tyr Asp Ala His Gly Asp Val Asn
        115                 120                 125

Thr Ala Glu Thr Ser Pro Ser Gly Asn Ile His Gly Met Pro Leu Ala
    130                 135                 140

Ala Ser Leu Gly Phe Gly His Pro Ala Leu Thr Gln Ile Gly Gly Tyr
145                 150                 155                 160

Cys Pro Lys Ile Lys Pro Glu His Val Val Leu Ile Gly Val Arg Ser
                165                 170                 175

Leu Asp Glu Gly Glu Lys Lys Phe Ile Arg Glu Lys Gly Ile Lys Ile
            180                 185                 190

Tyr Thr Met His Glu Val Asp Arg Leu Gly Met Thr Arg Val Met Glu
        195                 200                 205

Glu Thr Ile Ala Tyr Leu Lys Glu Arg Thr Asp Gly Val His Leu Ser
    210                 215                 220

Leu Asp Leu Asp Gly Leu Asp Pro Ser Asp Ala Pro Gly Val Gly Thr
225                 230                 235                 240

Pro Val Ile Gly Gly Leu Thr Tyr Arg Glu Ser His Leu Ala Met Glu
                245                 250                 255

Met Leu Ala Glu Ala Gln Ile Ile Thr Ser Ala Glu Phe Val Glu Val
            260                 265                 270

Asn Pro Ile Leu Asp Glu Arg Asn Lys Thr Ala Ser Val Ala Val Ala
        275                 280                 285

Leu Met Gly Ser Leu Phe Gly Glu Lys Leu Met His His His His His
    290                 295                 300

His
305

<210> SEQ ID NO 17
<211> LENGTH: 24
<212> TYPE: DNA
<213> ORGANISM: artificial sequence
<220> FEATURE:
<223> OTHER INFORMATION: Primer

<400> SEQUENCE: 17
gatatacata tgcatcacca tcac                                              24

<210> SEQ ID NO 18
<211> LENGTH: 36
<212> TYPE: DNA
<213> ORGANISM: artificial sequence
<220> FEATURE:
<223> OTHER INFORMATION: Primer

<400> SEQUENCE: 18
agtgcaggat ccttacttag gtgggttaag gtagtc                                 36

<210> SEQ ID NO 19
<211> LENGTH: 27
<212> TYPE: DNA
<213> ORGANISM: artificial sequence
```

-continued

```
<220> FEATURE:
<223> OTHER INFORMATION: Primer

<400> SEQUENCE: 19
gggtgactcc ctctatatct gccaagg                                          27

<210> SEQ ID NO 20
<211> LENGTH: 27
<212> TYPE: DNA
<213> ORGANISM: artificial sequence
<220> FEATURE:
<223> OTHER INFORMATION: Primer

<400> SEQUENCE: 20
ccttggcaga tatagaggga gtcaccc                                          27

<210> SEQ ID NO 21
<211> LENGTH: 29
<212> TYPE: DNA
<213> ORGANISM: artificial sequence
<220> FEATURE:
<223> OTHER INFORMATION: Primer

<400> SEQUENCE: 21
gcaataacct tggcttcttt cggacttgc                                        29

<210> SEQ ID NO 22
<211> LENGTH: 29
<212> TYPE: DNA
<213> ORGANISM: artificial sequence
<220> FEATURE:
<223> OTHER INFORMATION: Primer

<400> SEQUENCE: 22
gcaagtccga agaagccaa ggttattgc                                         29

<210> SEQ ID NO 23
<211> LENGTH: 322
<212> TYPE: PRT
<213> ORGANISM: Capra hircus

<400> SEQUENCE: 23

Met Ser Ser Lys Pro Gln Ser Ile Gly Val Ile Gly Ala Pro Phe Ser
1               5                   10                  15

Lys Gly Gln Pro Arg Gly Gly Val Glu Glu Gly Pro Thr Val Leu Arg
                20                  25                  30

Lys Ala Gly Leu Leu Glu Lys Leu Lys Glu Leu Glu Cys Asp Val Lys
            35                  40                  45

Asp Tyr Gly Asp Leu Ser Phe Ala Asp Asn Leu Asp Asp Ser Pro Phe
        50                  55                  60

Gln Met Val Lys Asn Pro Arg Cys Val Gly Lys Ala Asn Glu Lys Leu
65                  70                  75                  80

Ala Asp Val Val Ala Glu Val Lys Lys Thr Gly Arg Ile Ser Leu Val
                85                  90                  95

Leu Gly Gly Asp His Ser Met Ala Ile Gly Ser Ile Ser Gly His Ala
                100                 105                 110

Arg Val His Pro Asp Leu Cys Val Ile Trp Val Asp Ala His Thr Asp
            115                 120                 125

Ile Asn Thr Pro Leu Thr Thr Ala Ser Gly Asn Leu His Gly Gln Pro
        130                 135                 140

Val Ser Phe Leu Leu Lys Glu Leu Lys Glu Lys Met Pro Glu Val Pro
```

```
                145                 150                 155                 160
Gly Phe His Trp Leu Ala Pro Cys Ile Ser Ala Lys Asp Ile Val Tyr
                165                 170                 175
Ile Gly Leu Arg Asp Val Asp Pro Gly Glu His Tyr Ile Leu Lys Thr
                180                 185                 190
Leu Gly Ile Lys Tyr Phe Ser Met Thr Glu Val Asp Lys Leu Gly Ile
                195                 200                 205
Gly Lys Val Met Glu Glu Thr Phe Ser Tyr Leu Leu Gly Arg Lys Lys
                210                 215                 220
Arg Pro Ile His Leu Ser Phe Asp Val Asp Gly Leu Asp Pro Ser Phe
225                 230                 235                 240
Thr Pro Ala Thr Gly Thr Pro Val Gln Gly Gly Leu Thr Tyr Arg Glu
                245                 250                 255
Gly Leu Tyr Ile Thr Glu Glu Ile Tyr Lys Thr Gly Leu Leu Ser Gly
                260                 265                 270
Leu Asp Ile Met Glu Val Asn Pro Ser Leu Gly Lys Thr Pro Glu Glu
                275                 280                 285
Val Thr Arg Thr Val Asn Thr Thr Val Ala Ile Thr Met Ala Cys Phe
                290                 295                 300
Gly Val Ala Arg Glu Gly Asn His Lys Pro Ile Asp Tyr Leu Arg Pro
305                 310                 315                 320
Pro Lys

<210> SEQ ID NO 24
<211> LENGTH: 319
<212> TYPE: PRT
<213> ORGANISM: Heterocephalus glaber

<400> SEQUENCE: 24

Met Val Arg Ala Gln Thr Glu Val Phe Ser Phe Leu Ile Ile Gln Pro
1                   5                   10                  15
Arg Gly Gly Val Glu Lys Gly Pro Ser Ala Leu Arg Tyr Ala Gly Leu
                20                  25                  30
Leu Glu Lys Leu Lys Glu Gln Glu Cys Asp Val Gln Asp Tyr Gly Asp
                35                  40                  45
Leu Ser Phe Thr Asp Val Pro Asn Asp Ala Pro Phe Gly Ile Met Lys
                50                  55                  60
Asn Pro Arg Thr Val Gly Lys Ala Thr Glu Glu Leu Ala His Met Val
65                  70                  75                  80
Ala Lys Val Gln Lys Ser Gly Arg Val Ser Leu Val Leu Gly Gly Asp
                85                  90                  95
His Ser Leu Ala Ile Gly Thr Ile Ser Gly His Ala Arg Val His Pro
                100                 105                 110
Asp Leu Gly Val Ile Trp Val Asp Ala His Thr Asp Ile Asn Thr Pro
                115                 120                 125
Met Thr Thr Thr Thr Gly Asn Met His Gly Gln Pro Val Ser Phe Leu
                130                 135                 140
Leu Lys Glu Leu Lys Gly Lys Met Pro Asp Val Pro Gly Phe Ser Trp
145                 150                 155                 160
Leu Thr Pro Cys Leu Ser Ala Lys Asp Ile Val Tyr Ile Gly Leu Arg
                165                 170                 175
Asp Val Asp Pro Gly Glu His His Ile Val Lys Thr Leu Gly Ile Lys
                180                 185                 190
Tyr Phe Ser Met Thr Glu Val Asp Arg Leu Gly Ile Gly Lys Val Met
```

```
                195                 200                 205
Glu Glu Ala Leu Ala Tyr Leu Leu Gly Arg Lys Lys Arg Pro Ile His
210                 215                 220
Leu Ser Phe Asp Val Asp Gly Leu Asp Pro Ser Ile Thr Pro Ala Thr
225                 230                 235                 240
Gly Thr Pro Val Val Gly Leu Ser His Arg Glu Gly Ile Tyr Ile
                245                 250                 255
Thr Glu Glu Ile Tyr Lys Thr Gly Leu Leu Ser Gly Leu Asp Ile Met
                260                 265                 270
Glu Val Asn Pro Val Leu Gly Lys Thr Pro Glu Glu Val Thr Arg Thr
                275                 280                 285
Val Asn Thr Ala Val Ala Val Thr Leu Ala Cys Phe Gly Val Ala Arg
            290                 295                 300
Glu Gly Asn His Asp Ser Thr Lys Asp Tyr Leu Ser Pro Pro Lys
305                 310                 315

<210> SEQ ID NO 25
<211> LENGTH: 322
<212> TYPE: PRT
<213> ORGANISM: Bos taurus

<400> SEQUENCE: 25

Met Ser Ser Lys Pro Gln Ser Ile Gly Val Ile Gly Ala Pro Phe Ser
1               5                   10                  15
Lys Gly Gln Pro Arg Gly Gly Val Glu Glu Gly Pro Thr Val Leu Arg
                20                  25                  30
Lys Ala Gly Leu Leu Glu Lys Leu Lys Glu Leu Glu Cys Asp Val Lys
            35                  40                  45
Asp Tyr Gly Asp Leu Ser Phe Ala Asp Asn Leu Asp Asp Ser Pro Phe
        50                  55                  60
Gln Ile Val Lys Asn Pro Arg Cys Val Gly Lys Ala Ser Glu Lys Leu
65                  70                  75                  80
Ala Asp Val Val Ala Glu Val Lys Lys Thr Gly Arg Ile Ser Leu Val
                85                  90                  95
Leu Gly Gly Asp His Ser Leu Ala Ile Gly Ser Ile Ser Gly His Ala
                100                 105                 110
Arg Val His Pro Asp Leu Cys Val Ile Trp Val Asp Ala His Thr Asp
            115                 120                 125
Ile Asn Thr Pro Leu Thr Thr Lys Thr Gly Asn Leu His Gly Gln Pro
        130                 135                 140
Val Ser Phe Leu Leu Lys Glu Leu Lys Glu Lys Met Pro Glu Val Pro
145                 150                 155                 160
Gly Phe Tyr Trp Val Ala Pro Cys Ile Ser Ala Lys Asp Ile Val Tyr
                165                 170                 175
Ile Gly Leu Arg Asp Val Asp Pro Gly Glu His Tyr Ile Leu Lys Thr
                180                 185                 190
Leu Gly Ile Lys Tyr Phe Ser Met Thr Glu Val Asp Lys Leu Gly Ile
            195                 200                 205
Gly Lys Val Met Glu Glu Thr Phe Ser Tyr Leu Leu Gly Arg Lys Lys
        210                 215                 220
Arg Pro Ile His Leu Ser Phe Asp Val Asp Gly Leu Asp Pro Ser Phe
225                 230                 235                 240
Thr Pro Ala Thr Gly Thr Pro Val Gln Gly Gly Leu Thr Tyr Arg Glu
                245                 250                 255
```

```
Gly Leu Tyr Ile Thr Glu Glu Ile Tyr Lys Thr Gly Leu Leu Ser Gly
                260                 265                 270

Leu Asp Ile Met Glu Val Asn Pro Ser Leu Gly Lys Thr Pro Glu Glu
            275                 280                 285

Val Thr Arg Thr Val Asn Thr Thr Val Ala Ile Thr Met Ala Cys Phe
        290                 295                 300

Gly Val Ala Arg Glu Gly Asn His Lys Pro Ile Asp Tyr Leu Ser Pro
305                 310                 315                 320

Pro Lys

<210> SEQ ID NO 26
<211> LENGTH: 322
<212> TYPE: PRT
<213> ORGANISM: Sus scrofa

<400> SEQUENCE: 26

Met Ser Phe Lys Ser Gln Ser Ile Gly Ile Gly Ala Pro Phe Ser
1               5                   10                  15

Lys Gly Gln Pro Arg Gly Gly Val Glu Glu Gly Pro Thr Ala Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Cys Phe Ala Asp Val Pro Asn Asp Thr Pro Phe
    50                  55                  60

Gln Ile Val Lys Asn Pro Arg Ser Val Gly Lys Ala Asn Gln Gln Leu
65                  70                  75                  80

Ala Asp Val Val Ala Glu Ile Lys Lys Asn Gly Arg Thr Ser Leu Val
                85                  90                  95

Leu Gly Gly Asp His Ser Met Ala Ile Gly Ser Ile Ser Gly His Ala
            100                 105                 110

Arg Val His Pro Asp Leu Cys Val Ile Trp Val Asp Ala His Thr Asp
        115                 120                 125

Ile Asn Thr Pro Leu Thr Thr Thr Gly Asn Leu His Gly Gln Pro
    130                 135                 140

Val Ser Phe Leu Leu Lys Glu Leu Lys Glu Lys Ile Pro Glu Val Pro
145                 150                 155                 160

Gly Leu Ser Trp Val Thr Pro Cys Leu Ser Ala Lys Asp Ile Val Tyr
                165                 170                 175

Ile Gly Leu Arg Asp Val Asp Pro Ala Glu His Tyr Ile Leu Lys Thr
            180                 185                 190

Leu Gly Ile Lys Tyr Phe Ser Met Ile Glu Val Asp Lys Leu Gly Ile
        195                 200                 205

Gly Lys Val Met Glu Glu Ala Phe Ser Tyr Leu Leu Gly Arg Lys Lys
    210                 215                 220

Arg Pro Ile His Leu Ser Phe Asp Val Asp Gly Leu Asp Pro Phe Phe
225                 230                 235                 240

Thr Pro Ala Thr Gly Thr Pro Val His Gly Gly Leu Ser Tyr Arg Glu
                245                 250                 255

Gly Ile Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Leu Val Leu Ala Cys Phe
    290                 295                 300
```

```
Gly Val Ala Arg Glu Gly Asn His Lys Pro Ile Asp Tyr Leu Lys Pro
305                 310                 315                 320

Pro Lys

<210> SEQ ID NO 27
<211> LENGTH: 199
<212> TYPE: PRT
<213> ORGANISM: Plecoglossus altivelis

<400> SEQUENCE: 27

Leu Gln Phe Ala Phe Arg Ile Tyr Lys Arg Ser His His Ser Val
1               5                   10                  15

Gly Ile Ile Gly Ala Pro Phe Ser Lys Gly Gln Pro Arg Asp Gly Val
                20                  25                  30

Glu Arg Gly Pro Asp Leu Ile Arg Ser Ala Gly Leu Val Glu Lys Leu
            35                  40                  45

Lys Ala Gln Gly Cys Asp Val Lys Asp Tyr Gly Asn Leu Thr Phe Glu
    50                  55                  60

Glu Phe Ser Ser Asp Glu Pro Ile Gly Arg Val Lys Arg Pro Arg Ala
65                  70                  75                  80

Val Gly Arg Ala Asn Glu Arg Leu Ala Gly Ala Val Asp Glu Val Lys
                85                  90                  95

Lys Glu Gly Arg Thr Cys Val Met Leu Gly Gly Asp His Ser Leu Ala
            100                 105                 110

Ile Gly Ser Ile His Gly His Ala Ala Ala Gln Lys Gly Leu Ser Val
        115                 120                 125

Val Trp Val Asp Ala His Ala Asp Ile Asn Thr Pro Leu Thr Ser Pro
    130                 135                 140

Thr Gly Asn Ile His Glu Gln Pro Met Ser Tyr Leu Ile Gln Glu Leu
145                 150                 155                 160

His Ser Lys Ile Pro Val Met Pro Asn Phe Ser Trp Ile Lys Pro Cys
                165                 170                 175

Ile Ser Ala Lys Asp Val Val Tyr Ile Gly Leu Arg Asp Val Asp Pro
            180                 185                 190

Glu Glu His Tyr Ile Leu Lys
        195

<210> SEQ ID NO 28
<211> LENGTH: 337
<212> TYPE: PRT
<213> ORGANISM: Salmo salar

<400> SEQUENCE: 28

Met Val Ile Met Lys Ser Ser Gly Gly Leu Gln Leu Ala Phe Arg Ile
1               5                   10                  15

Tyr Lys Arg Ser His His Ser Val Gly Ile Ile Gly Ala Pro Phe Ser
                20                  25                  30

Lys Gly Gln Pro Arg Asp Gly Val Glu Lys Gly Pro Asp Leu Ile Arg
            35                  40                  45

Ala Ala Gly Leu Val Lys Lys Leu Lys Ala Gln Gly Cys Ala Val Lys
    50                  55                  60

Asp Tyr Gly Asn Val Thr Phe Glu Glu Val Ala Asn Asp Glu Pro Ile
65                  70                  75                  80

Gly Asn Val Lys Arg Pro Arg Ala Val Gly Ser Ala Asn Gln Arg Leu
                85                  90                  95

Ser Ala Ala Val His Ala Val Lys Asn Asp Gly His Thr Cys Val Met
```

```
                100                 105                 110
Leu Gly Gly Gly His Ser Leu Ala Ile Gly Ser Ile Gln Gly His Ala
            115                 120                 125

Ala Ala Lys Lys Asp Leu Ser Val Val Trp Val Asp Ala His Ala Asp
130                 135                 140

Ile Asn Thr Pro Leu Thr Ser Pro Thr Gly Asn Ile His Gly Gln Pro
145                 150                 155                 160

Met Ser Tyr Leu Ile His Glu Leu Gln Ser Lys Ile Pro Val Leu Pro
                165                 170                 175

Asn Phe Ser Trp Ile Lys Pro Cys Val Ser Ala Lys Asp Ile Val Tyr
            180                 185                 190

Ile Gly Leu Arg Asp Val Asp Pro Glu Glu His Ile Leu Lys Leu
        195                 200                 205

Leu Gly Ile Glu Val Tyr Ser Met Thr Glu Val Asp Arg Leu Gly Ile
210                 215                 220

Ala Lys Val Met Glu Glu Thr Cys Asp Tyr Ile Phe Ser Lys Val Lys
225                 230                 235                 240

Lys Pro Ile His Leu Ser Tyr Asp Ile Asp Ala Leu Asp Pro Ser Ile
                245                 250                 255

Ser Pro Ala Thr Gly Thr Pro Val Val Gly Gly Leu Thr Tyr Arg Glu
            260                 265                 270

Gly Ile Tyr Ile Thr Glu His Ile Cys Gln Thr Gly Leu Leu Ser Ala
        275                 280                 285

Val Asp Met Val Glu Val Asn Pro Lys Arg Gly Arg Thr Glu Asp Glu
290                 295                 300

Ile Ser Ser Thr Val Asn Ala Ala Val Asp Leu Ile Arg Gly Cys Phe
305                 310                 315                 320

Gly Lys Leu Arg Glu Gly Asn His Pro Ala Asp Tyr Lys Met Pro Leu
                325                 330                 335

Pro

<210> SEQ ID NO 29
<211> LENGTH: 338
<212> TYPE: PRT
<213> ORGANISM: Oncorhynchus mykiss

<400> SEQUENCE: 29

Met Val Leu Ile Lys Ser Ser Arg Gly Leu Gln Leu Ala Phe Arg Thr
1               5                   10                  15

Tyr Lys Arg Ser His His His Ser Val Gly Ile Ile Gly Ala Pro Phe
            20                  25                  30

Ser Lys Gly Gln Pro Arg Asp Gly Val Glu Lys Gly Pro Asp Leu Ile
        35                  40                  45

Arg Ser Ala Gly Leu Val Glu Lys Leu Arg Ala Gln Gly Cys Ala Val
    50                  55                  60

Lys Asp Tyr Gly Asn Val Thr Phe Glu Glu Val Ala Asn Asp Glu Pro
65                  70                  75                  80

Ile Gly Asn Val Lys Arg Pro Arg Ala Val Gly Ser Ala Asn Gln Arg
                85                  90                  95

Leu Ser Ala Ala Val His Ala Val Lys Asn Asp Gly His Thr Cys Val
            100                 105                 110

Met Leu Gly Gly Asp His Ser Leu Ala Ile Gly Ser Ile Gln Gly His
        115                 120                 125

Ala Ala Ala Lys Lys Asp Leu Cys Val Val Trp Val Asp Ala His Ala
```

```
                130               135                 140
Asp Ile Asn Thr Pro Leu Thr Ser Pro Thr Gly Asn Ile His Gly Gln
145                 150                 155                 160

Pro Met Ser Tyr Leu Ile His Glu Leu His Ser Lys Ile Pro Val Leu
                165                 170                 175

Pro Asn Phe Ser Trp Ile Lys Pro Cys Val Ser Ala Lys Asp Ile Val
                180                 185                 190

Tyr Ile Gly Leu Arg Asp Val Asp Pro Glu Glu His His Ile Leu Thr
                195                 200                 205

Leu Leu Gly Val Lys Gly Tyr Ser Met Thr Glu Val Asp Arg Leu Gly
                210                 215                 220

Ile Ser Lys Val Met Glu Glu Thr Cys Asp Tyr Ile Phe Ser Lys Val
225                 230                 235                 240

Lys Lys Pro Ile His Leu Ser Tyr Asp Ile Asp Ala Leu Asp Pro Ser
                245                 250                 255

Ile Ser Pro Ala Thr Gly Thr Pro Val Val Gly Gly Leu Thr Tyr Arg
                260                 265                 270

Glu Gly Val Tyr Ile Thr Glu His Ile Cys Gln Thr Gly Met Leu Ser
                275                 280                 285

Ala Val Asp Met Val Glu Val Asn Pro Lys Arg Gly Lys Thr Glu Glu
                290                 295                 300

Glu Ile Ser Ser Thr Val Asn Thr Ala Val Asp Leu Ile Arg Gly Cys
305                 310                 315                 320

Phe Gly Lys Leu Arg Glu Gly Asn His Pro Ala Asp Tyr Lys Met Pro
                325                 330                 335

Leu Pro

<210> SEQ ID NO 30
<211> LENGTH: 335
<212> TYPE: PRT
<213> ORGANISM: Osmerus mordax

<400> SEQUENCE: 30

Met Lys Ser Thr Arg Gly Leu Gln Leu Ala Phe Arg Ile Tyr Lys Arg
1               5                   10                  15

Ser His His Ser Val Gly Ile Ile Gly Ala Pro Phe Ser Lys Gly
                20                  25                  30

Gln Pro Arg Asp Gly Val Glu Arg Gly Pro Asp Leu Ile Arg Ser Ala
                35                  40                  45

Gly Leu Val Glu Lys Leu Lys Ala Gln Gly Cys Asp Val Lys Asp Tyr
                50                  55                  60

Gly Asn Leu Met Phe Glu Glu Phe Ser Ser Asp Glu Pro Ile Ser Arg
65                  70                  75                  80

Val Lys Arg Pro Arg Ala Val Gly Arg Ala Asn Glu Arg Leu Ala Gly
                85                  90                  95

Ala Val Glu Glu Val Lys Lys Gly Arg Thr Cys Val Met Leu Gly
                100                 105                 110

Gly Asp His Ser Leu Ala Ile Gly Ser Ile His Gly His Ala Ala Ala
                115                 120                 125

Gln Lys Asp Leu Ser Val Val Trp Val Asp Ala His Ala Asp Ile Asn
                130                 135                 140

Thr Pro Leu Thr Ser Pro Thr Gly Asn Val His Gly Gln Pro Met Ser
145                 150                 155                 160

Tyr Leu Ile Arg Glu Leu His Ser Lys Ile Pro Val Ile Pro Asn Phe
```

```
            165                 170                 175
Ser Trp Ile Lys Pro Cys Val Ser Ala Lys Asp Val Val Tyr Ile Gly
            180                 185                 190

Leu Arg Asp Val Asp Pro Glu Glu His Tyr Ile Leu Lys Tyr Leu Gly
            195                 200                 205

Ile Lys Val Phe Ser Met Thr Asp Val Asp His Leu Gly Ile Ala Arg
            210                 215                 220

Val Met Glu Glu Thr Cys Asp His Met Phe Ser Lys Val Lys Lys Pro
225                 230                 235                 240

Ile His Leu Ser Tyr Asp Ile Asp Ala Leu Asp Pro Ser Ile Ser Pro
            245                 250                 255

Ala Thr Gly Thr Pro Val Ile Gly Gly Leu Thr Tyr Arg Glu Gly Val
            260                 265                 270

Tyr Val Thr Glu His Ile Cys Gln Thr Gly Leu Leu Ser Ala Leu Asp
            275                 280                 285

Met Val Glu Val Asn Pro Lys Arg Gly Lys Thr Glu Glu Val Arg
            290                 295                 300

Ser Thr Val Ser Ala Ala Val Asp Leu Val Leu Gly Cys Phe Gly Arg
305                 310                 315                 320

Leu Arg Glu Gly Asn His Arg Ala Asp Tyr Arg Met Pro Glu Pro
            325                 330                 335

<210> SEQ ID NO 31
<211> LENGTH: 335
<212> TYPE: PRT
<213> ORGANISM: Hyriopsis cumingii

<400> SEQUENCE: 31

Met Pro Gly Ser Val Glu Gln Met Lys Met Lys Ser Ala Glu Arg Ile
1               5                   10                  15

Gly Val Leu Gly Ile Pro Phe Ser Lys Gly Gln Ser Arg Val Gly Thr
            20                  25                  30

Glu Tyr Gly Pro Glu Val Leu Arg Asn Gly Gly Ile Val Arg Lys Leu
            35                  40                  45

Gln Asn Leu Gly Cys His Val Gln Asp His Gly Asp Val Glu Val Ile
        50                  55                  60

Gln Val Glu Lys Asp Asp Pro Glu Glu Asn Ala Lys Asn Pro Arg Thr
65                  70                  75                  80

Val Gly Leu Thr Ser Lys Leu Ile Ala Asp Lys Val Glu Arg Val Leu
                85                  90                  95

Arg Ser Glu Asp Ile Cys Leu Gly Leu Gly Gly Asp His Ser Val Ala
            100                 105                 110

Ile Gly Thr Ile Ala Gly Asn Ala Arg Val Glu Pro Asp Leu Val Val
            115                 120                 125

Leu Trp Ile Asp Ala His Ala Asp Ile Asn Thr Pro Met Thr Ser Asp
        130                 135                 140

Ser Gly Asn Ile His Gly Met Pro Leu Ala Phe Leu Val Arg Glu Leu
145                 150                 155                 160

Glu Ser Tyr Val Thr Lys Leu Pro Gly Phe Glu Trp Leu Ser Pro Cys
                165                 170                 175

Ile His Ala Lys Asp Ile Ala Tyr Ile Gly Leu Arg Asp Val Asp Ala
            180                 185                 190

Gly Glu Arg Lys Ile Ile Glu Lys Phe Gly Ile Thr Ala Phe Ser Met
            195                 200                 205
```

Gln Glu Val Asp Lys Tyr Gly Ile Asn Glu Val Val Glu Arg Ala Leu
            210                 215                 220

Arg Ala Val Asp Pro Glu Gly Lys Arg Pro Ile His Leu Ser Phe Asp
225                 230                 235                 240

Val Asp Ala Met Asp Pro Thr Leu Ala Thr Ser Ala Arg Asp His Ala
                245                 250                 255

Val Ile Gly Gly Leu Ser Leu Arg Glu Thr Tyr Tyr Ile Ala Glu Glu
            260                 265                 270

Val Ala Arg Thr Gly Arg Leu Ser Met Val Asp Val Ala Glu Val Asn
            275                 280                 285

Pro Leu Leu Gly Asp Glu Lys Asp Lys Lys Leu Thr Val Asp Met Thr
290                 295                 300

Ile Ser Val Ile Gln Arg Phe Phe Gly Asn Arg Arg Gly Gly Cys Tyr
305                 310                 315                 320

Pro Pro Gly Tyr Asp Ile Pro Leu Pro His Lys Leu Met Thr Arg
                325                 330                 335

<210> SEQ ID NO 32
<211> LENGTH: 354
<212> TYPE: PRT
<213> ORGANISM: Rattus norvegicus

<400> SEQUENCE: 32

Met Phe Leu Arg Ser Ser Val Ser Arg Leu Leu His Gly Gln Ile Pro
1               5                   10                  15

Cys Ala Leu Thr Arg Ser Val His Ser Val Ala Val Val Gly Ala Pro
            20                  25                  30

Phe Ser Arg Gly Gln Lys Lys Lys Gly Val Glu Tyr Gly Pro Ala Ala
        35                  40                  45

Ile Arg Glu Ala Gly Leu Leu Lys Arg Leu Ser Met Leu Gly Cys His
    50                  55                  60

Leu Lys Asp Phe Gly Asp Leu Ser Phe Thr Asn Val Pro Lys Asp Asp
65                  70                  75                  80

Pro Tyr Asn Asn Leu Val Val Tyr Pro Arg Ser Val Gly Ile Ala Asn
                85                  90                  95

Gln Glu Leu Ala Glu Val Val Ser Arg Ala Val Ser Gly Gly Tyr Ser
            100                 105                 110

Cys Val Thr Met Gly Gly Asp His Ser Leu Ala Ile Gly Thr Ile Ile
        115                 120                 125

Gly His Ala Arg His His Pro Asp Leu Cys Val Ile Trp Val Asp Ala
    130                 135                 140

His Ala Asp Ile Asn Thr Pro Leu Thr Thr Val Ser Gly Asn Ile His
145                 150                 155                 160

Gly Gln Pro Leu Ser Phe Leu Ile Arg Glu Leu Gln Asp Lys Val Pro
                165                 170                 175

Gln Leu Pro Gly Phe Ser Trp Ile Lys Pro Cys Leu Ser Pro Pro Asn
            180                 185                 190

Ile Val Tyr Ile Gly Leu Arg Asp Val Glu Pro Ala Glu His Phe Ile
        195                 200                 205

Leu Lys Ser Phe Asp Ile Gln Tyr Phe Ser Met Arg Asp Ile Asp Arg
    210                 215                 220

Leu Gly Ile Gln Lys Val Met Glu Gln Thr Phe Asp Arg Leu Ile Gly
225                 230                 235                 240

Lys Arg Lys Arg Pro Ile His Leu Ser Phe Asp Ile Asp Ala Phe Asp
                245                 250                 255

```
Pro Lys Leu Ala Pro Ala Thr Gly Thr Pro Val Val Gly Gly Leu Thr
            260                 265                 270

Tyr Arg Glu Gly Leu Tyr Ile Thr Glu Glu Ile His Ser Thr Gly Leu
            275                 280                 285

Leu Ser Ala Leu Asp Leu Val Glu Val Asn Pro His Leu Ala Thr Ser
            290                 295                 300

Glu Glu Glu Ala Lys Ala Thr Ala Ser Leu Ala Val Asp Val Ile Ala
305                 310                 315                 320

Ser Ser Phe Gly Gln Thr Arg Glu Gly Gly His Ile Ala Tyr Asp His
                    325                 330                 335

Leu Pro Thr Pro Ser Ser Pro His Glu Ser Glu Lys Glu Glu Cys Val
                340                 345                 350

Arg Ile

<210> SEQ ID NO 33
<211> LENGTH: 354
<212> TYPE: PRT
<213> ORGANISM: Mus musculus

<400> SEQUENCE: 33

Met Phe Leu Arg Ser Ser Ala Ser Arg Leu Leu His Gly Gln Ile Pro
1               5                   10                  15

Cys Val Leu Thr Arg Ser Val His Ser Val Ala Ile Val Gly Ala Pro
            20                  25                  30

Phe Ser Arg Gly Gln Lys Lys Leu Gly Val Glu Tyr Gly Pro Ala Ala
        35                  40                  45

Ile Arg Glu Ala Gly Leu Leu Lys Arg Leu Ser Arg Leu Gly Cys His
    50                  55                  60

Leu Lys Asp Phe Gly Asp Leu Ser Phe Thr Asn Val Pro Gln Asp Asp
65                  70                  75                  80

Pro Tyr Asn Asn Leu Val Val Tyr Pro Arg Ser Val Gly Leu Ala Asn
                85                  90                  95

Gln Glu Leu Ala Glu Val Val Ser Arg Ala Val Ser Gly Gly Tyr Ser
            100                 105                 110

Cys Val Thr Met Gly Gly Asp His Ser Leu Ala Ile Gly Thr Ile Ile
        115                 120                 125

Gly His Ala Arg His Arg Pro Asp Leu Cys Val Ile Trp Val Asp Ala
    130                 135                 140

His Ala Asp Ile Asn Thr Pro Leu Thr Thr Val Ser Gly Asn Ile His
145                 150                 155                 160

Gly Gln Pro Leu Ser Phe Leu Ile Lys Glu Leu Gln Asp Lys Val Pro
                165                 170                 175

Gln Leu Pro Gly Phe Ser Trp Ile Lys Pro Cys Leu Ser Pro Pro Asn
            180                 185                 190

Ile Val Tyr Ile Gly Leu Arg Asp Val Glu Pro Pro Glu His Phe Ile
        195                 200                 205

Leu Lys Asn Tyr Asp Ile Gln Tyr Phe Ser Met Arg Glu Ile Asp Arg
    210                 215                 220

Leu Gly Ile Gln Lys Val Met Glu Gln Thr Phe Asp Arg Leu Ile Gly
225                 230                 235                 240

Lys Arg Gln Arg Pro Ile His Leu Ser Phe Asp Ile Asp Ala Phe Asp
                245                 250                 255

Pro Lys Leu Ala Pro Ala Thr Gly Thr Pro Val Val Gly Gly Leu Thr
            260                 265                 270
```

Tyr Arg Glu Gly Val Tyr Ile Thr Glu Glu Ile His Asn Thr Gly Leu
            275                 280                 285

Leu Ser Ala Leu Asp Leu Val Glu Val Asn Pro His Leu Ala Thr Ser
290                 295                 300

Glu Glu Glu Ala Lys Ala Thr Ala Arg Leu Ala Val Asp Val Ile Ala
305                 310                 315                 320

Ser Ser Phe Gly Gln Thr Arg Glu Gly Gly His Ile Val Tyr Asp His
            325                 330                 335

Leu Pro Thr Pro Ser Ser Pro His Glu Ser Glu Asn Glu Glu Cys Val
            340                 345                 350

Arg Ile

<210> SEQ ID NO 34
<211> LENGTH: 354
<212> TYPE: PRT
<213> ORGANISM: Homo sapiens

<400> SEQUENCE: 34

Met Ser Leu Arg Gly Ser Leu Ser Arg Leu Leu Gln Thr Arg Val His
1               5                   10                  15

Ser Ile Leu Lys Lys Ser Val His Ser Val Ala Val Ile Gly Ala Pro
            20                  25                  30

Phe Ser Gln Gly Gln Lys Arg Lys Gly Val Glu His Gly Pro Ala Ala
        35                  40                  45

Ile Arg Glu Ala Gly Leu Met Lys Arg Leu Ser Ser Leu Gly Cys His
50                  55                  60

Leu Lys Asp Phe Gly Asp Leu Ser Phe Thr Pro Val Pro Lys Asp Asp
65                  70                  75                  80

Leu Tyr Asn Asn Leu Ile Val Asn Pro Arg Ser Val Gly Leu Ala Asn
                85                  90                  95

Gln Glu Leu Ala Glu Val Val Ser Arg Ala Val Ser Asp Gly Tyr Ser
            100                 105                 110

Cys Val Thr Leu Gly Gly Asp His Ser Leu Ala Ile Gly Thr Ile Ser
        115                 120                 125

Gly His Ala Arg His Cys Pro Asp Leu Cys Val Val Trp Val Asp Ala
130                 135                 140

His Ala Asp Ile Asn Thr Pro Leu Thr Thr Ser Ser Gly Asn Leu His
145                 150                 155                 160

Gly Gln Pro Val Ser Phe Leu Leu Arg Glu Leu Gln Asp Lys Val Pro
                165                 170                 175

Gln Leu Pro Gly Phe Ser Trp Ile Lys Pro Cys Ile Ser Ser Ala Ser
            180                 185                 190

Ile Val Tyr Ile Gly Leu Arg Asp Val Asp Pro Glu His Phe Ile
        195                 200                 205

Leu Lys Asn Tyr Asp Ile Gln Tyr Phe Ser Met Arg Asp Ile Asp Arg
210                 215                 220

Leu Gly Ile Gln Lys Val Met Glu Arg Thr Phe Asp Leu Leu Ile Gly
225                 230                 235                 240

Lys Arg Gln Arg Pro Ile His Leu Ser Phe Asp Ile Asp Ala Phe Asp
                245                 250                 255

Pro Thr Leu Ala Pro Ala Thr Gly Thr Pro Val Val Gly Gly Leu Thr
            260                 265                 270

Tyr Arg Glu Gly Met Tyr Ile Ala Glu Glu Ile His Asn Thr Gly Leu
        275                 280                 285

```
Leu Ser Ala Leu Asp Leu Val Glu Val Asn Pro Gln Leu Ala Thr Ser
        290                 295                 300

Glu Glu Glu Ala Lys Thr Thr Ala Asn Leu Ala Val Asp Val Ile Ala
305                 310                 315                 320

Ser Ser Phe Gly Gln Thr Arg Glu Gly Gly His Ile Val Tyr Asp Gln
                325                 330                 335

Leu Pro Thr Pro Ser Ser Pro Asp Glu Ser Glu Asn Gln Ala Arg Val
                340                 345                 350

Arg Ile
```

<210> SEQ ID NO 35
<211> LENGTH: 354
<212> TYPE: PRT
<213> ORGANISM: Bos taurus

<400> SEQUENCE: 35

```
Met Ser Leu Arg Ser His Leu Ser Arg Leu Leu Arg Thr Gln Val His
1               5                   10                  15

Ser Val Arg Lys Lys Ser Val His Ser Val Ala Val Ile Gly Ala Pro
            20                  25                  30

Phe Ser Gln Gly Gln Lys Arg Lys Gly Val Glu Tyr Gly Pro Ala Ala
        35                  40                  45

Val Arg Glu Ala Gly Leu Met Lys Arg Leu Ser Asp Leu Gly Cys His
    50                  55                  60

Leu Lys Asp Phe Gly Asp Leu Asn Phe Thr Pro Val Pro Lys Asp Asp
65                  70                  75                  80

Leu Tyr Asn Asn Leu Ile Val Asn Pro Arg Ser Val Gly Leu Ala Asn
                85                  90                  95

Gln Glu Leu Ala Glu Val Val Ser Arg Ala Val Ser Gly Gly Tyr Ser
            100                 105                 110

Cys Val Thr Val Gly Gly Asp His Ser Leu Ala Ile Gly Thr Ile Ser
        115                 120                 125

Gly His Ala Arg His Cys Pro Asp Leu Gly Val Ile Trp Val Asp Ala
    130                 135                 140

His Ala Asp Ile Asn Thr Pro Leu Thr Thr Ser Ser Gly Asn Leu His
145                 150                 155                 160

Gly Gln Pro Val Ser Phe Leu Leu Arg Glu Leu Gln Asp Lys Val Pro
                165                 170                 175

Gln Leu Pro Gly Phe Ser Trp Ile Lys Pro Cys Ile Ser Ser Pro Ser
            180                 185                 190

Ile Val Tyr Ile Gly Leu Arg Asp Val Asp Pro Pro Glu His Phe Ile
        195                 200                 205

Leu Lys Asn Tyr Asp Ile Gln Tyr Phe Ser Met Arg Asp Ile Asp Arg
    210                 215                 220

Leu Gly Ile Gln Lys Val Met Glu Gln Thr Phe Asp Leu Leu Ile Gly
225                 230                 235                 240

Lys Arg Gln Arg Pro Ile His Leu Ser Phe Asp Ile Asp Ala Phe Asp
                245                 250                 255

Pro Thr Leu Ala Pro Ala Thr Gly Thr Pro Val Val Gly Gly Leu Thr
            260                 265                 270

Tyr Arg Glu Gly Ile Tyr Ile Thr Glu Glu Ile His Ser Thr Gly Leu
        275                 280                 285

Leu Ser Ala Leu Asp Leu Val Glu Val Asn Pro Arg Leu Ala Val Ser
    290                 295                 300
```

```
Glu Glu Glu Ala Lys Ala Thr Ala Ser Leu Ala Val Asp Val Ile Ala
305                 310                 315                 320

Ser Ser Phe Gly Gln Thr Arg Glu Gly Gly His Ile Val Tyr Asp Gln
                325                 330                 335

Leu Pro Thr Pro Ser Ser Pro Asp Glu Ser Glu Ser Glu Glu Arg Val
                340                 345                 350

Arg Ile

<210> SEQ ID NO 36
<211> LENGTH: 353
<212> TYPE: PRT
<213> ORGANISM: Heterocephalus glaber

<400> SEQUENCE: 36

Met Ser Leu Arg Ile Ser Leu Ser Arg Val Leu Arg Thr Gln Val Pro
1               5                   10                  15

Ser Val Leu Lys Lys Ser Val His Ser Val Ala Val Ile Gly Ala Pro
                20                  25                  30

Phe Ser Gln Gly Gln Arg Lys Lys Gly Val Glu Tyr Gly Pro Ala Ala
                35                  40                  45

Ile Arg Glu Ala Gly Leu Met Lys Arg Leu Ser Gly Leu Gly Cys Ser
50                  55                  60

Leu Lys Asp Phe Gly Asp Leu Ser Phe Thr Pro Val Ala Lys Asp Asp
65                  70                  75                  80

Pro Phe Asn Asn Leu Val Met Asn Pro Arg Ser Val Gly Leu Ala Asn
                85                  90                  95

Gln Glu Leu Thr Glu Val Val Ser Arg Ala Val Ser Asp Gly Tyr Ser
                100                 105                 110

Cys Val Thr Val Gly Gly Asp His Ser Leu Ala Ile Gly Thr Ile Ser
                115                 120                 125

Gly His Ala Arg His Cys Pro Asp Leu Cys Val Ile Trp Val Asp Ala
130                 135                 140

His Thr Asp Val Asn Thr Pro Leu Thr Thr Pro Thr Gly Asn Leu His
145                 150                 155                 160

Gly Gln Pro Val Ala Phe Leu Leu Arg Glu Leu Gln Asp Lys Ile Pro
                165                 170                 175

Ser Leu Pro Gly Phe Ser Trp Ile Lys Pro Cys Ile Ser Thr Pro Ser
                180                 185                 190

Ile Val Tyr Ile Gly Leu Arg Asp Val Asp Pro Pro Glu His Phe Ile
                195                 200                 205

Leu Lys Asn Tyr Asp Ile Gln Tyr Phe Ser Met Arg Asp Ile Asp Gln
                210                 215                 220

Leu Gly Ile Lys Lys Val Met Glu Gln Thr Phe Asp Leu Leu Ile Gly
225                 230                 235                 240

Lys Arg Gln Arg Pro Ile His Leu Ser Phe Asp Ile Asp Ala Phe Ala
                245                 250                 255

Pro Pro Leu Ala Pro Ala Thr Gly Thr Pro Val Val Gly Gly Leu Thr
                260                 265                 270

Tyr Arg Glu Gly Val Tyr Ile Ser Glu Glu Ile His Asn Thr Gly Leu
                275                 280                 285

Leu Ser Ala Leu Asp Leu Val Glu Val Asn Pro His Leu Ala Thr Ser
                290                 295                 300

Glu Glu Ala Lys Ala Thr Ala Ser Leu Ala Val Asp Val Ile Ala Ser
305                 310                 315                 320
```

```
Ser Phe Gly Gln Thr Arg Glu Gly Gly His Ile Val Tyr Asp Gln Leu
            325                 330                 335

Pro Asn Pro Ser Ser Pro Asp Glu Ser Glu Asn Glu Glu Arg Val Arg
            340                 345                 350

Ile

<210> SEQ ID NO 37
<211> LENGTH: 354
<212> TYPE: PRT
<213> ORGANISM: Pan troglodytes

<400> SEQUENCE: 37

Met Ser Leu Arg Gly Ser Leu Ser Arg Leu Leu Gln Thr Arg Val His
1               5                   10                  15

Ser Ile Leu Lys Lys Ser Val His Ser Val Ala Val Ile Gly Ala Pro
            20                  25                  30

Phe Ser Gln Gly Gln Lys Arg Lys Gly Val Glu His Gly Pro Ala Ala
            35                  40                  45

Ile Arg Glu Ala Gly Leu Met Lys Arg Leu Ser Ser Leu Gly Cys His
50                  55                  60

Leu Lys Asp Phe Gly Asp Leu Ser Phe Thr Pro Val Pro Lys Asp Asp
65                  70                  75                  80

Leu Tyr Asn Asn Leu Ile Val Asn Pro Arg Ser Val Gly Leu Ala Asn
            85                  90                  95

Gln Glu Leu Ala Glu Val Val Ser Arg Ala Val Ser Asp Gly Tyr Ser
            100                 105                 110

Cys Val Thr Leu Gly Gly Asp His Ser Leu Ala Ile Gly Thr Ile Ser
            115                 120                 125

Gly His Ala Arg His Cys Pro Asp Leu Cys Val Val Trp Val Asp Ala
130                 135                 140

His Ala Asp Ile Asn Thr Pro Leu Thr Thr Ser Ser Gly Asn Leu His
145                 150                 155                 160

Gly Gln Pro Val Ser Phe Leu Leu Arg Glu Leu Gln Asp Lys Val Pro
            165                 170                 175

Gln Leu Pro Gly Phe Ser Trp Ile Lys Pro Cys Ile Ser Ser Ala Ser
            180                 185                 190

Ile Val Tyr Ile Gly Leu Arg Asp Val Asp Pro Pro Glu His Phe Ile
            195                 200                 205

Leu Lys Asn Tyr Asp Ile Gln Tyr Phe Ser Met Arg Asp Ile Asp Arg
            210                 215                 220

Leu Gly Ile Gln Lys Val Met Glu Arg Thr Phe Asp Leu Leu Ile Gly
225                 230                 235                 240

Lys Arg Gln Arg Pro Ile His Leu Ser Phe Asp Ile Asp Ala Phe Asp
            245                 250                 255

Pro Thr Leu Ala Pro Ala Thr Gly Thr Pro Val Val Gly Gly Leu Thr
            260                 265                 270

Tyr Arg Glu Gly Met Tyr Ile Ala Glu Glu Ile His Asn Thr Gly Leu
            275                 280                 285

Leu Ser Ala Leu Asp Leu Val Glu Val Asn Pro Gln Leu Ala Thr Ser
            290                 295                 300

Glu Glu Glu Ala Lys Thr Thr Ala Asn Leu Ala Val Asp Val Ile Ala
305                 310                 315                 320

Ser Ser Phe Gly Gln Thr Arg Glu Gly Gly His Ile Val Tyr Asp Gln
            325                 330                 335
```

Leu Pro Thr Pro Ser Ser Pro Asp Glu Ser Glu Asn Gln Ala Arg Val
            340                 345                 350

Arg Ile

<210> SEQ ID NO 38
<211> LENGTH: 354
<212> TYPE: PRT
<213> ORGANISM: Oryctolagus cuniculus

<400> SEQUENCE: 38

Met Ser Tyr Gly Ser Cys Val Ser Arg Leu Leu Arg Thr Arg Val Gln
1               5                   10                  15

Ser Val Leu Lys Lys Ser Val His Ser Val Ala Val Ile Gly Ala Pro
            20                  25                  30

Phe Ser Gln Gly Gln Lys Arg Lys Gly Val Glu Cys Gly Pro Ala Ala
        35                  40                  45

Ile Arg Asp Ala Gly Leu Val Lys Arg Leu Ser Asp Leu Gly Cys Arg
50                  55                  60

Leu Lys Asp Tyr Gly Asp Leu Ser Phe Thr Pro Val Pro Lys Asp Asp
65                  70                  75                  80

Leu Tyr Asn Asn Leu Ile Val Asn Pro Arg Ser Val Gly Leu Ala Asn
                85                  90                  95

Gln Glu Leu Ala Glu Val Val Asn Arg Ala Val Ser Gly Gly Tyr Ser
            100                 105                 110

Cys Val Thr Val Gly Gly Asp His Ser Leu Ala Ile Gly Thr Ile Ser
        115                 120                 125

Gly His Ala Arg His Cys Pro Asp Leu Cys Val Val Trp Val Asp Ala
130                 135                 140

His Ala Asp Ile Asn Thr Pro Leu Thr Thr Ser Ser Gly Asn Leu His
145                 150                 155                 160

Gly Gln Pro Val Ser Phe Leu Leu Arg Glu Leu Gln Asp Lys Val Pro
                165                 170                 175

Gln Leu Pro Gly Phe Ser Trp Ile Lys Pro Cys Ile Ser Ser Pro Ser
            180                 185                 190

Ile Val Tyr Ile Gly Leu Arg Asp Val Asp Pro Pro Glu His Phe Ile
        195                 200                 205

Leu Lys Lys Tyr Asp Ile Gln Tyr Phe Ser Met Arg Asp Ile Asp Arg
210                 215                 220

Leu Gly Ile Gln Lys Val Met Glu Gln Thr Phe Asp Leu Leu Ile Gly
225                 230                 235                 240

Lys Lys Gln Arg Pro Ile His Leu Ser Phe Asp Ile Asp Ala Phe Asp
                245                 250                 255

Pro Thr Leu Ala Pro Ala Thr Gly Thr Pro Gly Cys Gly Gly Ala Asp
            260                 265                 270

Leu Ser Arg Arg Met Tyr Ile Ser Glu Glu Ile His Asn Thr Gly Leu
        275                 280                 285

Leu Ser Ala Leu Asp Leu Val Glu Val Asn Pro Arg Leu Ala Ala Ser
290                 295                 300

Asp Glu Glu Ala Lys Ala Thr Ala Ser Leu Ala Val Asp Val Ile Ala
305                 310                 315                 320

Ser Ser Phe Gly Gln Thr Arg Glu Gly Gly His Thr Val Tyr Glu Gln
                325                 330                 335

Leu Pro Pro Pro Ser Ser Pro His Glu Ser Glu Asn Ala Glu Arg Val
            340                 345                 350

Arg Ile

<210> SEQ ID NO 39
<211> LENGTH: 321
<212> TYPE: PRT
<213> ORGANISM: Delftia sp.

<400> SEQUENCE: 39

```
Met Gly Pro Met Ser Met Asn Thr His Thr Thr Pro Gln Thr Ala Arg
1               5                   10                  15

Ala Leu Arg Leu Ile Gly Val Pro Thr Asp Ile Gly Ala Ser Arg Leu
            20                  25                  30

Gly Ser Ala Met Gly Pro Asp Ala Leu Arg Val Ala Gly Leu Gly Pro
        35                  40                  45

Ala Leu Arg Gln Leu Gly Cys Gln Val Ser Asp Ile Gly Asn Leu Ala
    50                  55                  60

Gly Pro Pro Asn Pro Gln Thr Pro Pro Glu Gln Gly Leu Arg His Leu
65                  70                  75                  80

Ala Pro Ala Arg Ala Trp Met Asp Ala Val His Gln Ala Val Gly Arg
                85                  90                  95

Ala Leu Asp Asp Gly Glu Leu Pro Leu Met Leu Gly Gly Asp His Ser
            100                 105                 110

Leu Ala Met Gly Ser Ile Ser Ala Val Ala Ala His Cys Arg Arg Arg
        115                 120                 125

Gly Arg Ala Leu Arg Val Ile Trp Leu Asp Ala His Ala Asp Cys Asn
    130                 135                 140

Thr Pro Asp Ile Ser Pro Ser Gly Asn Leu His Gly Met Pro Val Ala
145                 150                 155                 160

Ser Leu Cys Gly Leu Gly Pro Ala Ala Leu Thr Ala Leu Ser Gln Gly
                165                 170                 175

Gly Asp Pro Ala Leu Ala Ala Ser Leu Cys Gln Ile Gly Leu Arg
            180                 185                 190

Ser Val Asp Asp Gln Glu Lys Arg Leu Leu Tyr Ser Leu Gly Val Glu
        195                 200                 205

Val Tyr Asp Met Arg Ala Ile Asp Glu Leu Gly Met Arg Glu Val Met
    210                 215                 220

Arg Arg Ala Leu Glu Asp Leu Glu Gly Ser Asp Thr His Leu His Leu
225                 230                 235                 240

Ser Phe Asp Val Asp Tyr Leu Asp Pro Asp Ile Ala Pro Gly Thr Gly
                245                 250                 255

Thr Pro Val Arg Gly Gly Pro Ser Tyr Arg Glu Ala Gln Leu Cys Met
            260                 265                 270

Glu Met Leu Ala Asp Thr Gly Arg Leu Gly Ser Met Asp Leu Val Glu
        275                 280                 285

Leu Asn Pro Ala Leu Asp Val Arg Asn Gln Thr Ala Glu Leu Val Val
    290                 295                 300

Asp Leu Leu Glu Ser Leu Phe Gly Lys Ser Thr Leu Val Arg Ala Asp
305                 310                 315                 320

Arg
```

<210> SEQ ID NO 40
<211> LENGTH: 299
<212> TYPE: PRT
<213> ORGANISM: Bacillus coagulans

<400> SEQUENCE: 40

```
Met Glu Lys His Ile Ala Ile Met Gly Val Pro Met Asp Leu Gly Gln
1               5                   10                  15

Arg Tyr Lys Gly Val Asp Leu Gly Pro Gln Ala Ile Arg Tyr Ala Gly
            20                  25                  30

Val Lys Glu Gly Leu Glu Lys Leu Gly Cys Ala Val Thr Asp Leu Gly
        35                  40                  45

Asn Ile Glu Ile Gly Arg Ala Glu Gln Leu Pro Asp Asp Glu Val Asn
50                  55                  60

Ala Arg Asn Leu Lys Thr Ile Ala Lys Ala Ser Gln Phe Ile Ala Glu
65                  70                  75                  80

His Thr Asp Glu Ile Val Lys Ser Asn Arg Phe Pro Leu Ile Phe Gly
                85                  90                  95

Gly Asp His Ser Ile Ala Ile Gly Thr Ile Ala Gly Ile Ser Lys His
            100                 105                 110

Tyr Arg Asn Leu Gly Val Ile Trp Phe Asp Ala His Ala Asp Met Asn
        115                 120                 125

Thr Pro Glu Thr Ser Pro Ser Gly Asn Val His Gly Met Pro Leu Ala
130                 135                 140

Ala Ser Leu Gly Tyr Gly His Ala Ser Leu Thr Gly Val Tyr Gly Tyr
145                 150                 155                 160

Ile Pro Lys Leu Lys Ala Glu His Val Val Leu Ile Gly Gln Arg Asp
                165                 170                 175

Leu Asp Glu Gly Glu Lys Asp Phe Ile Arg Asn Leu Gly Ile Lys Ile
            180                 185                 190

Tyr Thr Met Ala Glu Ile Asp Arg Ile Gly Met Glu Ser Val Met Ala
        195                 200                 205

Ala Ser Ile Asn Tyr Leu Lys Glu Arg Thr Asp Gly Ile His Leu Ser
210                 215                 220

Leu Asp Leu Asp Ala Leu Asp Pro Gln Glu Ala Pro Gly Val Gly Thr
225                 230                 235                 240

Pro Val Tyr Gly Gly Leu His Phe Arg Glu Ser Arg Leu Ala Met Glu
                245                 250                 255

Ile Leu His Asp Ala Asn Ala Val Val Ser Ala Asp Val Val Glu Val
            260                 265                 270

Asn Pro Ile Leu Asp Ser Arg Asn Gln Thr Ala Glu Lys Ala Val Arg
        275                 280                 285

Leu Ile Glu Thr Leu Phe Gly Lys Lys Leu Leu
290                 295
```

<210> SEQ ID NO 41
<211> LENGTH: 307
<212> TYPE: PRT
<213> ORGANISM: Hoeflea phototrophica

<400> SEQUENCE: 41

```
Met Asn Gln His Cys Ile Leu Val Gly Ala Pro Val Asp Ser Gly Gln
1               5                   10                  15

Ser Asn Pro Gly Cys Leu Met Gly Pro Ala Ser Tyr Arg Val Ala Gly
            20                  25                  30

Leu Ala Gly Thr Leu Ala Glu Leu Gly Cys Ser Val Glu Asp Arg Gly
        35                  40                  45

Asp Leu Ala Pro Arg Pro Leu Ala Pro Glu Asn Cys Ala Asn Ala Ala
50                  55                  60
```

Val His His Leu Ala Glu Thr Ile Ala Trp Thr Gln Ala Leu Thr Ser
65                  70                  75                  80

Ala Ala Glu Ala Ala Met Ala Glu Gly Phe Pro Val Phe Leu Gly Gly
                85                  90                  95

Asp His Ser Leu Ser Leu Gly Thr Val Ala Gly Val Ala Ala His Ala
            100                 105                 110

Gln Lys Gln Gly Arg Pro Leu Phe Val Leu Trp Leu Asp Ala His Ser
        115                 120                 125

Asp Phe His Thr Pro Met Thr Thr Arg Ser Gly Asn Leu His Gly Thr
    130                 135                 140

Pro Val Ala Tyr Leu Ala Gly Leu Gly Asp Phe Glu Ala Phe Pro Pro
145                 150                 155                 160

Phe Pro Gly Pro Val Pro Ala Asp Arg Ile Cys Leu Phe Gly Ile Arg
                165                 170                 175

Ser Val Asp Pro Asp Glu Arg Thr Ala Leu Arg Gly His Gly Ile Thr
            180                 185                 190

Pro Val Asp Met Arg Glu Leu Asp Glu Arg Gly Phe Val Ala Pro Leu
        195                 200                 205

Ser Ala Phe Leu Asp Gln Val Arg Ala Ala Asp Gly Leu Leu His Val
    210                 215                 220

Ser Leu Asp Val Asp Phe Leu Asp Pro Ser Ile Ala Pro Ala Val Gly
225                 230                 235                 240

Thr Thr Val Pro Gly Gly Ala Thr Phe Arg Glu Ala His Leu Val Met
                245                 250                 255

Glu Met Leu His Glu Ser Gly Leu Val Ser Ser Leu Asp Leu Val Glu
            260                 265                 270

Leu Asn Pro Phe Leu Asp Glu Arg Gly Arg Thr Ala Arg Leu Met Val
        275                 280                 285

Asp Leu Thr Ala Ser Leu Met Gly Arg Thr Val Phe Asp Arg Val Asn
    290                 295                 300

Arg Ser Leu
305

<210> SEQ ID NO 42
<211> LENGTH: 299
<212> TYPE: PRT
<213> ORGANISM: Roseiflexus castenholzii

<400> SEQUENCE: 42

Met Arg Asp Val Ala Ile Ile Gly Val Pro Leu Asp Leu Gly Ala Gly
1               5                   10                  15

Arg Arg Gly Val Asp Met Gly Pro Ser Ala Ile Arg Tyr Ala Gly Leu
            20                  25                  30

Arg Glu Arg Ile Val Ala Leu Gly Cys Gln Val Arg Asp Leu Gly Asn
        35                  40                  45

Ile Ser Val Pro Leu Ala Glu Gln Ile Glu Pro Pro Thr Pro Asp Glu
    50                  55                  60

Arg Leu Arg Tyr Leu Gln Pro Ile Ala His Ala Val Arg Asp Leu Ala
65                  70                  75                  80

Gln Arg Val Arg Asp Val Ala Ser Gly Ala Leu Pro Leu Met Leu
                85                  90                  95

Gly Gly Asp His Ser Leu Ser Ile Gly Ser Val Ala Gly Val Ala His
            100                 105                 110

Asn Arg Arg Ile Gly Val Ile Trp Leu Asp Ala His Gly Asp Tyr Asn
        115                 120                 125

```
Thr Pro Glu Thr Thr Pro Ser Gly Asn Ile His Gly Met Gly Leu Ala
        130                 135                 140

Ala Leu Thr Gly Arg Gly His Pro Leu Leu Thr Asp Val Leu Gly Gln
145                 150                 155                 160

Met Pro Ala Val His Pro Ala Asp Val Ala Leu Val Gly Val Arg Ser
                165                 170                 175

Leu Asp Asp Gly Glu Arg Asp Ala Leu Arg Ala Ser Gly Val Arg Val
                180                 185                 190

Phe Thr Met His Asp Ile Asp Arg Arg Gly Met Ala Ser Val Met Glu
                195                 200                 205

Glu Ala Ile Leu His Val Ser Val Asn Thr Ala Gly Phe His Leu Ser
        210                 215                 220

Phe Asp Leu Asp Ala Leu Asp Pro Asn Glu Ala Pro Gly Val Gly Thr
225                 230                 235                 240

Pro Val Leu Gly Gly Met Thr Tyr Arg Glu Ala His Leu Ala Met Glu
                245                 250                 255

Leu Val Ala Ala Ser Gly Arg Leu Ile Gly Leu Asp Leu Val Glu Val
                260                 265                 270

Asn Pro Ile Leu Asp Glu Arg Asn Thr Thr Ala Leu Leu Ala Val Glu
                275                 280                 285

Phe Ala Leu Ser Ala Leu Gly Lys Arg Ile Tyr
290                 295
```

<210> SEQ ID NO 43
<211> LENGTH: 298
<212> TYPE: PRT
<213> ORGANISM: Bacillus methanolicus

<400> SEQUENCE: 43

```
Met Lys Lys Ile Ser Ile Ile Gly Met Pro Met Asp Leu Gly Gln Met
1               5                   10                  15

Arg Arg Gly Val Asp Met Gly Pro Ser Ala Met Arg Tyr Ala Gly Ile
                20                  25                  30

Asn Glu Arg Leu Arg Asn Leu Lys Tyr Glu Ile Glu Asp Leu Gly Asp
        35                  40                  45

Ile Pro Ile Gly Arg Pro Glu Val Val Asn Arg Ser Asp Thr Asn Leu
50                  55                  60

Arg Asn Leu Glu Leu Val Ala Glu Lys Asn Glu Lys Leu Ala Ala Gln
65                  70                  75                  80

Val Asp Glu Val Val Lys Ser Gly Ala Phe Pro Leu Val Leu Gly Gly
                85                  90                  95

Asp His Ser Ile Ala Ile Gly Thr Leu Ala Gly Val Ala Lys His Tyr
                100                 105                 110

Lys Lys Met Gly Val Ile Trp Tyr Asp Ala His Gly Asp Leu Asn Thr
        115                 120                 125

Ala Glu Thr Ser Pro Ser Gly Asn Ile His Gly Met Pro Leu Ala Val
        130                 135                 140

Ser Ile Gly Leu Gly His Pro Met Leu Thr Glu Ile Gly Gly Tyr Ser
145                 150                 155                 160

Pro Lys Val Lys Pro Glu Asn Ile Val Ile Gly Ala Arg Ser Leu
                165                 170                 175

Asp Glu Gly Glu Arg Ala Leu Ile Lys Glu Lys Gly Ile Lys Val Phe
                180                 185                 190

Thr Met His Glu Ile Asp Arg Leu Gly Met Ser Arg Val Met Glu Glu
```

```
            195                 200                 205
Thr Ile Asn Tyr Leu Lys Asp Lys Thr Asp Gly Val His Leu Ser Leu
            210                 215                 220

Asp Leu Asp Gly Leu Asp Pro Ser Asp Ala Pro Gly Val Gly Thr Pro
225                 230                 235                 240

Val Asn Gly Gly Ile Thr Tyr Arg Glu Ser His Leu Ala Met Glu Met
                    245                 250                 255

Leu Ala Glu Ala Gln Leu Ile Thr Ser Ala Glu Phe Val Glu Val Asn
                260                 265                 270

Pro Ile Leu Asp Asp Lys Asn Lys Thr Ala Thr Val Ala Val Ala Leu
            275                 280                 285

Met Gly Ser Leu Phe Gly Glu Lys Leu Leu
290                 295

<210> SEQ ID NO 44
<211> LENGTH: 298
<212> TYPE: PRT
<213> ORGANISM: Bacillus sp. NRRL B-14911

<400> SEQUENCE: 44

Met Lys Lys Leu Ser Ile Ile Gly Met Pro Met Asp Leu Gly Gln Met
1               5                   10                  15

Arg Arg Gly Val Asp Met Gly Pro Ser Ala Ile Arg Tyr Ala Gly Val
                20                  25                  30

Asn Glu Arg Leu Lys Ser Leu Phe Glu His Ile His Asp Leu Gly Asp
            35                  40                  45

Ile Ala Ile Gly Arg Pro Glu Val Glu Ile Asp Pro Thr Asn Leu
50                  55                  60

Arg Asn Leu Glu Leu Ile Ala Asp Lys Thr Gly Gln Leu Ala Glu Lys
65                  70                  75                  80

Val Asp Glu Val Ile Lys Gly Gly Ser Phe Pro Leu Val Leu Gly Gly
                85                  90                  95

Asp His Ser Ile Ala Ile Gly Thr Leu Ala Gly Val Ser Arg His Tyr
                100                 105                 110

Lys Asn Leu Gly Val Ile Trp Tyr Asp Ala His Gly Asp Leu Asn Thr
            115                 120                 125

Ala Glu Thr Ser Pro Ser Gly Asn Ile His Gly Met Pro Leu Ala Ala
            130                 135                 140

Ser Leu Gly Ile Gly His Pro Leu Leu Thr Gly Ile Gly Gly Tyr Ser
145                 150                 155                 160

Pro Lys Val Lys Pro Glu Asn Ile Val Ile Gly Ala Arg Ala Leu
                165                 170                 175

Asp Glu Gly Glu Lys Glu Leu Val Lys Glu Lys Gly Ile Lys Val Tyr
                180                 185                 190

Thr Met His Glu Ile Asp Arg Leu Gly Met Ala Arg Val Met Glu Glu
            195                 200                 205

Ala Ile Glu Tyr Leu Arg Asp Arg Thr Asp Gly Val His Leu Ser Leu
            210                 215                 220

Asp Leu Asp Gly Leu Asp Pro Asn Asp Ala Pro Gly Val Gly Thr Pro
225                 230                 235                 240

Val Ile Gly Gly Ile Ser Tyr Arg Glu Ser His Leu Ala Met Glu Met
                    245                 250                 255

Leu Ala Glu Ala Glu Leu Ile Thr Ser Ala Glu Phe Val Glu Val Asn
                260                 265                 270
```

```
Pro Ile Leu Asp Asp Lys Asn Lys Thr Ala Ser Val Ala Val Ala Leu
            275                 280                 285

Met Gly Ser Leu Phe Gly Glu Lys Leu Leu
            290                 295

<210> SEQ ID NO 45
<211> LENGTH: 302
<212> TYPE: PRT
<213> ORGANISM: Planococcus donghaensis

<400> SEQUENCE: 45

Met Asn Lys Leu Asn Ile Ser Ile Ile Gly Val Pro Met Asp His Gly
1               5                   10                  15

Gln Thr Arg Arg Gly Val Asp Met Gly Pro Ser Ala Ile Arg Tyr Ala
            20                  25                  30

Gly Val Val Asp Arg Ile Glu Glu Leu Gly His Arg Val Thr Asp Glu
            35                  40                  45

Gly Asp Ile Leu Ile Gly Gln Thr Asp Gly Ser Val Asp Thr Glu Thr
        50                  55                  60

Asn Leu Arg Asn Leu Lys Ala Ile Thr Lys Ala Thr Glu Ala Leu Gly
65              70                  75                  80

Asp Lys Val Phe Asn Val Ala Glu Ala Gly Asn Phe Pro Leu Val Leu
                85                  90                  95

Gly Gly Asp His Ser Ile Ala Ile Gly Thr Leu Ala Gly Ile Ser Glu
            100                 105                 110

Arg His Glu Asn Leu Gly Val Ile Trp Tyr Asp Ala His Ala Asp Met
        115                 120                 125

Asn Thr Ser Asp Thr Ser Pro Ser Gly Asn Ile His Gly Met Pro Leu
130                 135                 140

Ala Ala Ser Phe Gly His Gly His Glu Lys Leu Thr Asn Ile Arg Gly
145                 150                 155                 160

Tyr Ser Pro Lys Val Lys Pro Glu Asn Ile Val Ile Ile Gly Ala Arg
                165                 170                 175

Ser Val Asp Pro Gly Glu Arg Glu Leu Ile Lys Glu His Gly Ile Arg
            180                 185                 190

Val Tyr Ser Met His Glu Ile Asp Lys Met Gly Met His Ala Val Ile
        195                 200                 205

Glu Glu Ser Ile Lys Tyr Leu Lys Glu Arg Lys Thr Asp Ala Val
            210                 215                 220

His Leu Ser Leu Asp Leu Asp Gly Ile Asp Pro Met Tyr Thr Pro Gly
225                 230                 235                 240

Val Gly Thr Pro Val Pro Gly Gly Ile Ser Tyr Arg Glu Ser His Leu
                245                 250                 255

Ala Met Glu Met Leu Phe Asp Ala Asn Ile Ile Thr Ser Ala Glu Phe
            260                 265                 270

Val Glu Val Asn Pro Ile Leu Asp Glu Lys Asn Lys Thr Ala Asp Val
        275                 280                 285

Ala Val Ala Leu Ile Gly Ser Leu Phe Gly Glu Lys Leu Leu
    290                 295                 300

<210> SEQ ID NO 46
<211> LENGTH: 301
<212> TYPE: PRT
<213> ORGANISM: Paenibacillus dendritiformis

<400> SEQUENCE: 46
```

```
Met Asp Arg Asn Leu Ile Ser Leu Leu Arg Val Pro Tyr Gly Lys Gly
1               5                   10                  15

Gly Ala Arg Pro Gly Ala Glu Gln Gly Pro Asp Ala Leu Leu Glu Ala
            20                  25                  30

Gly Leu Val Arg His Leu Ser Gln Leu Gly Leu Gln Thr Ile Asp Glu
        35                  40                  45

Gly Ala Val Leu Pro Pro Ser Ala Gln Asp Ser Thr Gln Ala Ser Gly
    50                  55                  60

Thr Lys Leu Lys His Leu Glu Glu Ile Ala Ala Leu Asn Ser Glu Leu
65                  70                  75                  80

Ala Asp Arg Val Ala Glu Ala Ala Ser Gly Arg Phe Pro Leu Ile
                85                  90                  95

Leu Gly Gly Asp His Ser Ile Ala Ile Gly Thr Ile Ala Gly Leu Thr
                100                 105                 110

Arg His Tyr Arg Asn Leu Gly Val Ile Trp Phe Asp Ala His Gly Asp
            115                 120                 125

Leu Asn Thr Glu Asp Thr Ser Pro Ser Gly Asn Ile His Gly Met Ser
    130                 135                 140

Leu Ala Val Asn Leu Asp Gln Gly His Pro Leu Leu Thr Arg Ile Arg
145                 150                 155                 160

Arg Gln Ser Ser Arg Ile Asp Pro Ala Lys Val Val Ile Ile Gly Ala
                165                 170                 175

Arg Ser Leu Asp Glu Gly Glu Arg Ala Tyr Ile Arg Gln Ala Gly Ile
            180                 185                 190

Thr Cys Phe Thr Met His Asp Ile Asp Arg Lys Gly Met Pro Tyr Val
    195                 200                 205

Met Glu Gln Ala Leu Arg Ile Leu Gly Asp Gly Thr Asp Gly Val His
210                 215                 220

Leu Ser Phe Asp Ile Asp Ser Leu Asp Pro Ala Glu Ala Pro Gly Thr
225                 230                 235                 240

Gly Thr Pro Ile Pro Gly Gly Val Ser Tyr Arg Glu Ala His Leu Ala
                245                 250                 255

Leu Glu Met Met Tyr Glu Ser Gly Leu Ile Thr Ser Ala Glu Phe Val
            260                 265                 270

Glu Val Ser Pro Pro Leu Asp Ser Gln Lys Arg Thr Val Arg Leu Ala
        275                 280                 285

Ile Gly Leu Ile Gly Ser Leu Leu Gly Glu Gln Ile Leu
            290                 295                 300

<210> SEQ ID NO 47
<211> LENGTH: 300
<212> TYPE: PRT
<213> ORGANISM: Desmospora sp.

<400> SEQUENCE: 47

Met His Asn Asn Ile Thr Ile Val Gly Val Pro Met Asp Leu Gly
1               5                   10                  15

Ala Asp Arg Arg Gly Val Asp Met Gly Pro Ser Ala Ile Arg Tyr Ala
            20                  25                  30

Ser Leu Lys Glu Lys Leu Thr Gly Leu Gly Tyr Asp Val Lys Asp Ser
        35                  40                  45

Gly Asn Leu Ala Val Pro Thr Pro Glu Ser Tyr Asp Val Gly Ser Ser
    50                  55                  60

Gln Leu Lys Tyr Leu Arg Glu Ile Thr Gln Val Ser Glu Glu Leu Ala
65                  70                  75                  80
```

Val Thr Val Asp Asp Val Ile Gln Lys Gly Arg Phe Pro Leu Val Leu
            85                  90                  95

Gly Gly Asp His Ser Ile Ala Ile Gly Thr Ile Ala Gly Val Ala Lys
            100                 105                 110

His Tyr Lys Arg Met Gly Ile Ile Trp Phe Asp Ala His Gly Asp Leu
            115                 120                 125

Asn Thr Ala Asp Thr Ser Pro Ser Gly Asn Ile His Gly Met Pro Leu
    130                 135                 140

Ala Ala Ser Leu Gly Ile Gly His Pro Asp Leu Val Asn Ile Gly Gly
145                 150                 155                 160

Phe Ser Pro Lys Val Arg Pro Glu Asn Val Val Ile Gly Ala Arg
                165                 170                 175

Asp Leu Asp Glu Gly Glu Arg Val Leu Ile Arg Glu Gln Gly Ile Lys
            180                 185                 190

Val Phe Thr Met His Asp Ile Asp Arg Leu Gly Met Gly Ala Val Met
            195                 200                 205

Glu Glu Thr Leu Cys Ile Val Thr Asp Gly Thr Asp Gly Val His Leu
    210                 215                 220

Ser Leu Asp Leu Asp Gly Leu Asp Pro His Asp Ala Pro Gly Val Gly
225                 230                 235                 240

Thr Pro Val Val Gly Gly Ile Thr Tyr Arg Glu Gly His Leu Ala Met
                245                 250                 255

Glu Met Leu Ala Ala Ser Asn Val Leu Thr Ser Ala Glu Phe Val Glu
            260                 265                 270

Val Asn Pro Ile Leu Asp His Gly Asn Arg Thr Ala Lys Ala Ala Val
            275                 280                 285

Ala Leu Ile Gly Ser Val Phe Gly Glu Lys Val Leu
            290                 295                 300

<210> SEQ ID NO 48
<211> LENGTH: 288
<212> TYPE: PRT
<213> ORGANISM: Methylobacter tundripaludum

<400> SEQUENCE: 48

Met Ala Ile Leu Gln Thr Leu Gly Ile Ala Ser Cys Leu Gly Gly Pro
1               5                   10                  15

Leu Arg Thr Cys Gly Tyr Ala Ala Glu Met Leu Arg Asp Ala Phe Ala
            20                  25                  30

Leu Gln Lys Pro Glu Gln Gln Gly Leu Gln Leu Gln Trp His Met Leu
        35                  40                  45

Tyr Pro Glu Asn Asn Gly Ser Lys Asp Glu Lys Leu Ser Arg Leu Asn
    50                  55                  60

Gln Ser Ile Ser Arg Phe Ser Gln Tyr Trp Thr Gln Asn Gln Val
65                  70                  75                  80

Phe Leu Val Ile Gly Gly Asp His Ser Cys Ala Leu Gly Thr Trp Gly
            85                  90                  95

Gly Val Leu Asn Gly Leu Gln Arg Pro Gly Lys Phe Gly Leu Ile Trp
            100                 105                 110

Leu Asp Ala His Met Asp Ala His Thr Phe Ala Thr Ser Pro Ser Gly
        115                 120                 125

Asn Ile His Gly Met Pro Leu Ala Ala Leu Leu Gly Lys Ala Asp Lys
    130                 135                 140

Lys Leu Ala Ala Met Tyr Pro Gly Ser Asp Phe Ile Lys Pro Glu Asn

```
                145                 150                 155                 160
Leu Ile Leu Ile Gly Val Arg Ser Tyr Glu Asn Glu Glu Tyr Asp Leu
                    165                 170                 175

Leu Lys Gln Ala Lys Val Glu Ile Ile Phe Ala Glu Gln Ile Asp Gly
                    180                 185                 190

Leu Ala Gln Val Leu Thr Lys Ala Ile Asp Lys Leu Ser Leu Ser Cys
                    195                 200                 205

Gln Val Ile Gly Ile Ser Ile Asp Leu Asp Phe Ile Asp Pro Asp Asp
                    210                 215                 220

Ala Pro Gly Val Glu Thr Pro Ala Gln Gly Gly Ile Lys Ala Glu Glu
225                 230                 235                 240

Leu Leu Lys Ala Leu Ala Leu Ile Asn Arg His Pro Lys Ile Cys Gly
                    245                 250                 255

Leu Glu Ile Ser Glu Phe Asn Pro Glu Lys Asp Pro Glu Asn Lys Thr
                    260                 265                 270

Leu His Leu Met Lys Lys Ile Ile Glu Thr Phe Tyr Gly Glu Thr Leu
                    275                 280                 285

<210> SEQ ID NO 49
<211> LENGTH: 306
<212> TYPE: PRT
<213> ORGANISM: Stenotrophomonas sp.

<400> SEQUENCE: 49

Met Ala His Pro Ile Ser Val Ser Leu Ile Gly Val Pro Thr Asp Val
1               5                   10                  15

Gly Ala Gly His Arg Gly Ala Arg Leu Gly Pro Glu Ala Leu Arg Val
                    20                  25                  30

Ala Gly Leu Pro Glu Ala Leu Glu Ala Arg Gly Val Asp Val Arg Asp
                    35                  40                  45

Leu Gly Asn Leu Asp Gly Pro Arg Asn Pro Trp Thr Ala Pro Val Glu
                50                  55                  60

Gly Tyr Arg His Leu Asp Glu Val Val Ala Trp Asn His Ala Leu Met
65                  70                  75                  80

Glu Ala Ser Tyr Ala Glu Leu Gln Ala Gly Arg Met Pro Ile Met Leu
                    85                  90                  95

Gly Gly Asp His Cys Leu Gly Ile Gly Ser Ile Thr Ala Val Ala Arg
                    100                 105                 110

Trp Cys Arg Glu Gln Gly Lys Thr Leu Arg Val Leu Trp Leu Asp Ala
                    115                 120                 125

His Ser Asp Phe Asn Thr Ser Asp Val Thr Pro Ser Gly Asn Ile His
                    130                 135                 140

Gly Met Pro Val Ala Cys Leu Cys Gly Leu Gly Pro Asp Ala Leu Thr
145                 150                 155                 160

Gln Leu Gly Gly Thr Ser Pro Ala Ile Thr Pro Ala Gln Met His Gln
                    165                 170                 175

Ile Gly Ile Arg Ser Val Asp Pro Glu Lys Arg Leu Ile Lys Thr
                    180                 185                 190

His Lys Val Asp Val Tyr Asp Met Arg Tyr Ile Asp Glu Asn Gly Met
                    195                 200                 205

Lys Arg Thr Val Glu Ala Ala Leu Ala Gly Ile Asp Glu Asn Thr His
                    210                 215                 220

Leu His Val Ser Phe Asp Val Asp Phe Leu Asp Pro Ser Ile Ala Pro
225                 230                 235                 240
```

```
Gly Val Gly Thr Thr Val Pro Gly Gly Val Asn Tyr Arg Glu Ala Gln
                245                 250                 255

Leu Val Met Glu Met Ile Ala Asp Thr Gly Arg Met Gly Ser Leu Asp
            260                 265                 270

Ile Val Glu Leu Asn Pro Leu Leu Asp Lys Gln Asn Ala Thr Ala Glu
        275                 280                 285

Leu Ala Val Asp Leu Val Glu Ser Leu Phe Gly Lys Ser Thr Leu Met
    290                 295                 300

Arg Asp
305

<210> SEQ ID NO 50
<211> LENGTH: 270
<212> TYPE: PRT
<213> ORGANISM: Microbacterium laevaniformans

<400> SEQUENCE: 50

Met Thr Arg Phe Val Val Pro Gln Trp Gln Gly Ser Pro Ala Ala
1               5                   10                  15

Arg Ala Met Leu Leu Val Asp Gly Ala Glu Ala Ile Ala Gly Asp Leu
            20                  25                  30

Pro Arg Ala Thr Thr Ala Arg Val Asp Val Pro Ala Glu Ala Gly Glu
        35                  40                  45

Ala Leu Glu Thr Gly Ile Arg Arg Phe Ser Ala Leu His Arg Val Ala
    50                  55                  60

Asp Ala Leu Thr Ala Glu Leu Ala Val Ser Asp Glu Ala Ala Leu Ile
65                  70                  75                  80

Val Gly Gly Asp Cys Gly Val Ala Val Pro Ala Ile Ala His Tyr Ala
                85                  90                  95

Ala Arg Asn Pro Glu Leu Ala Val Val Trp Phe Asp Ala His Gly Asp
            100                 105                 110

Leu Asn Thr Pro Ala Thr Ser Pro Ser Gly Ala Phe Ala Gly Met Ala
        115                 120                 125

Leu Arg Ala Val His Glu Ser Gly Pro Val Pro Gly Ser Gly Ala Val
    130                 135                 140

Thr Ala Asp Arg Leu Val Leu Val Gly Ala Arg Asp Leu Asp Pro Gly
145                 150                 155                 160

Glu Ala Ala His Leu Ala Glu Ser Asp Ile Arg Ser Val Ala Ala Asp
                165                 170                 175

Ala Ile Gly Asp Gly Ala Ala Ile Ala Ala Val Ala Ala Thr Gly
            180                 185                 190

Ala Glu Ala Val Tyr Ile His Val Asp Leu Asp Val Leu Asp Pro Ala
    195                 200                 205

Glu Leu Thr Gly Val Thr Arg Pro Thr Pro Phe Gly Leu Thr Leu Arg
210                 215                 220

Glu Leu Thr Ala Thr Ile Ala Ala Val Arg Arg Thr Leu Pro Leu Val
225                 230                 235                 240

Gly Ala Ser Ile Ala Gly Phe Ala Pro Ala Ser Pro Ala Ala Val
                245                 250                 255

Asp Asp Leu Gly Thr Ile Leu Arg Val Val Gly Ala Leu Ala
            260                 265                 270

<210> SEQ ID NO 51
<211> LENGTH: 298
<212> TYPE: PRT
<213> ORGANISM: Porphyromonas uenonis
```

<400> SEQUENCE: 51

Met Lys Thr Phe Asp Val Ile Gly Tyr Pro Ile Asn Leu Gly Cys Asp
1               5                   10                  15

Lys Asp Gly Asn Glu Leu Thr Pro Ser Ile Leu Arg Arg Asp Gly Cys
            20                  25                  30

Tyr Thr Ser Ala Lys His His Val Asn Asp Leu Gly Asp Leu Pro Cys
        35                  40                  45

Thr Pro Arg Ala Ala Ile Ile Glu Glu Lys Phe Ala Ser His Pro Lys
    50                  55                  60

Ile Lys Tyr Leu Lys Pro Ile Leu Thr Ala Ser Arg Pro Leu Ala Glu
65                  70                  75                  80

Arg Val Met His Ser Ile Ala Gln Gln His Ile Pro Leu Cys Val Gly
                85                  90                  95

Gly Asp His Val Met Ala Phe Gly Ser Ile Ala Gly Val Gly Leu Thr
            100                 105                 110

Lys Gly Ala Asp Asn Phe Ala Val Ile Tyr Ile Asp Ala His Gly Asp
        115                 120                 125

Phe Asn Thr Glu Ile Thr Ser Gly Thr Gly Asn Met His Gly Met His
    130                 135                 140

Leu Ser Tyr Leu Met Gly Tyr Gly Glu Ala Asp Ile Ala Asn Phe Trp
145                 150                 155                 160

Gly Val Ser Pro Leu Leu Lys Pro Gln Asn Ile Tyr Phe Leu Gly Ala
                165                 170                 175

Arg Ala Leu Asp Pro Gly Glu Ile Glu Met Ala Ala Lys Leu Asn Met
            180                 185                 190

Tyr Ile Arg Ser Ser Glu Gln Leu Asn Ala Ser Asp Pro Ala Glu Val
        195                 200                 205

Ile Val Asp Ile Leu Ser Asp Ile Lys Arg Lys Gly Ile Asp His Ile
    210                 215                 220

His Leu Ser Phe Asp Val Asp Val Ile Asp Pro Glu Tyr Ala Pro Gly
225                 230                 235                 240

Thr Gly Val Pro Glu Lys Lys Gly Ile Pro Pro Ala Leu Ala Tyr Thr
                245                 250                 255

Leu Ile Arg Leu Cys Met Gln Ser Asp Leu Val Lys Ser Val Asp Ile
            260                 265                 270

Val Glu Leu Asn Ala Asn Leu Asp Gln Gly Arg Ile Thr Glu Arg Ala
        275                 280                 285

Met Gln Gln Val Leu Lys Ile Ile Leu Glu
    290                 295

<210> SEQ ID NO 52
<211> LENGTH: 306
<212> TYPE: PRT
<213> ORGANISM: Agrobacterium sp.

<400> SEQUENCE: 52

Met Asp Ile Arg Leu Val Gly Ala Pro Leu Gln Ile Gly Ala Gly Gln
1               5                   10                  15

Leu Gly Cys Glu Met Gly Pro Ser Ala Tyr Arg Val Ala Gly Leu Ala
            20                  25                  30

His Ala Leu Glu Glu Leu Gly His Arg Val Val Asp Thr Gly Asn Val
        35                  40                  45

Met Pro Ala Pro Leu Arg Glu Phe Cys His Pro Asn Pro Ala Val His
    50                  55                  60

```
His Leu Ala Glu Thr Val Ala Trp Thr Glu Ala Leu Thr Glu Ala Ala
 65                  70                  75                  80

Tyr Arg Glu Ser Ala Asp Ala Val Pro Ile Phe Leu Gly Gly Asp His
             85                  90                  95

Ala Ile Ser Ala Gly Thr Val Ala Gly Met Ala Arg Arg Val Ala Glu
        100                 105                 110

Thr Gly Arg Pro Phe Phe Val Leu Trp Leu Asp Ala His Thr Asp Tyr
    115                 120                 125

His Thr Leu Glu Thr Thr Arg Ser Gly Asn Leu His Gly Thr Pro Val
130                 135                 140

Ala Tyr Phe Ser Gly Arg Asp Gly Phe Ser Gly Tyr Phe Pro Pro Leu
145                 150                 155                 160

Ser His Ala Val Ala Glu Glu Asn Ile Gly Met Ile Gly Ile Arg Ser
                165                 170                 175

Val Asp Pro Ala Glu Arg Ala Ala Leu Glu Lys Ser Gly Ile Thr Val
            180                 185                 190

His Asp Met Arg Ser Ile Asp Glu His Gly Val Ala Val Ile Leu Arg
        195                 200                 205

Glu Phe Leu Ala Arg Val Gln Ala Ala Asn Gly Leu Leu His Val Ser
    210                 215                 220

Leu Asp Val Asp Phe Leu Glu Pro Ser Ile Ala Pro Ala Val Gly Thr
225                 230                 235                 240

Thr Val Pro Gly Gly Ala Thr Phe Arg Glu Ala His Leu Val Met Glu
                245                 250                 255

Met Leu His Asp Ser Gly Leu Val Cys Ser Leu Asp Leu Val Glu Leu
            260                 265                 270

Asn Pro Phe Leu Asp Glu Arg Gly Arg Thr Ala Thr Leu Met Val Asp
        275                 280                 285

Leu Ala Thr Ser Leu Met Gly Lys Arg Val Met Asp Arg Pro Thr Arg
    290                 295                 300

Ala Gly
305

<210> SEQ ID NO 53
<211> LENGTH: 310
<212> TYPE: PRT
<213> ORGANISM: Octadecabacter arcticus

<400> SEQUENCE: 53

Met Thr Pro Gln Asn Ile Ile Leu Ile Gly Ala Pro Val Asp Ser Gly
1               5                   10                  15

Lys Asp Arg Lys Gly Cys Ile Met Gly Pro Asp Ala Phe Arg Thr Ala
            20                  25                  30

Arg Leu Gly Asp Ile Leu Thr Glu Leu Gly His Ser Val Thr Asp Leu
        35                  40                  45

Gly Asn Leu Thr Ala Gln Asp Thr Asp Ile Pro Glu His Asp His Leu
    50                  55                  60

Ile Ala Leu Pro Gln Thr Ile Gly Trp Thr Arg Thr Leu Lys Lys Ala
65                  70                  75                  80

Ala Lys Asp Ala Ala Pro Lys Gly Leu Pro Ile Phe Leu Gly Gly Asp
                85                  90                  95

His Ser Leu Ala Leu Gly Ser Val Thr Gly Ile Ala Asp Tyr Ala Ala
            100                 105                 110

Ser Ile Asp Lys Pro Leu Phe Val Leu Trp Leu Asp Ala His Ser Asp
```

```
                    115                 120                 125
Phe His Thr Pro Gln Thr Thr Ala Ser Gly Asn Leu His Gly Thr Pro
            130                 135                 140
Val Ala Tyr Leu Ser Gly Gln Ser Gly Phe Asp Asp Phe Pro Ile Val
145                 150                 155                 160
Ser Asn Pro Val Pro Thr Glu Asn Ile Cys Met Ile Gly Leu Arg Ser
                165                 170                 175
Val Asp Pro Ala Glu His Ala Ala Leu Ala Asn Thr Asp Val Glu Ile
            180                 185                 190
Ala Asp Met Arg Ala Ile Asp Glu Gly Gly Ile Arg Ala Pro Leu Ala
                195                 200                 205
Glu Phe Leu Ala Lys Val Glu Ala Ala Asp Gly Leu Leu His Val Ser
            210                 215                 220
Leu Asp Val Asp Phe Leu Asp Pro Asp Ile Ala Pro Ala Val Gly Thr
225                 230                 235                 240
Thr Val Pro Gly Gly Ala Thr Leu Arg Glu Ala His Leu Val Met Glu
                245                 250                 255
Leu Leu His Asp Ser Ala Arg Val Thr Ser Leu Asp Leu Val Glu Leu
            260                 265                 270
Asn Pro Phe Met Asp Glu Arg Gly Lys Thr Ala Ser Leu Leu Val Asp
                275                 280                 285
Leu Thr Ala Ser Leu Met Gly Arg Arg Val Phe Asp Arg Pro Thr Arg
            290                 295                 300
Ser Phe Ala Gly Ala Val
305                 310

<210> SEQ ID NO 54
<211> LENGTH: 306
<212> TYPE: PRT
<213> ORGANISM: Agrobacterium tumefaciens

<400> SEQUENCE: 54

Met Asp Ile Arg Leu Val Gly Ala Pro Leu Gln Ile Gly Ala Gly Gln
1               5                   10                  15
Leu Gly Cys Glu Met Gly Pro Ser Ala Tyr Arg Val Ala Gly Leu Ala
                20                  25                  30
His Ala Leu Glu Glu Leu Gly His Arg Val Val Asp Thr Gly Asn Val
            35                  40                  45
Met Pro Ala Pro Leu Arg Glu Phe Cys His Pro Asn Pro Ala Val His
50                  55                  60
His Leu Ala Glu Thr Val Ala Trp Thr Glu Ala Leu Thr Glu Ala Ala
65                  70                  75                  80
Tyr Arg Glu Ser Ala Asp Ala Val Pro Ile Phe Leu Gly Gly Asp His
                85                  90                  95
Ala Ile Ser Ala Gly Thr Val Ala Gly Met Ala Arg Arg Val Ala Glu
            100                 105                 110
Thr Gly Arg Pro Phe Phe Val Leu Trp Leu Asp Ala His Thr Asp Tyr
        115                 120                 125
His Thr Leu Glu Thr Thr Arg Ser Gly Asn Leu His Gly Thr Pro Val
            130                 135                 140
Ala Tyr Phe Ser Gly Arg Asp Gly Phe Ser Gly Tyr Phe Pro Pro Leu
145                 150                 155                 160
Ser His Ala Val Ala Glu Glu Asn Ile Gly Met Ile Gly Ile Arg Ser
                165                 170                 175
```

```
Val Asp Pro Ala Glu Arg Ala Ala Leu Glu Lys Ser Gly Ile Thr Val
            180                 185                 190

His Asp Met Arg Ser Ile Asp Glu His Gly Val Ala Val Ile Leu Arg
        195                 200                 205

Glu Phe Leu Ala Arg Val Gln Ala Ala Asn Gly Leu Leu His Val Ser
    210                 215                 220

Leu Asp Val Asp Phe Leu Glu Pro Ser Ile Ala Pro Ala Val Gly Thr
225                 230                 235                 240

Thr Val Pro Gly Gly Ala Thr Phe Arg Glu Ala His Leu Val Met Glu
                245                 250                 255

Met Leu His Asp Ser Gly Leu Val Cys Ser Leu Asp Leu Val Glu Leu
            260                 265                 270

Asn Pro Phe Leu Asp Glu Arg Gly Arg Thr Ala Thr Leu Met Val Asp
        275                 280                 285

Leu Ala Thr Ser Leu Met Gly Lys Arg Val Met Asp Arg Pro Thr Arg
    290                 295                 300

Ala Gly
305

<210> SEQ ID NO 55
<211> LENGTH: 298
<212> TYPE: PRT
<213> ORGANISM: Anoxybacillus flavithermus

<400> SEQUENCE: 55

Met Asn Ile Ser Ile Ile Gly Val Pro Met Asp Leu Gly Gln Thr Arg
1               5                   10                  15

Arg Gly Val Asp Met Gly Pro Ser Ala Ile Arg Tyr Ala Gly Val Val
            20                  25                  30

Glu Arg Leu Glu Asn Leu Asn His Asp Ile Glu Asp Leu Gly Asp Ile
        35                  40                  45

Gln Ile Gly Arg Ala Glu Arg Val Gln Asp Val Thr Asn Pro Lys Leu
    50                  55                  60

Arg Asn Leu Lys Ala Val Ala Glu Ala Asn Glu Lys Leu Ala Ala Thr
65                  70                  75                  80

Val Asp Asp Val Val Thr Arg Gly Arg Phe Pro Leu Val Leu Gly Gly
                85                  90                  95

Asp His Ser Ile Ala Ile Gly Thr Leu Ala Gly Val Ala Lys His Tyr
            100                 105                 110

Lys Asn Leu Gly Val Ile Trp Tyr Asp Ala His Gly Asp Leu Asn Thr
        115                 120                 125

Glu Glu Thr Ser Pro Ser Gly Asn Ile His Gly Met Pro Leu Ala Ala
    130                 135                 140

Ser Leu Gly Leu Gly His Pro Ala Leu Thr Met Ile Gly Gly Tyr Ser
145                 150                 155                 160

Pro Lys Val Lys Pro Glu Asn Ile Val Ile Gly Ala Arg Ala Leu
                165                 170                 175

Asp Glu Gly Glu Lys Gln Leu Ile Lys Glu Lys Gly Ile Lys Ile Tyr
            180                 185                 190

Thr Met His Glu Val Asp Arg Leu Gly Met Thr Lys Val Met Glu Glu
        195                 200                 205

Thr Ile Ala Tyr Leu Lys Glu Arg Thr Asp Gly Val His Leu Ser Leu
    210                 215                 220

Asp Leu Asp Gly Leu Asp Pro His Asp Ala Pro Gly Val Gly Thr Pro
225                 230                 235                 240
```

```
Val Ile Gly Gly Leu Ser Tyr Arg Glu Ser His Leu Ala Met Glu Met
                245                 250                 255

Leu Ala Glu Ala Gln Ile Ile Thr Ser Ala Glu Phe Val Glu Val Asn
            260                 265                 270

Pro Ile Leu Asp Glu Arg Asn Lys Thr Ala Ala Thr Ala Val Ala Leu
        275                 280                 285

Met Gly Ser Leu Phe Gly Glu Lys Leu Val
    290                 295

<210> SEQ ID NO 56
<211> LENGTH: 303
<212> TYPE: PRT
<213> ORGANISM: Bacillus pumilus

<400> SEQUENCE: 56

Met Gly Glu Gln Lys Lys Val Thr Leu Val Gly Val Pro Met Asp Leu
1               5                   10                  15

Gly Gln Met Arg Arg Gly Val Asp Met Gly Pro Ser Ala Ile Arg Cys
            20                  25                  30

Ala Gly Val Lys Glu Lys Leu Glu Ser Leu Ser Phe Gly Val Glu Asp
        35                  40                  45

Leu Gly Asp Ile Pro Val Glu Gln Arg Asp Asp Glu Lys Gly Leu Tyr
    50                  55                  60

Thr Ser Glu Lys Leu Lys Asn Leu Thr Glu Asn Ala Gly Ala Asn Gln
65                  70                  75                  80

Leu Leu Ala Glu Lys Val Asp Ser Ile Val Gln Ser Gly Ser Phe Pro
                85                  90                  95

Leu Ile Leu Gly Gly Asp His Ser Ile Ala Ile Gly Thr Leu Ala Gly
            100                 105                 110

Val Ser Lys His Tyr Glu Asn Leu Gly Val Ile Trp Tyr Asp Ala His
        115                 120                 125

Gly Asp Leu Asn Thr Glu Glu Thr Ser Pro Ser Gly Asn Ile His Gly
    130                 135                 140

Met Pro Leu Ala Val Ser Leu Gly Leu Gly His Ala Asp Leu Thr Asn
145                 150                 155                 160

Ile Gly Gly Tyr Ser Pro Lys Leu Lys Pro Glu Asn Val Val Leu Ile
                165                 170                 175

Gly Ala Arg Ser Leu Asp Glu Gly Glu Arg Ala Leu Ile Arg Glu Lys
            180                 185                 190

Gly Ile Lys Val Tyr Thr Met His Glu Ile Asp Arg Leu Gly Met Thr
        195                 200                 205

Arg Val Met Glu Glu Ala Ile Ser Tyr Leu Lys Glu Arg Thr Asp Gly
    210                 215                 220

Val His Leu Ser Leu Asp Leu Asp Gly Leu Asp Pro Ala Glu Cys Pro
225                 230                 235                 240

Gly Val Gly Thr Pro Val Ala Gly Gly Ile Ser Tyr Arg Glu Ser His
                245                 250                 255

Leu Ala Met Glu Leu Leu Glu Glu Ala Gly Ile Leu Thr Ser Ala Glu
            260                 265                 270

Phe Val Glu Val Asn Pro Val Leu Asp Glu Lys Asn Lys Thr Ala Glu
        275                 280                 285

Ala Ala Val Ala Leu Ile Gly Ser Leu Met Gly Glu Lys Leu Leu
    290                 295                 300
```

```
<210> SEQ ID NO 57
<211> LENGTH: 306
<212> TYPE: PRT
<213> ORGANISM: Geobacillus thermoglucosidasius

<400> SEQUENCE: 57

Met Glu Arg Gly Asn Ser Val Lys Lys Val Ser Ile Ile Gly Val Pro
1               5                   10                  15

Met Asp Leu Gly Gln Thr Arg Arg Gly Val Asp Met Gly Pro Ser Ala
            20                  25                  30

Met Arg Tyr Ala Gly Ile Ile Glu Arg Leu Glu Arg Leu His Tyr Glu
        35                  40                  45

Ile Glu Asp Leu Gly Asp Val Ser Ile Gly Lys Met Glu Trp Ser Asp
    50                  55                  60

Asp Glu Gly Leu Arg Leu Asn Leu Arg Asn Leu Lys Ala Val Ala Lys
65                  70                  75                  80

Thr Asn Glu Lys Leu Ala Glu Met Val Asp Asp Val Val Gln Arg Gly
                85                  90                  95

Arg Phe Pro Leu Val Leu Gly Gly Asp His Ser Ile Ala Ile Gly Thr
            100                 105                 110

Leu Ala Gly Val Ala Lys His Tyr Gln Asn Leu Gly Val Ile Trp Tyr
        115                 120                 125

Asp Ala His Gly Asp Leu Asn Thr Ala Glu Thr Ser Pro Ser Gly Asn
    130                 135                 140

Ile His Gly Met Ser Leu Ala Val Cys Leu Gly Leu Gly His Pro Tyr
145                 150                 155                 160

Leu Thr Lys Ile Gly Gly Tyr Ser Pro Lys Val Lys Pro Glu Asn Val
                165                 170                 175

Val Leu Ile Gly Val Arg Ser Leu Asp Glu Gly Glu Lys Gln Leu Ile
            180                 185                 190

Arg Glu Lys Gly Ile Lys Val Tyr Thr Met His Glu Val Asp Arg Leu
        195                 200                 205

Gly Met Ala Ala Val Met Glu Glu Thr Ile Ala Tyr Leu Gln Gly Arg
    210                 215                 220

Thr Asp Gly Val His Leu Ser Leu Asp Leu Asp Gly Leu Asp Pro His
225                 230                 235                 240

Asp Ala Pro Gly Val Gly Thr Pro Val Ile Gly Gly Leu Thr Tyr Arg
                245                 250                 255

Glu Ser His Leu Ala Met Glu Met Leu Ala Glu Ala Gln Leu Ile Thr
            260                 265                 270

Ser Ala Glu Phe Val Glu Val Asn Pro Ile Leu Asp Glu Arg Asn Lys
        275                 280                 285

Thr Ala Ser Val Ala Val Gly Leu Met Gly Ser Leu Phe Gly Glu Lys
    290                 295                 300

Leu Val
305

<210> SEQ ID NO 58
<211> LENGTH: 306
<212> TYPE: PRT
<213> ORGANISM: Geobacillus thermoglucosidans

<400> SEQUENCE: 58

Met Glu Arg Gly Asn Ser Val Lys Lys Val Ser Ile Ile Gly Val Pro
1               5                   10                  15

Met Asp Leu Gly Gln Thr Arg Arg Gly Val Asp Met Gly Pro Ser Ala
```

```
                        20                  25                  30
Met Arg Tyr Ala Gly Ile Ile Glu Arg Leu Glu Arg Leu His Tyr Glu
                35                  40                  45

Ile Glu Asp Leu Gly Asp Val Ser Ile Gly Lys Met Glu Trp Ser Asp
         50                  55                  60

Asp Glu Gly Leu Arg Leu Asn Leu Arg Asn Leu Lys Ala Val Ala Lys
 65                  70                  75                  80

Thr Asn Glu Lys Leu Ala Glu Met Val Asp Asp Val Val Gln Arg Gly
                85                  90                  95

Arg Phe Pro Leu Val Leu Gly Gly Asp His Ser Ile Ala Ile Gly Thr
            100                 105                 110

Leu Ala Gly Val Ala Lys His Tyr Gln Asn Leu Gly Val Ile Trp Tyr
            115                 120                 125

Asp Ala His Gly Asp Leu Asn Thr Ala Glu Thr Ser Pro Ser Gly Asn
        130                 135                 140

Ile His Gly Met Ser Leu Ala Val Cys Leu Gly Leu Gly His Pro Tyr
145                 150                 155                 160

Leu Thr Lys Ile Gly Gly Tyr Ser Pro Lys Val Lys Pro Glu Asn Val
                165                 170                 175

Val Leu Ile Gly Val Arg Ser Leu Asp Glu Gly Glu Lys Gln Leu Ile
            180                 185                 190

Arg Glu Lys Gly Ile Lys Val Tyr Thr Met His Glu Val Asp Arg Leu
        195                 200                 205

Gly Met Ala Ala Val Met Glu Glu Thr Ile Ala Tyr Leu Gln Gly Arg
    210                 215                 220

Thr Asp Gly Val His Leu Ser Leu Asp Leu Asp Gly Leu Asp Pro His
225                 230                 235                 240

Asp Ala Pro Gly Val Gly Thr Pro Val Ile Gly Gly Leu Thr Tyr Arg
                245                 250                 255

Glu Ser His Leu Ala Met Glu Met Leu Ala Glu Ala Gln Leu Ile Thr
            260                 265                 270

Ser Ala Glu Phe Val Glu Val Asn Pro Ile Leu Asp Glu Arg Asn Lys
        275                 280                 285

Thr Ala Ser Val Ala Val Gly Leu Met Gly Ser Leu Phe Gly Glu Lys
    290                 295                 300

Leu Val
305

<210> SEQ ID NO 59
<211> LENGTH: 298
<212> TYPE: PRT
<213> ORGANISM: Brevibacillus laterosporus

<400> SEQUENCE: 59

Met Asn Lys Lys Ile Ser Leu Ile Gly Val Pro Leu Asp Leu Gly Ala
1               5                   10                  15

Asp Arg Arg Gly Val Asp Met Gly Pro Ser Ala Ile Arg Tyr Ala Gly
                20                  25                  30

Val Val Lys Arg Leu Glu Gly Leu Gly Tyr Ser Val Lys Asp Leu Gly
            35                  40                  45

Asp Ile Pro Val Ile Arg Pro Glu Asn Phe Glu Glu Thr Asp Asn His
        50                  55                  60

Lys Tyr Leu Gln Gln Val Leu Glu Ala Asn Glu Arg Leu Ala Thr Lys
 65                  70                  75                  80
```

Val Ala Leu Glu Ile Glu Asn Gly Arg Phe Pro Leu Val Val Gly Gly
            85                  90                  95

Asp His Ser Ile Ala Leu Gly Thr Leu Ala Gly Val Ala Gln Thr Lys
            100                 105                 110

Lys Asn Leu Gly Val Ile Trp Phe Asp Ala His Gly Asp Ile Asn Thr
            115                 120                 125

Gly Leu Thr Ser Pro Ser Gly Asn Ile His Gly Met Pro Leu Ala Ala
            130                 135                 140

Ser Leu Gly Ile Gly His Glu Ala Leu Val Lys Ile Gly Gly Tyr Ser
145                 150                 155                 160

Pro Lys Ile Lys Pro Glu His Val Val Ile Gly Ala Arg Asp Leu
                165                 170                 175

Asp Leu Gly Glu Arg Glu Leu Ile Lys Glu Leu Gly Ile Lys Val Tyr
            180                 185                 190

Thr Met His Glu Ile Asp Arg Leu Gly Met Thr Arg Val Met Glu Glu
            195                 200                 205

Thr Ile Glu Tyr Val Thr Glu Gly Thr Asp Gly Val His Leu Ser Leu
        210                 215                 220

Asp Leu Asp Gly Leu Asp Pro Ile Tyr Ala Pro Gly Val Gly Thr Pro
225                 230                 235                 240

Val Ile Gly Gly Ile Ser Tyr Arg Glu Gly His Leu Ala Met Glu Ile
                245                 250                 255

Leu Ala Glu Ala Asn Val Leu Thr Ser Ala Glu Phe Val Glu Val Asn
            260                 265                 270

Pro Ile Leu Asp Gln Gln Asn Ala Thr Ala Ala Val Ala Val Ala Leu
            275                 280                 285

Met Ser Ser Val Phe Gly Asp Lys Leu Leu
            290                 295

<210> SEQ ID NO 60
<211> LENGTH: 299
<212> TYPE: PRT
<213> ORGANISM: Desulfotomaculum ruminis

<400> SEQUENCE: 60

Met Thr Val Glu Ile Ile Gly Val Pro Leu Asp Leu Gly Ala Asn Arg
1               5                   10                  15

Arg Gly Thr Asp Met Gly Pro Ser Ala Val Arg Tyr Ala Gly Leu Cys
            20                  25                  30

Gln Ala Leu Val Lys Met Gly Leu Gln Val Val Asp Ser Gly Asn Ile
            35                  40                  45

Asp Val Pro Val His Glu Ser Ile Lys Met Ala Asn Pro Asp Thr Ile
        50                  55                  60

Phe Leu Asp Glu Ile Leu Thr Val Cys Arg Thr Leu Ala Asn Gln Val
65                  70                  75                  80

Gln Ala Ile Leu Asp Arg Gly Asp Phe Pro Leu Val Leu Gly Gly Asp
            85                  90                  95

His Ser Ile Ala Met Gly Thr Leu Ala Gly Ile Arg Lys Ser Val Pro
            100                 105                 110

Asp Ile Gly Leu Ile Trp Phe Asp Ala His Gly Asp Phe Asn Thr Phe
            115                 120                 125

Glu Thr Ser Arg Thr Gly Asn Ile His Gly Met Pro Leu Ala Val Ala
            130                 135                 140

Thr Gly Arg Gly His Ala Lys Leu Val Gln Leu Gly Gly Leu Ser Pro
145                 150                 155                 160

```
Phe Val Gln Glu Asp Lys Thr Val Leu Ile Gly Val Arg Asp Leu Asp
                165                 170                 175

Tyr His Glu Lys Ile Ser Leu Lys Asn Ser Arg Val Lys Val Tyr Ser
            180                 185                 190

Met Lys Lys Ile Asp Glu Leu Gly Met Ala Arg Val Val Lys Glu Ala
            195                 200                 205

Ile Ala Ile Ala Gly Gln Gly Gly Ser Gly Leu His Val Ser Phe Asp
            210                 215                 220

Met Asp Val Val Asp Pro Ser Ile Ala Ser Gly Val Gly Thr Pro Val
225                 230                 235                 240

Pro Gly Gly Ile Ser Tyr Arg Glu Ala His Leu Ala Leu Glu Leu Ile
                245                 250                 255

Ala Glu Thr Lys Met Leu Arg Ser Leu Glu Ile Cys Glu Val Asn Pro
            260                 265                 270

Ile Glu Asp Arg Gly Gly Asn His Thr Ala Ser Leu Ala Val Glu Leu
            275                 280                 285

Val Thr Ser Ala Leu Gly Lys Arg Ile Phe Glu
        290                 295

<210> SEQ ID NO 61
<211> LENGTH: 299
<212> TYPE: PRT
<213> ORGANISM: Geobacillus kaustophilus

<400> SEQUENCE: 61

Met Lys Pro Ile Ser Ile Ile Gly Val Pro Met Asp Leu Gly Gln Thr
1               5                   10                  15

Arg Arg Gly Val Asp Met Gly Pro Ser Ala Met Arg Tyr Ala Gly Ile
            20                  25                  30

Ile Glu Arg Leu Glu Arg Leu His Tyr Asp Ile Glu Asp Leu Gly Asp
            35                  40                  45

Ile Pro Ile Gly Lys Ala Glu Arg Leu His Glu Gln Gly Asp Ser Arg
    50                  55                  60

Leu Arg Asn Leu Lys Ala Val Ala Glu Ala Asn Glu Lys Leu Ala Thr
65                  70                  75                  80

Ala Val Asp Gln Val Val Gln Arg Gly Arg Phe Pro Leu Val Leu Gly
                85                  90                  95

Gly Asp His Ser Ile Ala Ile Gly Thr Ile Ala Gly Val Ala Lys His
            100                 105                 110

Tyr Glu Arg Leu Gly Val Ile Trp Tyr Asp Ala His Gly Asp Val Asn
            115                 120                 125

Thr Glu Glu Thr Ser Pro Ser Gly Asn Ile His Gly Met Pro Leu Ala
            130                 135                 140

Ala Ser Leu Gly Phe Gly His Pro Ala Leu Thr Gln Ile Gly Gly Tyr
145                 150                 155                 160

Ser Pro Lys Ile Lys Pro Glu His Val Val Leu Ile Gly Val Arg Ser
                165                 170                 175

Leu Asp Glu Gly Glu Lys Lys Phe Ile Arg Glu Lys Gly Ile Lys Ile
            180                 185                 190

Tyr Thr Met His Glu Val Asp Arg Leu Gly Met Thr Arg Val Met Glu
            195                 200                 205

Glu Thr Ile Thr Tyr Leu Lys Glu Arg Thr Asp Gly Val His Leu Ser
            210                 215                 220

Leu Asp Leu Asp Gly Leu Asp Pro Ser Asp Ala Pro Gly Val Gly Thr
```

```
                225                 230                 235                 240
        Pro Val Ile Gly Gly Leu Thr Tyr Arg Glu Ser His Leu Ala Met Glu
                            245                 250                 255

Met Leu Ala Glu Ala Gln Ile Ile Thr Ser Ala Glu Phe Val Glu Val
                            260                 265                 270

Asn Pro Ile Leu Asp Glu Arg Asn Lys Thr Ala Ser Val Ala Val Ala
                            275                 280                 285

Leu Met Gly Ser Leu Phe Gly Glu Lys Leu Ile
                            290                 295

<210> SEQ ID NO 62
<211> LENGTH: 299
<212> TYPE: PRT
<213> ORGANISM: Geobacillus thermoleovorans

<400> SEQUENCE: 62

Met Lys Pro Ile Ser Ile Ile Gly Val Pro Met Asp Leu Gly Gln Thr
        1               5                   10                  15

Arg Arg Gly Val Asp Met Gly Pro Ser Ala Met Arg Tyr Ala Gly Val
                            20                  25                  30

Ile Glu Arg Leu Glu Arg Leu His Tyr Asp Ile Glu Asp Leu Gly Asp
                        35                  40                  45

Ile Pro Ile Gly Lys Ala Glu Arg Leu His Glu Gln Gly Asp Ser Arg
        50                  55                  60

Leu Arg Asn Leu Lys Ala Val Ala Glu Ala Asn Glu Lys Leu Ala Ala
        65                  70                  75                  80

Ala Val Asp Gln Val Val Gln Arg Gly Arg Phe Pro Leu Val Leu Gly
                            85                  90                  95

Gly Asp His Ser Ile Ala Ile Gly Thr Leu Ala Gly Val Ala Lys His
                            100                 105                 110

Tyr Glu Arg Leu Gly Val Ile Trp Tyr Asp Ala His Gly Asp Val Asn
                        115                 120                 125

Thr Ala Glu Thr Ser Pro Ser Gly Asn Ile His Gly Met Pro Leu Ala
        130                 135                 140

Ala Ser Leu Gly Phe Gly His Pro Ala Leu Thr Gln Ile Gly Gly Tyr
        145                 150                 155                 160

Ser Pro Lys Ile Lys Pro Glu His Val Val Leu Ile Gly Val Arg Ser
                            165                 170                 175

Leu Asp Glu Gly Glu Lys Lys Phe Ile Arg Glu Lys Gly Ile Lys Ile
                            180                 185                 190

Tyr Thr Met His Glu Val Asp Arg Leu Gly Met Thr Arg Val Met Glu
                        195                 200                 205

Glu Thr Ile Ala Tyr Leu Lys Glu Arg Thr Asp Gly Val His Leu Ser
        210                 215                 220

Leu Asp Leu Asp Gly Leu Asp Pro Ser Asp Ala Pro Gly Val Gly Thr
        225                 230                 235                 240

Pro Val Ile Gly Gly Leu Thr Tyr Arg Glu Ser His Leu Ala Met Glu
                            245                 250                 255

Met Leu Ala Glu Ala Gln Ile Ile Thr Ser Ala Glu Phe Val Glu Val
                            260                 265                 270

Asn Pro Ile Leu Asp Glu Arg Asn Lys Thr Ala Ser Val Ala Val Ala
                            275                 280                 285

Leu Met Gly Ser Leu Phe Gly Glu Lys Leu Met
                            290                 295
```

<210> SEQ ID NO 63
<211> LENGTH: 299
<212> TYPE: PRT
<213> ORGANISM: Geobacillus thermodenitrificans

<400> SEQUENCE: 63

Met Lys Pro Ile Ser Ile Gly Val Pro Met Asp Leu Gly Gln Thr
1               5                   10                  15

Arg Arg Gly Val Asp Met Gly Pro Ser Ala Ile Arg Tyr Ala Gly Val
            20                  25                  30

Ile Glu Arg Leu Glu Arg Leu His Tyr Asp Ile Glu Asp Leu Gly Asp
        35                  40                  45

Ile Pro Ile Gly Lys Val Glu Arg Leu His Glu Gln Gly Ala Ser Gln
    50                  55                  60

Leu Arg Asn Leu Lys Ala Val Ala Glu Ala Asn Glu Lys Leu Ala Thr
65                  70                  75                  80

Ala Val Asp Glu Val Val Lys Arg Gly Arg Phe Pro Leu Val Leu Gly
                85                  90                  95

Gly Asp His Ser Ile Ala Ile Gly Thr Leu Ala Gly Val Ala Lys His
            100                 105                 110

Tyr Glu Arg Leu Gly Val Ile Trp Tyr Asp Ala His Gly Asp Val Asn
        115                 120                 125

Thr Glu Glu Thr Ser Pro Ser Gly Asn Ile His Gly Met Pro Leu Ala
    130                 135                 140

Ala Ser Leu Gly Phe Gly His Pro Ala Leu Thr Gly Ile Gly Gly Tyr
145                 150                 155                 160

Ser Pro Lys Val Lys Pro Glu His Val Val Leu Ile Gly Val Arg Ser
                165                 170                 175

Leu Asp Asp Gly Glu Lys Lys Phe Ile Arg Glu Lys Gly Ile Lys Ile
            180                 185                 190

Tyr Thr Met His Glu Val Asp Arg Leu Gly Met Thr Lys Val Met Glu
        195                 200                 205

Glu Thr Ile Ala Tyr Leu Lys Glu Arg Thr Asp Gly Val His Leu Ser
    210                 215                 220

Leu Asp Leu Asp Gly Leu Asp Pro Ser Asp Ala Pro Gly Val Gly Thr
225                 230                 235                 240

Pro Val Ile Gly Gly Leu Thr Tyr Arg Glu Ser His Leu Ala Met Glu
                245                 250                 255

Met Leu Ala Glu Ala Gln Ile Ile Thr Ser Ala Glu Phe Val Glu Val
            260                 265                 270

Asn Pro Ile Leu Asp Glu Arg Asn Lys Thr Ala Ser Val Ala Val Ala
        275                 280                 285

Leu Met Gly Ser Leu Phe Gly Glu Lys Leu Val
    290                 295

<210> SEQ ID NO 64
<211> LENGTH: 302
<212> TYPE: PRT
<213> ORGANISM: Staphylococcus aureus

<400> SEQUENCE: 64

Met Thr Lys Thr Lys Ala Ile Asp Ile Ile Gly Ala Pro Ser Thr Phe
1               5                   10                  15

Gly Gln Arg Lys Leu Gly Val Asp Leu Gly Pro Thr Ala Ile Arg Tyr
            20                  25                  30

```
Ala Gly Leu Ile Ser Arg Leu Lys Gln Leu Asp Leu Asp Val Tyr Asp
            35                  40                  45

Lys Gly Asp Ile Lys Val Pro Ala Val Asn Ile Glu Lys Phe His Ser
 50                  55                  60

Glu Gln Lys Gly Leu Arg Asn Tyr Asp Glu Ile Ile Asp Val Asn Gln
 65                  70                  75                  80

Lys Leu Asn Lys Glu Val Ser Ala Ser Ile Glu Asn Asn Arg Phe Pro
                 85                  90                  95

Leu Val Leu Gly Gly Asp His Ser Ile Ala Val Gly Ser Val Ser Ala
                100                 105                 110

Ile Ser Lys His Tyr Asn Asn Leu Gly Val Ile Trp Tyr Asp Ala His
                115                 120                 125

Gly Asp Leu Asn Ile Pro Glu Glu Ser Pro Ser Gly Asn Ile His Gly
        130                 135                 140

Met Pro Leu Arg Ile Leu Thr Gly Glu Gly Pro Lys Glu Leu Leu Glu
145                 150                 155                 160

Leu Asn Ser Asn Val Ile Lys Pro Glu Asn Ile Val Leu Ile Gly Met
                165                 170                 175

Arg Asp Leu Asp Lys Gly Glu Arg Gln Phe Ile Lys Asp His Asn Ile
                180                 185                 190

Lys Thr Phe Thr Met Ser Asp Ile Asp Lys Leu Gly Ile Lys Glu Val
                195                 200                 205

Ile Glu Asn Thr Ile Glu Tyr Leu Lys Ser Arg Asn Val Asp Gly Val
        210                 215                 220

His Leu Ser Leu Asp Val Asp Ala Leu Asp Pro Leu Glu Thr Pro Gly
225                 230                 235                 240

Thr Gly Thr Arg Val Leu Gly Gly Leu Ser Tyr Arg Glu Ser His Phe
                245                 250                 255

Ala Leu Glu Leu Leu His Gln Ser His Leu Ile Ser Ser Met Asp Leu
                260                 265                 270

Val Glu Val Asn Pro Leu Ile Asp Ser Asn Asn His Thr Ala Glu Gln
                275                 280                 285

Ala Val Ser Leu Val Gly Thr Phe Phe Gly Glu Thr Leu Leu
        290                 295                 300

<210> SEQ ID NO 65
<211> LENGTH: 338
<212> TYPE: PRT
<213> ORGANISM: Halophilic archaeon

<400> SEQUENCE: 65

Met Ser Arg Gly Pro Asp Arg Ser Arg Ala Ala Glu Phe Arg Asn Arg
1                5                  10                  15

Thr Thr Gly Ala Asp Val Glu Leu Ala Tyr Ala Gly Ile Asp Thr Phe
                20                  25                  30

Leu Lys Ala Asp Leu Ala Glu Ile Asp Val Gly Gly Ala Asp Ala
            35                  40                  45

Ala Val Leu Gly Ala Pro Tyr Asp Gly Ala Val Ser Asn Arg Pro Gly
 50                  55                  60

Ala Arg Tyr Gly Pro Asp Ala Val Arg Glu Ala Ser Ala Trp Trp Ala
 65                  70                  75                  80

Tyr Leu Ser Gly Tyr Lys Gly Gly Leu Thr Asn Met Arg Thr Gly Glu
                 85                  90                  95

Gln Val Asp Tyr Gly Asp Leu Ser Val Val Asp Thr Gly Asp Val Pro
                100                 105                 110
```

```
Val Phe Pro Met Asp Cys Glu Thr Thr Ala Asp Ser Ile Ala Ala His
        115                 120                 125

Val Ala Thr Ile Ala Ala Gln Gly Thr Met Pro Val Leu Ile Gly Gly
        130                 135                 140

Asp His Tyr Cys Thr Phe Pro Ala Val Arg Gly Phe Ala Glu Gly Ala
145                 150                 155                 160

Asp Leu Asp Ser Val Gly Leu Val Gln Ile Asp Ala His Thr Asp Thr
        165                 170                 175

Val Ala Glu Ser Ala Val Phe Gly Glu His Phe His Gly Ser Ser Thr
        180                 185                 190

His His Ile Ala Asp Ser Glu Phe Ala Asp Tyr Ala Asn Val Ser Gln
        195                 200                 205

Val Gly Ile Arg Gly Tyr Glu Ser Pro Ala Phe Phe Glu Phe Ala Asp
        210                 215                 220

Glu Thr Gly Leu Asn Leu Phe Thr Met Asn Glu Val Asn Glu Arg Gly
225                 230                 235                 240

Ile Gly Pro Val Thr Glu Ala Ala Val Glu Ala Ala Ala Asp Gly Thr
        245                 250                 255

Asp Ala Val Tyr Val Thr Phe Asp Ile Asp Ser Val Asp Pro Ser Asp
        260                 265                 270

Ala Pro Gly Thr Gly Thr Pro Glu Pro Gly Gly Leu Ser Ala Asp Gln
        275                 280                 285

Ala Leu Thr Val Met Glu Thr Leu Gly Ala His Asp Ser Val Ala Ala
        290                 295                 300

Ala Asp Leu Met Glu Val Ala Pro Asp His Pro Ala Gly Asn Thr
305                 310                 315                 320

Ser Arg Leu Ala Ala Asn Leu Leu Val Ala Leu Leu Glu Arg Lys Phe
        325                 330                 335

Ala Val

<210> SEQ ID NO 66
<211> LENGTH: 319
<212> TYPE: PRT
<213> ORGANISM: Halopiger xanaduensis

<400> SEQUENCE: 66

Met Asn Thr Asn Ala Thr Val Arg Ile Ile Gly Ala Pro Met Asp Tyr
1               5                   10                  15

Gly Ala Asn Arg Arg Gly Val Asp Met Gly Pro Ser Ala Ile Arg Tyr
            20                  25                  30

Ala Gly Leu Ala Asp Glu Leu Glu Arg Ala Ser Val Ala Pro Val Asp
        35                  40                  45

Asp Gly Asp Leu Ser Met Pro Arg Ala Glu Glu Ile Asp Pro Asp Ala
    50                  55                  60

Asp Asp Ala Thr Gly Leu Glu Ser Thr Gly Gly Glu Ser Ala Gly Val
65                  70                  75                  80

Glu Asn Ala Lys Phe Leu Pro Glu Ile Glu Ser Val Asn Ala Arg Leu
            85                  90                  95

Ala Asp Arg Val Ala Glu Thr Leu Ala Asp Gly Glu Phe Pro Leu Val
            100                 105                 110

Leu Gly Gly Asp His Ser Val Ala Ile Gly Ser Leu His Gly Ser Ala
        115                 120                 125

Arg Asp Ala Asp Val Gly Ala Ile Trp Phe Asp Ala His Ala Asp Leu
        130                 135                 140
```

```
Asn Thr Pro Glu Thr Ser Pro Ser Gly Asn Val His Gly Met Pro Leu
145                 150                 155                 160

Gly Ala Ala Leu Gly Arg Gly Val Phe Gly Asp Met Asp Trp Ala His
                165                 170                 175

Ser Pro Arg Leu Arg Glu Glu Ser Val Ala Tyr Val Gly Leu Arg Ser
            180                 185                 190

Ile Asp Glu Arg Glu Arg Glu Leu Val Arg Glu Ser Glu Met Thr Ala
            195                 200                 205

Phe Thr Met Ser Asp Ile Asp Gln Arg Gly Met Thr Ala Val Val Glu
210                 215                 220

Asp Ala Leu Ala Val Ala Thr Asp Gly Thr Asp Gly Ile His Val Ser
225                 230                 235                 240

Leu Asp Leu Asp Met Ile Asp Pro Lys Ala Ala Pro Gly Val Gly Thr
                245                 250                 255

Pro Val Arg Gly Gly Val Thr Tyr Arg Glu Ala His Ala Ala Leu Glu
            260                 265                 270

Ala Val Ser Arg Arg His Asp Arg Asp Gly Ile Leu Arg Ser Met Asp
            275                 280                 285

Val Val Glu Val Asn Pro Ile Leu Asp Glu Ala Asn Glu Thr Ala Ala
290                 295                 300

Leu Ala Ala Glu Leu Thr Ala Ser Ala Phe Gly Lys Arg Ile Leu
305                 310                 315

<210> SEQ ID NO 67
<211> LENGTH: 334
<212> TYPE: PRT
<213> ORGANISM: Natrialba magadii

<400> SEQUENCE: 67

Met Ser Asp Gln His Pro Ala Ala Ala Phe Arg Glu Ser Val Glu Gly
1               5                   10                  15

Ala Asn Val Glu Leu Ala Tyr Ala Gly Ala Lys Thr Phe Leu Lys Gly
                20                  25                  30

Glu Met Arg Asp Val Gly Ala Val Ser Asp Val Asp Ala Ala Thr Phe
            35                  40                  45

Gly Val Pro Tyr Asp Gly Ala Val Ser Asn Arg Pro Gly Ala Arg Tyr
        50                  55                  60

Gly Pro Gln Ala Ile Arg Arg Ala Ser Gly Trp Trp Ala Tyr Leu Ser
65                  70                  75                  80

Asp Tyr Lys Gly Gly Leu Thr Asn Met Gln Thr Gly Lys Gln Val Asn
                85                  90                  95

Phe Asp Asp Leu Thr Val Ala Asp Cys Gly Asp Ala Pro Ile Phe Pro
            100                 105                 110

Met Asp Ser Glu Thr Thr Ala Glu Ser Ile Thr Ala His Met Ala Thr
        115                 120                 125

Val Ala Ser Gln Thr Phe Pro Val Met Leu Gly Gly Asp His Tyr Cys
    130                 135                 140

Thr Phe Pro Ala Leu Arg Gly Phe Ala Glu Gly Ala His Asp Thr
145                 150                 155                 160

Val Gly Phe Val Gln Ile Asp Ala His Thr Asp Thr Thr Ser Glu Ser
                165                 170                 175

Pro Val Phe Gly Thr Asp Phe His Gly Ser Ser Thr Ser Leu Ile Ala
            180                 185                 190

Asn Ser Glu Tyr Thr Asp Tyr Glu Asn Val Ser Gln Val Gly Ile Arg
```

-continued

```
            195                 200                 205
Gly Tyr Glu Ser Pro Glu Phe Phe Glu Phe Ala Glu Glu Thr Gly Leu
        210                 215                 220

Asn Leu Tyr Thr Met Arg Asp Val Glu Asp Gln Gly Ile Thr Ser Ala
225                 230                 235                 240

Val Ala Asp Ala Val Ala Ala Ala Ala Glu Gly Thr Asp Ala Val Tyr
                245                 250                 255

Val Ser Phe Asp Ile Asp Ala Val Asp Pro Ser Val Ala Pro Gly Thr
            260                 265                 270

Gly Thr Pro Val Pro Gly Gly Leu Thr Pro His Gln Ala Leu Lys Thr
        275                 280                 285

Met Glu Val Leu Gly Glu Thr Asp Asp Val Gly Ala Val Asp Met Met
    290                 295                 300

Glu Val Ala Pro Arg Tyr Asp Ser Asp Glu Gly Thr Gln Arg Leu Ala
305                 310                 315                 320

Ala Tyr Leu Leu Val Thr Leu Leu Glu Arg Lys Phe Ala Glu
                325                 330
```

SITE-DIRECTED PEGYLATION OF ARGINASES AND THE USE THEREOF AS ANTI-CANCER AND ANTI-VIRAL AGENTS

CROSS REFERENCE TO RELATED APPLICATIONS

This is a continuation-in-part application claiming benefit from U.S. Non-Provisional patent application Ser. No. 12/732,188 filed Mar. 26, 2010, which claims priority from U.S. Provisional Patent Application No. 61/163,863 filed Mar. 26, 2009, and the content of which is incorporated herewith in its entirety by reference.

FIELD OF THE INVENTION

The present invention relates to the modification of an arginase for the purpose of increasing the enzyme's serum or circulating half-life and improving its pharmacokinetic properties, in vivo biological activity, stability, and reducing the immune reaction (immunogenicity) to the enzyme in vivo. More specifically, the present invention relates to a site-specific covalent conjugation of polyethylene glycol (PEG) to an arginase through genetically modifying the gene encoding the arginase to produce single or double site-specific pegylated arginase. These site-specific pegylated arginases become effective treatment means for a number of arginine-dependent diseases, such as, for example, various cancers and human immunodeficiency virus (HIV) infection.

BACKGROUND OF THE INVENTION

Arginase

Arginase is a manganese metalloenzyme containing a metal-activated hydroxide ion, a critical nucleophile in metalloenzymes that catalyze hydrolysis or hydration reactions. Arginase converts naturally occurring arginine into ornithine and urea. The enzyme exits in many living organisms, including bacteria and humans (Jenkinson et al., 1996, Comp Biochem Physiol B Biochem Mol Biol, 114:107-32).

Pegylation of Arginase

Arginase may be used as a therapeutic agent and administered parenterally for various indications. However, parenterally administrated arginase, which is a protein, may be immunogenic and typically has a short pharmacological half-life. Consequently, it can be difficult to achieve therapeutically useful blood levels of the proteins in patients. These problems may be overcome by conjugating the proteins to polymers such as polyethylene glycol (PEG).

Covalent attachment of the inert, non-toxic, biodegradable polymer PEG, to molecules has important applications in biotechnology and medicine. Pegylation of biologically and pharmaceutically active proteins has been reported to improve pharmacokinetics, resulting in sustained duration, improve safety (e.g. lower toxicity, immunogenicity and antigenicity), increase efficacy, decrease dosing frequency, improve drug solubility and stability, reduce proteolysis, and facilitate controlled drug release (Roberts et al., 2002, Adv Drug Deliv Rev, 54:459-76; Harris & Chess, 2003, Nat Rev Drug Discov, 2:214-221).

PEG-protein conjugates produced by conventional methods in the art contain heterogeneous species, each being attached with a variable number of PEG molecules, ranging from zero to the number of amino groups that the protein has. Even for species that has the same number of PEG molecule attached, the site of attachment on the protein may vary from species to species. Such non-specific pegylation, however, can result in conjugates that are partially or virtually inactive. Reduction of activity may be caused by shielding the protein's active receptor binding domain when the PEG is attached at an improper site. Thus, there is a clear need for a better way of producing homogeneously pegylated protein molecules which retain the activity of the parent protein and making possible the administration of correct and consistent dosages necessary for clinical uses.

Cancer Treatment Via Amino Acid Deprivation

Amino acid deprivation therapy is an effective means for the treatment of some cancers. Although normal cells do not require arginine, many cancer cell lines are auxotrophic for this amino acid. Many lines of evidence have shown that in vitro arginine depletion, either with an arginine-degrading enzyme or by using an arginine-deficient medium, leads to rapid destruction of a wide range of cancer cells (Scott et al., 2000, Br J Cancer, 83:800-10). But direct use of enzymes, which are proteins, has problems of immunogenicity, antigenicity and short circulating half-life.

Inhibition of Virus by Arginine Deprivation

Viral infections are among the leading causes of death with millions of deaths each year being directly attributable to several viruses including hepatitis and human immunodeficiency virus (HIV). However, there are several problems with current anti-viral therapies. First, there are relatively few effective antiviral drugs. Many of the existing anti-viral agents cause adverse or undesirable side-effects. Most effective therapies (such as vaccination) are highly specific for only a single strain of virus. Frequently the virus undergoes mutation such that it becomes resistant to either the drug or vaccine. There is a need for methods for inhibiting viral replication which do not have the problems associated with the prior art.

Many studies over the last 30 years have demonstrated that extracellular arginine is required for viral replication in vitro. Historically this has been accomplished by making tissue culture media deficient in arginine and dialyzing the serum used as a supplement in order to achieve arginine free medium. Using this methodology to achieve arginine deprivation results in inhibition of replication of a large number of diverse families of viruses including: adenovirus (Rouse et al., 1963, Virology, 20:357-365), herpes virus (Tankersley, 1964, J Bacteriol, 87: 609-13).

Human Immunodeficiency Virus (HIV)

Acquired immune deficiency syndrome (AIDS) is a fatal disease, reported cases of which have increased dramatically within the past several years. The AIDS virus was first identified in 1983. It has been known by several names and acronyms. It is the third known T-lymphotropic virus (HTLV-III), and it has the capacity to replicate within cells of the immune system, causing profound cell destruction. The AIDS virus is a retrovirus, a virus that uses reverse transcriptase during replication. Two distinct families of HIV have been described to date, namely HIV-1 and HIV-2. The acronym "HIV" is used herein to refer to human immunodeficiency viruses generically. HIV replication is believed to be arginine-dependent, depletion of which would thus inhibit HIV replication.

SUMMARY OF THE INVENTION

According to the present invention, various native arginases are modified in order to promote attachment of a single or two PEG polymer(s). Although most proteins do not possess a specific native site or a free cysteine residue for the attachment of PEG polymer(s), the present invention has solved this problem by genetically engineering/mutating various arginase proteins to insert free cysteine residue(s) for site-directed mono- or double-pegylation. Alternatively, other arginase proteins may contain more free cysteine residues than desired or have one or more of them at undesirable positions. The present invention has solved this problem by genetically removing these free cysteine residues from the enzyme, leaving only the desirable site(s) for attachment of the PEG moiety.

Note that for both aspects of the present invention, site selection is carefully engineered to ensure that the attached PEG molecule does not interfere with the active binding site for the various arginases.

The selected pegylation sites are far away from the active binding site, and generally exposed to solvent to allow reaction with thiol-specific PEG molecules. To prevent disruption of tertiary structure or loss of protein structure, utilizing of the cysteine molecules involved in native disulfide bonds are avoided. Instead, novel "free" cysteine residues can be introduced/engineered or cysteine residues that are not involved in a disulfide bond can be used for thiol pegylation in arginases to avoid disulfide scrambling and protein misfolding.

In particular, an object of the present invention is to provide novel PEG-arginase conjugates substantially homogeneous and having PEG moiety covalently bound to specific sites at the arginase molecule. Two preferred embodiments of the present invention are $Cys^{45}$-human arginase I (HAI) and $Cys^{161}$-Bacillus caldovelox arginase (BCA).

Another object of the present invention is to provide a method of producing site-directed, mono- or double-pegylated arginase conjugates, which have potent anti-cancer and anti-viral effects. One particular embodiment of the present invention comprises three general steps. The first step is a genetically modification of a gene encoding for an arginase so that the resulting arginase will have0 one to two free cysteine residue(s) so that the PEG moiety can attach to the enzyme at these specific intended site(s).

The second step is expressing the modified gene in a chosen system to produce desired arginase. The host where the modified gene is expressed may be human cells or tissues, or other organisms including, for example, a bacterial cell, a fungal cell, a plant cell, an animal cell, an insect cell, a yeast cell, or a transgenic animal. The third step is conjugation between the free cysteine residue(s) of the modified arginase and a maleimide group (MAL) of a PEG compound, resulting in a covalent bond between the PEG compound and the free cysteine(s) of the modified arginase.

Another object of the present invention is to provide a method of treating viral infection via arginine depletion. In one embodiment, the method of treatment employs homogeneous mono- or double-pegylated arginase to inhibit viruses' replication.

Another object of the present invention is to provide a method of treating and/or preventing replication of human immunodeficiency virus (HIV). In one embodiment, the method of treatment employs homogeneous mono- or double-pegylated arginase to inhibit HIV's replication.

Another object of the present invention is to provide a method of enhancing arginase's enzymatic activity by replacing the valine at position 20 of Bacillus caldovelox arginase (or the corresponding position in HAI and other arginases) with another amino acid residue, for example, proline.

Still another object of the present invention is to provide a method of enhancing arginase's enzymatic activity, which is accomplished by replacing the native metal cofactor manganese with cobalt.

The various features of novelty which characterize the present invention are pointed out with particularity in the claims annexed to and forming a part of this disclosure. For a better understanding of the present invention, its operating advantages, and specific objects attained by its use, reference should be made to the drawings and the following description in which there are illustrated and described preferred embodiments of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows (A) the nucleotide sequence of unmodified human arginase I (SEQ ID NO: 1); (B) a mutated nucleotide sequence of the human arginase I designed for site-directed pegylation (SEQ ID NO: 2) according to the present invention; (C) the nucleotide sequence of unmodified Bacillus caldovelox arginase (SEQ ID NO: 3); and (D) a mutated nucleotide sequence of Bacillus caldovelox arginase designed for site-directed pegylation (SEQ ID NO: 4) according to the present invention.

FIG. 2 shows (A) the amino acid sequence of the unmodified human arginase I (SEQ ID NO: 5); (B) a modified amino acid sequence of human arginase I designed for $Cys^{45}$ site-directed pegylation (SEQ ID NO: 6) according to the present invention; (C) the amino acid sequence of unmodified Bacillus caldovelox arginase (SEQ ID NO: 7); and (D) a modified amino acid sequence of Bacillus caldovelox arginase designed for $Cys^{161}$ site-directed pegylation (SEQ ID NO: 8) according to the present invention.

FIG. 3 shows (A) the nucleotide and amino acid sequences of the human arginase I mutant (C168S/C303S) designed for $Cys^{45}$ site-directed pegylation (SEQ ID NOs: 9 and 10); (B) the alignment of the nucleotide and amino acid sequences of the 6×His-tagged human arginase I mutant (C168S/C303S) designed for-$Cys^{45}$ site-directed pegylation (SEQ ID NOs: 11 and 12); (C) the nucleotide and amino acid sequences of the Bacillus caldovelox arginase mutant (S161C) designed for $Cys^{161}$ site-directed pegylation (SEQ ID NOs: 13 and 14); and (D) the alignment of the nucleotide and amino acid sequences of the 6×His-tagged Bacillus caldovelox arginase mutant (S161C) designed for $Cys^{161}$ site-directed pegylation (SEQ ID NOs: 15 and 16), where the box close to the C-terminus represents the 6×His-tag encoding codons.

FIG. 19 shows the alignment of certain residues in arginases across various species: (A) Group 1 organisms that possess cysteine equivalent to Cys-45 in human arginase; corresponding sequence identifiers of the Group 1 organisms are as follows: *Capra hircus* arginase I (SEQ ID NO: 23), *Heterocephalus glaber* arginase I (SEQ ID NO: 24), *Bos taurus* arginase I (SEQ ID NO: 25), *Sus scrofa* arginase I (SEQ ID NO: 26), *Plecoglossus altivelis* arginase I (SEQ ID NO: 27), *Salmo salar* arginase I (SEQ ID NO: 28), *Oncorhynchus mykiss* arginase I (SEQ ID NO: 29), *Osmerus mordax* arginase I (SEQ ID NO: 30), *Hyriopsis cumingii* arginase I (SEQ ID NO: 31), *Rattus norvegicus* arginase II (SEQ ID NO: 32), *Mus musculus* arginase II (SEQ ID NO: 33), human arginase II (SEQ ID NO: 34), *Bos taurus* arginase II (SEQ ID NO: 35), *Heterocephalus glaber* arginase II (SEQ ID NO: 36), *Pan troglodytes* arginase II (SEQ ID NO: 37), *Oryctolagus cuniculus* arginase II (SEQ ID NO: 38), *Delftia* arginase (SEQ ID NO: 39), *Bacillus coagulans* arginase (SEQ ID NO: 40), *Hoeflea phototrophica* arginase (SEQ ID NO: 41) and *Roseiflexus castenholzii* arginase (SEQ ID NO: 42); (B) Group 2 organisms that possess Serine equivalent to Ser-161 in *Bacillus caldovelox* arginase; corresponding sequence identifiers of the Group 2 organisms are as follows: *Bacillus methanolicus* (SEQ ID NO: 43), *Bacillus sp.* NRRL B-14911 (SEQ ID NO: 44), *Planococcus donghaensis* (SEQ ID NO: 45), *Paenibacillus dendritiformis* (SEQ ID NO: 46), *Desmospora* sp. (SEQ ID NO: 47), *Methylobacter tundripaludum* ((SEQ ID NO: 48), *Stenotrophomonas* sp. (SEQ ID NO: 49), *Microbacterium laevaniformans* (SEQ ID NO: 50), *Porphyromonas uenonis* (SEQ ID NO: 51), *Agrobacterium* sp. (SEQ ID NO: 52), *Octadecabacter arcticus* (SEQ ID NO: 53), *Agrobacterium tumefaciens* (SEQ ID NO: 54), *Anoxybacillus flavithermus* (SEQ ID NO: 55), *Bacillus pumilus* (SEQ ID NO: 56), *Geobacillus thermoglucosidasius* (SEQ ID NO: 57), *Geobacillus thermoglucosidans* (SEQ ID NO: 58), *Brevibacillus laterosporus* (SEQ ID NO: 59), *Desulfotomaculum ruminis* (SEQ ID NO: 60), *Geobacillus kaustophilus* (SEQ ID NO: 61), *Geobacillus thermoleovorans* (SEQ ID NO: 62), *Geobacillus thermodenitrificans* (SEQ ID NO: 63), *Staphylococcus aureus* (SEQ ID NO: 64), Halophilic archaeon DL31 (SEQ ID NO: 65), *Halopiger xanaduensis* (SEQ ID NO: 66) and *Natrialba magadii* (SEQ ID NO: 67); (C) Group 3 organisms that possess two cysteines equivalent to Cys-45 and Cys-168 of human arginase; corresponding sequence identifiers of the Group 3 organisms are as follows: *Capra hircus* arginase I (SEQ ID NO: 23), *Heterocephalus glaber* arginase I (SEQ ID NO: 24), *Bos taurus* arginase I (SEQ ID NO: 25), *Sus scrofa* arginase I (SEQ ID NO: 26), *Plecoglossus altivelis* arginase I (SEQ ID NO: 27), *Salmo salar* arginase I (SEQ ID NO: 28), *Oncorhynchus mykiss* arginase I (SEQ ID NO: 29), *Osmerus mordax* arginase I (SEQ ID NO: 30), *Hyriopsis cumingii* arginase I (SEQ ID NO: 31), *Rattus norvegicus* arginase II (SEQ ID NO: 32), *Mus* musculus arginase II (SEQ ID NO: 33), human arginase II (SEQ ID NO: 34), *Bos taurus* arginase II (SEQ ID NO: 35), *Heterocephalus glaber* arginase II (SEQ ID NO: 36), *Pan troglodytes* arginase II (SEQ ID NO: 37), *Oryctolagus cuniculus* arginase II (SEQ ID NO: 38); (D) Group 4 organisms that possess Tyrosine and Serine equivalent to Tyr-41 and Ser-161 of *Bacillus caldovelox* arginase; corresponding sequence identifiers of the Group 4 organisms are as follows: *Bacillus methanolicus* (SEQ ID NO: 43), *Desmospora* sp. (SEQ ID NO: 47), *Geobacillus thermoglucosidasius* (SEQ ID NO: 57), *Geobacillus thermoglucosidans* (SEQ ID NO: 58), *Brevibacillus laterosporus* (SEQ ID NO: 59), *Geobacillus kaustophilus* (SEQ ID NO: 61), *Geobacillus thermoleovorans* (SEQ ID NO: 62), *Geobacillus thermodenitrificans* (SEQ ID NO: 63).

FIG. 20 shows (A) the locations of Ser-161 within the three-dimensional structure of *Bacillus caldovelox* arginase; (B) its equivalent position Cys-168 within human arginase and (C) their overlay view.

FIG. 21 shows (A) the locations of Cys-45 within the three-dimensional structure of human arginase; (B) its equivalent position Tyr-41 within *Bacillus caldovelox* arginase and (C) their overlay view.

Figure 22:
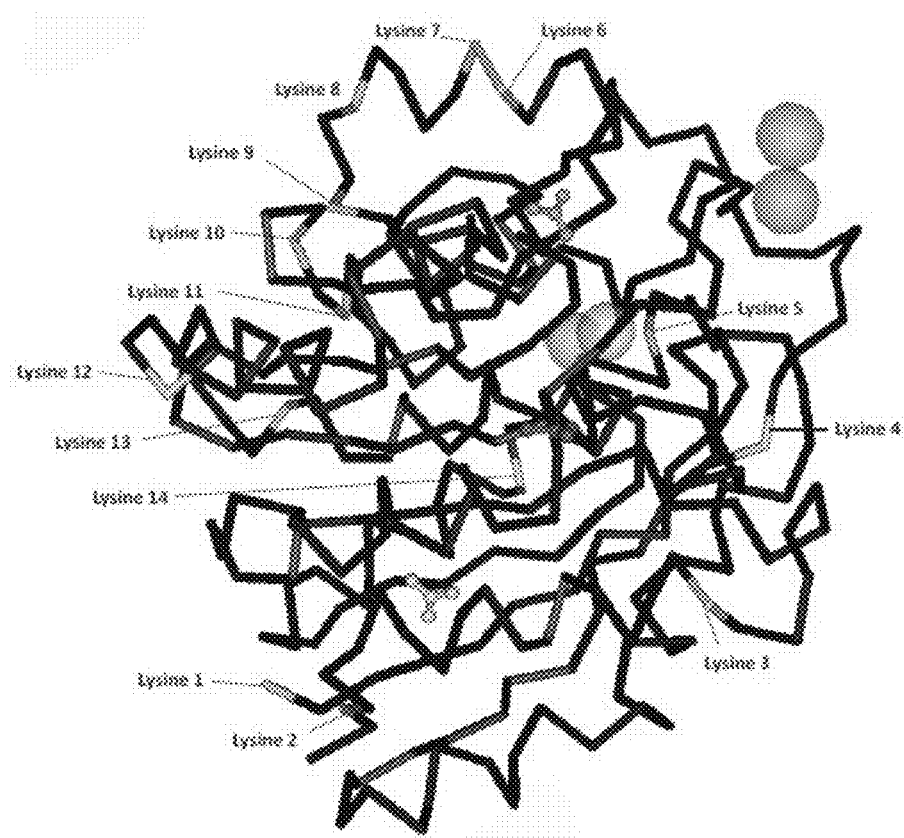

FIG. 22 depicts lysine positions on *Bacillus caldovelox* arginase.

Figure 23:
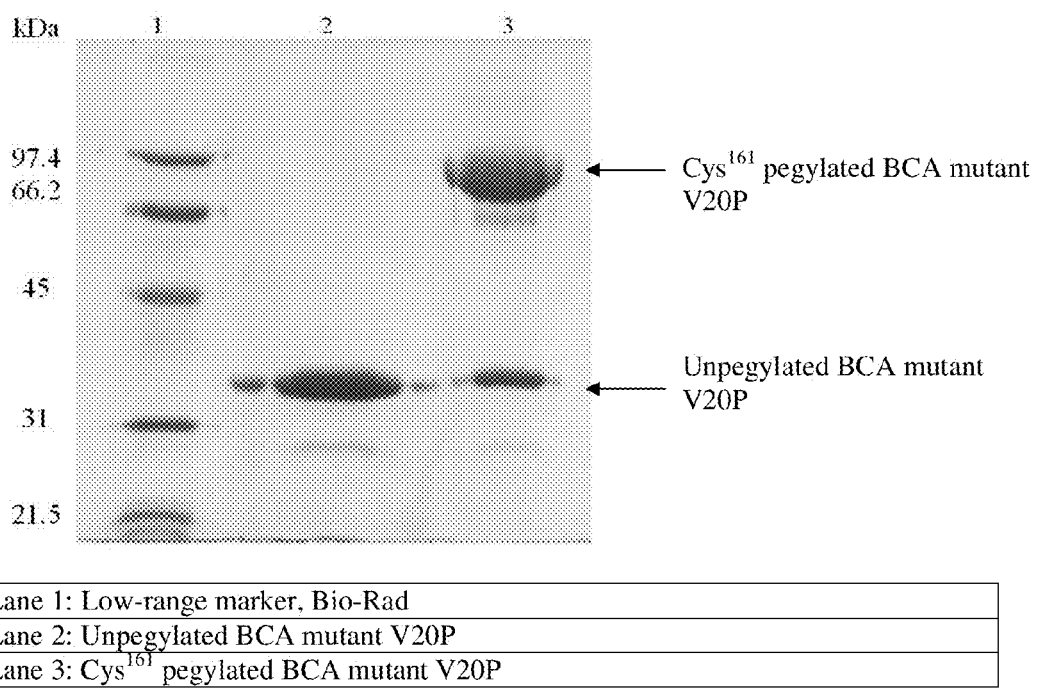

FIG. 23 shows the SDS-PAGE analysis of the unpegylated BCA mutant V20P and the $Cys^{161}$ pegylated BCA mutant V20P (Lane 1: protein molecular weight marker; Lane 2: unpegylated BCA mutant V20P; and Lane 3: $Cys^{161}$ pegylated BCA mutant V20P).

DETAILED DESCRIPTION OF THE INVENTION

According to the present invention, site-specific pegylation of various arginases can be controlled by controlling the availability of sites where pegylation can occur. These sites are selected such that the pegylation does not block the active bonding site while retaining the arginase activity. Although typically a single site is provided for pegylation, more than one carefully engineered site can be provided depending upon the species of arginase.

Further, the present inventors have determined that alignment of human and *Bacillus caldovelox* arginase sequences with sequences from other species revealed a high degree of conservation across many species in the regions where successful pegylation has been performed in human and *Bacillus caldovelox* arginases (FIGS. 19, 20, 21 and 22). For those arginase sequences that possess an equivalent of Cys-45 (found in human arginase) or Ser-161 (found in *Bacillus caldovelox* arginase), it is determined that the site-specific arginase pegylation for human arginase or *Bacillus caldovelox* arginase can be extended to those additional species. Thus, as discussed below, those additional species are genetically engineered for the site-specific pegylation as described below for the human arginase and *Bacillus caldovelox* arginase.

Cloning of Human Arginase I Gene (HAI)

The gene sequence of human arginase I is shown in FIG. 1A (SEQ ID NO: 1). The encoding gene for 6×His-tagged human arginase I (HAI) is generated by polymerase chain reaction (PCR) from the pAED4/HAI plasmid using the following oligonucleotides to generate an NdeI site at 5'-end and BamHI site at 3'-end. Primer HuAr07-F: 5' GAT.ATA.CAT.ATGCAT.CAC.CAT.CAC 3' (SEQ ID NO: 17) and Primer HuAr08-R: 5' AGT.GCA.GGA.TCC.TTA.CTT.AGG.TGG.GTT.AAG.GTA.GTC 3' (SEQ ID NO: 18). The PCR product is cut with NdeI and BamHI and subcloned into pET3a expression plasmid vector (Strategene).

The pET3a *E. coli* expression plasmid vector contains a T7 promoter. The T7 promoter is positioned upstream from the gene 10 leader fragment. The correct sequence is confirmed by DNA sequencing the entire coding region for human arginase I (FIG. 1A). This plasmid is referred to as pET3a/HAI.

Cloning of *Bacillus caldovelox* Arginase Gene (BCA)

The gene sequence of *Bacillus caldovelox* arginase is shown in FIG. 1C (SEQ ID NO: 3). The encoding gene for 6×His-tagged *Bacillus caldovelox* arginase (BCA) is cut from the pUC57/BCA plasmid using NdeI and BamHI restriction enzymes. The insert fragment is subcloned into pET3a expression plasmid vector (Strategene).

The correct sequence is confirmed by sequencing the entire coding region for *Bacillus caldovelox* arginase (FIG. 1C). This plasmid is referred to as pET3a/BCA.

Mutagenesis of HAI

The plasmid pET3a/HAI is used as a template for site-directed mutagenesis according to the QuikChange® site-directed mutagenesis kit (Strategene). The codons for $Cys^{168}$ and $Cys^{303}$ residues are mutated to the codons for $Ser^{168}$ and $Ser^{303}$ respectively using the following pairs of mutagenic primers (SEQ ID NO: 19, 20, 21, and 22, respectively):
Codon for $Cys^{168}$ being mutated to codon for $Ser^{168}$:

```
Primer HuAr01-F:
                                    (SEQ ID No. 19)
5' GGG.TGA.CTC.CCT.CTA.TAT.CTG.CCA.AGG 3';

Primer HuAr02-R:
                                    (SEQ ID No. 20)
5' CCT.TGG.CAG.ATA.TAG.AGG.GAG.TCA.CCC 3';
and
```

Codon for $Cys^{303}$ being mutated to codon for $Ser^{303}$:

```
Primer HuAr03-F:
                                    (SEQ ID No. 21)
5' GCA.ATA.ACC.TTG.GCT.TCT.TTC.GGA.CTT.GC 3';

Primer HuAr04-R:
                                    (SEQ ID No. 22)
5' GCA.AGT.CCG.AAA.GAA.GCC.AAG.GTT.ATT.GC 3'.
```

Figure 4A:
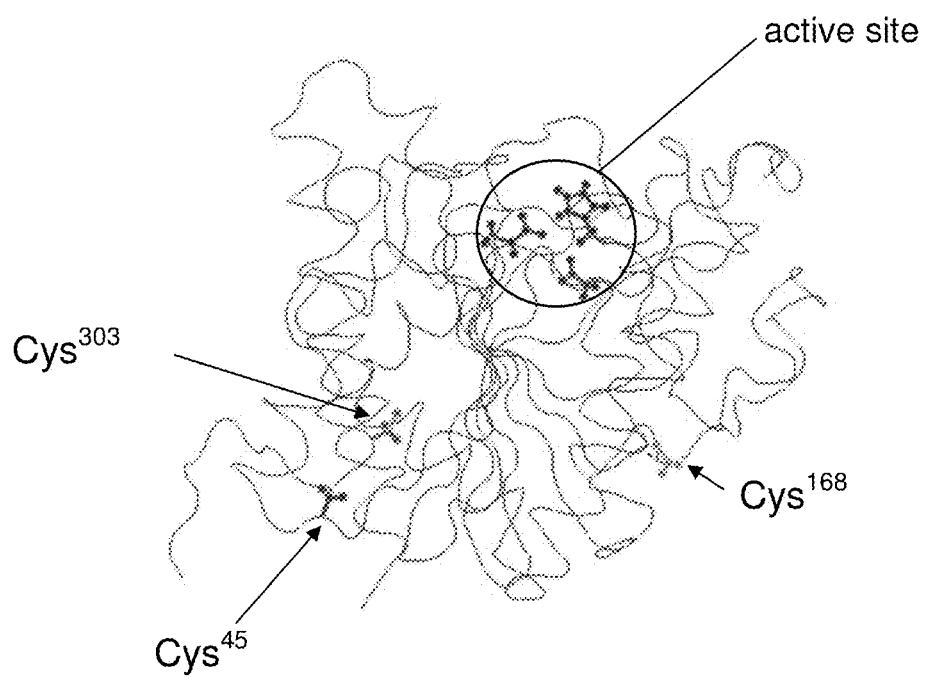
FIG. 4 shows (A) the crystal structure of the wild-type human arginase I (downloaded from NCBI website using Cn3D 4.1 software), showing that $Cys^{45}$ is far away from the active site; (B) the crystal structure of the wild-type Bacillus caldovelox arginase, showing that $Ser^{161}$ is far away from the active site.
Figure 4B:
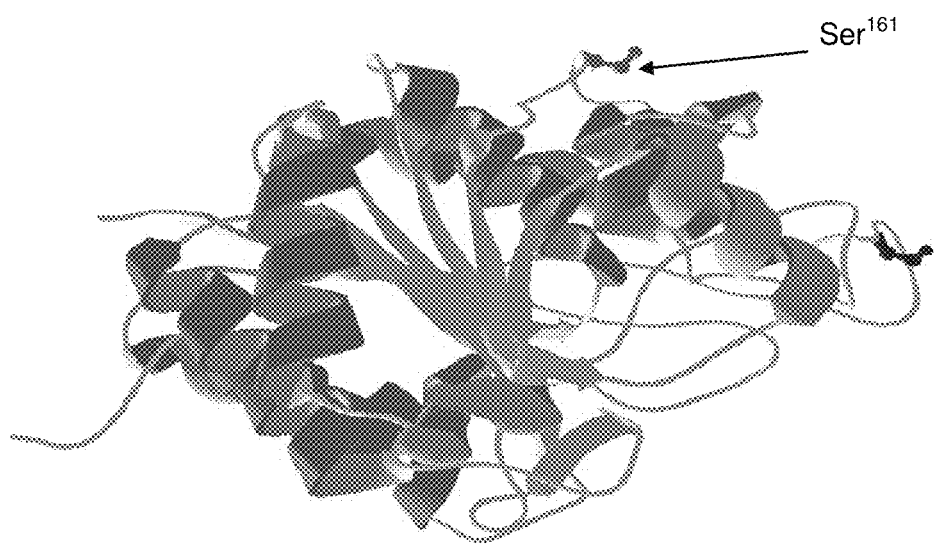

The mutated plasmid according to the above mutagenesis schemes is transformed firstly into competent *E. coli* Top 10 cells. The gene sequence of the mutated plasmid is confirmed by DNA sequencing. The gene sequence of HAI mutant designed for $Cys^{45}$ site-directed pegylation is shown in FIG. 1B (SEQ ID NO: 2). The mutated plasmid is then transformed into *E. coli* BL21-DE3 cells for protein expression. The amino acid sequence of the wild-type HAI is shown in FIG. 2A (SEQ ID NO: 5). The amino acid sequence of the C168S/C303S mutant is shown in FIG. 2B (SEQ ID NO: 6), FIG. 3A (SEQ ID NO: 10) and FIG. 3B (SEQ ID NO: 12). As shown in FIG. 2B, two cysteine residues in the wild-type human arginase I are replaced by serine residues. These two serine residues are underlined in FIG. 2B. The only cysteine residue present after the replacement is Cys45. This HAI mutant is called C168S/C303S, which only contains one single cysteine residue (also underlined in FIG. 2B). Crystal structure of the wild-type HAI is shown in FIG. 4A. Based on this structure, the rational protein drug design for constructing the C168S/C303S mutant is made. In FIG. 2D, it is shown that only one serine residue in *Bacillus caldovelox* arginase is replaced by a cysteine residue. This cysteine residue is underlined in FIG. 2D. The 6×His-tag region is also underlined and located at the C terminus. This mutant is called S161C.

Expression and Purification of 6×His-Tagged Arginases

*E. coli* BL21-DE3 harboring the plasmid containing a mutated arginase gene encoding 6×His-tagged human arginase I are grown overnight at 37° C. in LB medium containing 80 µg/mL ampicillin. The inoculum is diluted at 1:25 and grown to OD600~0.8 in a shake flask or diluted at 1:10 and grown to OD600~15 in a fermenter. The cells are then induced with 0.4 mM IPTG for 4 hours. The bacterial cells are collected by centrifugation, followed by resuspension in 50 mM Tris, 0.1 M NaCl, 10 mM $MnCl_2$, pH 7.4, and then disrupted by high pressure homogenization.

Figure 6A:
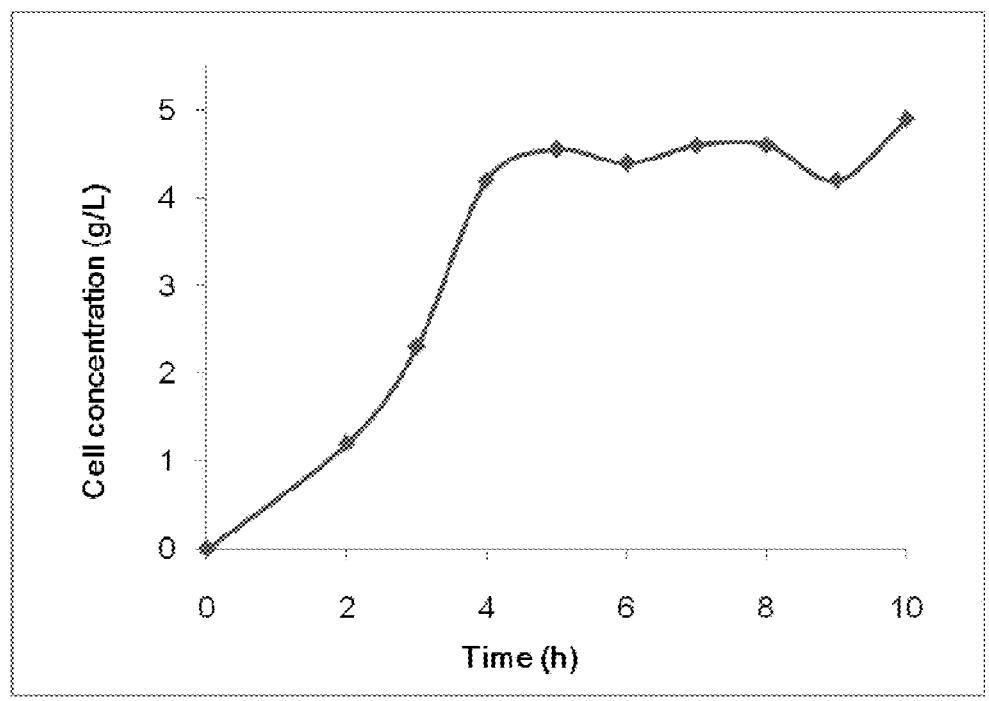
FIG. 6 depicts (A) a time-course for fermentation in a 2-liter fermenter by the E. coli BL21-DE3 containing the arginase gene, showing the results obtained from the batch fermentation and (B) the results obtained from the fed-batch fermentation; (C) the history plots of the batch fermentation and (D) the fed-batch fermentation, showing the changes of parameters such as temperature, stirring rate, pH, dissolved oxygen values; (E) the elution profile of the 6×His-tagged human arginase I mutant from a chelating FF sepharose column with the first peak being protein impurities and the second peak being the purified human arginase I; and (F) the elution profile of the 6×His-tagged *Bacillus caldovelox* arginase mutant from a chelating FF sepharose column with the first peak being the protein impurities and the second peak being the purified *Bacillus caldovelox* arginase.
Figure 6B:
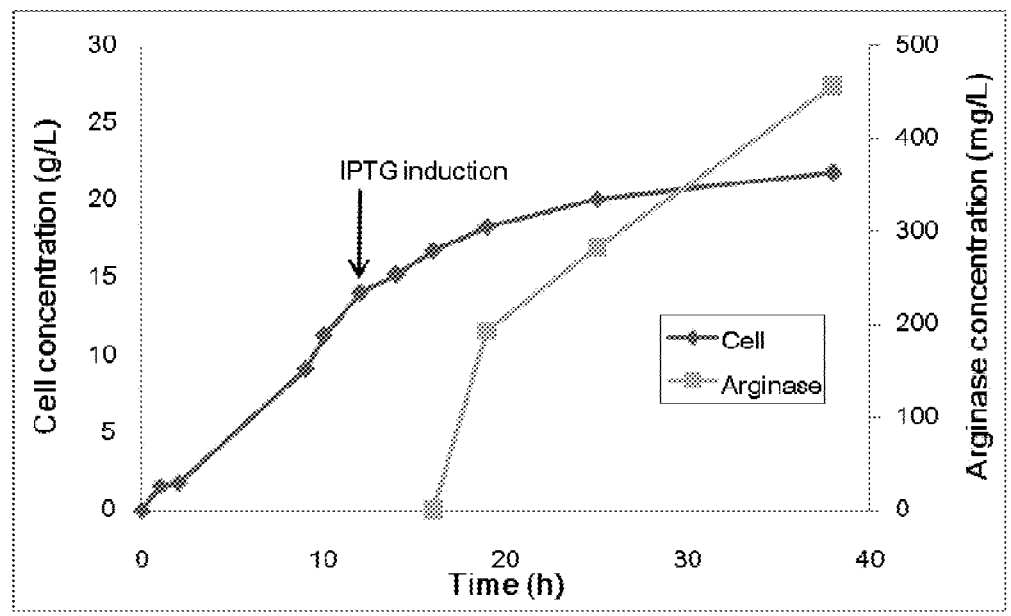
Figure 6C:
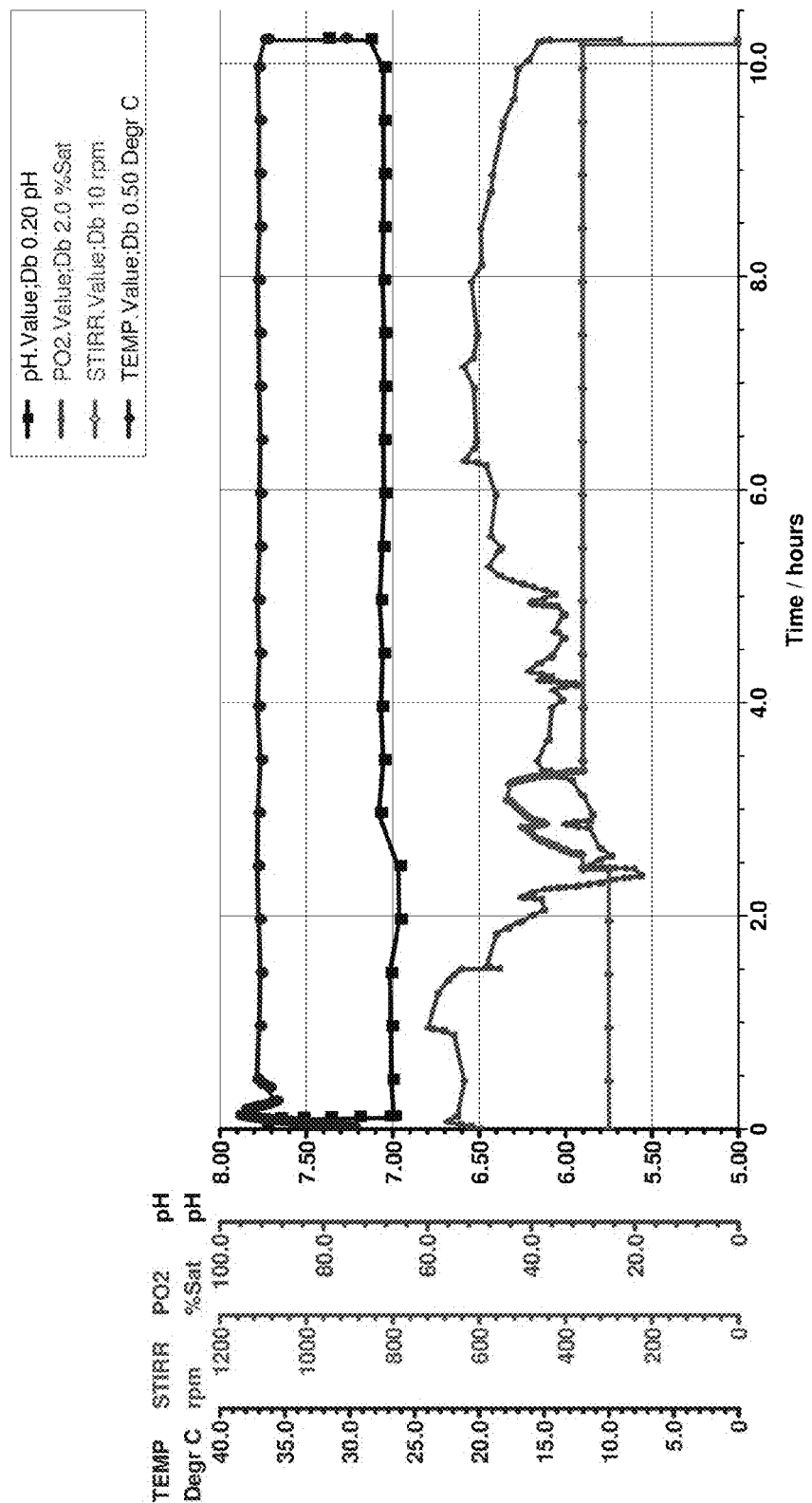
Figure 6D:
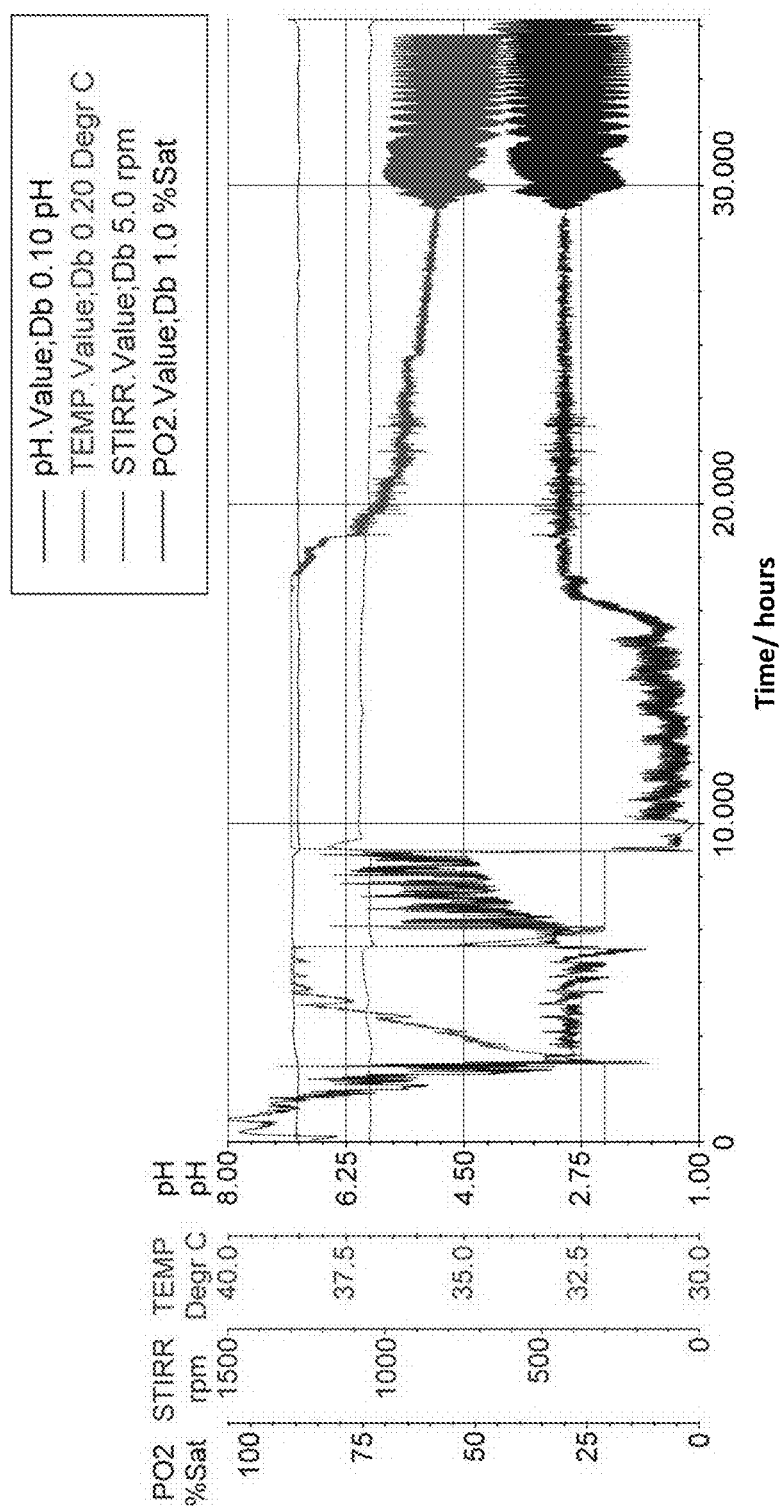
Figure 6E:
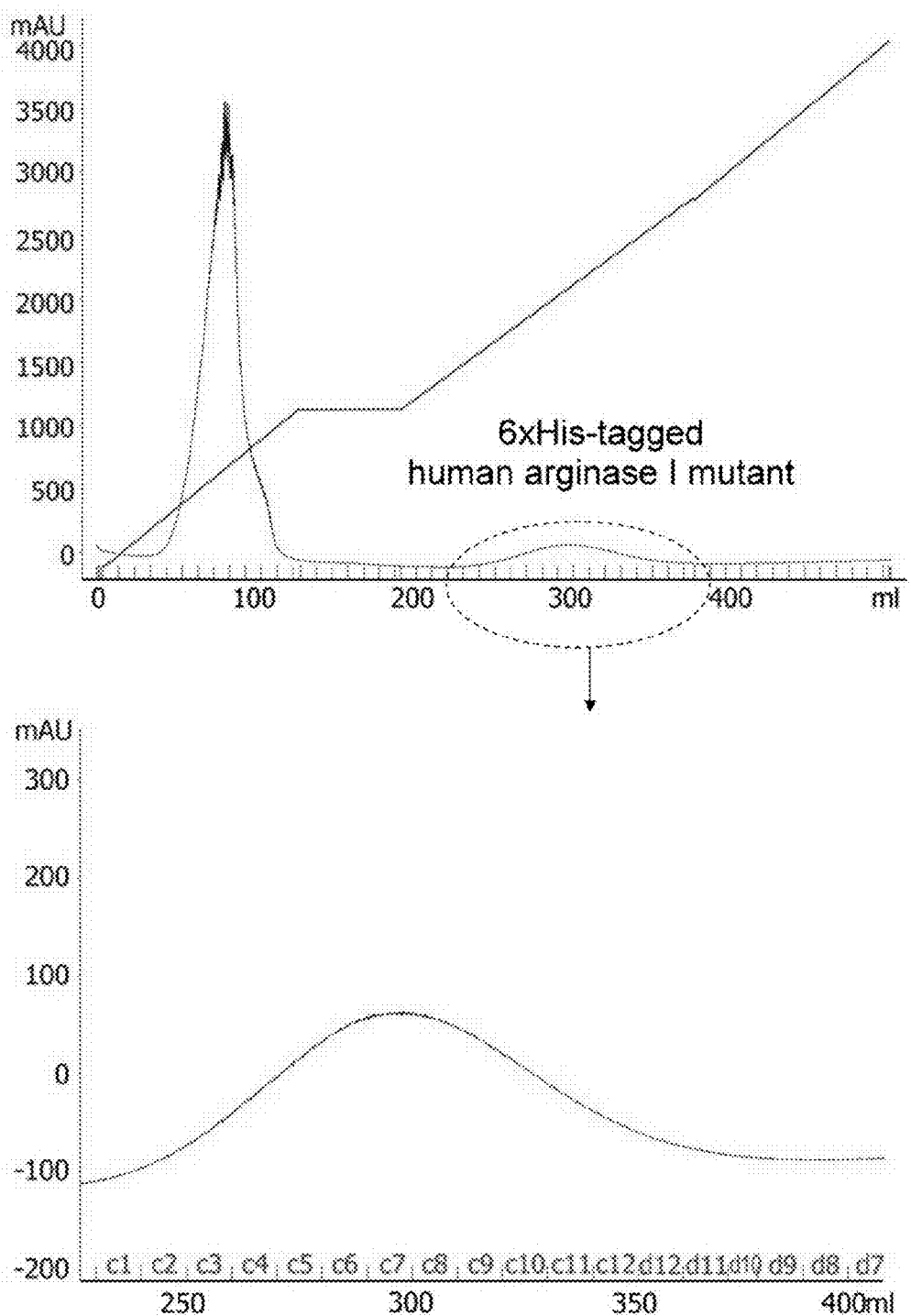
Figure 6F:
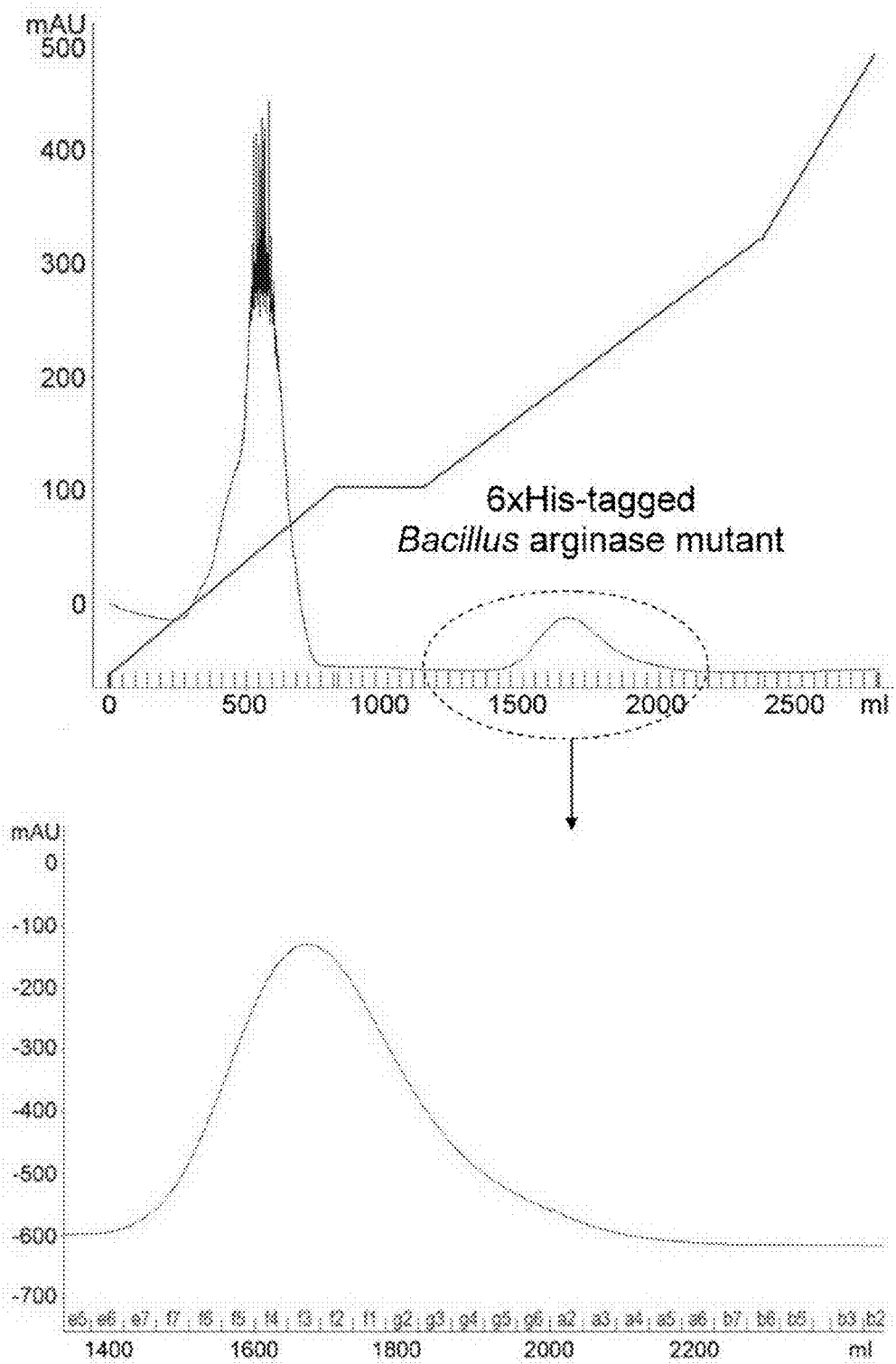
Figure 7A:
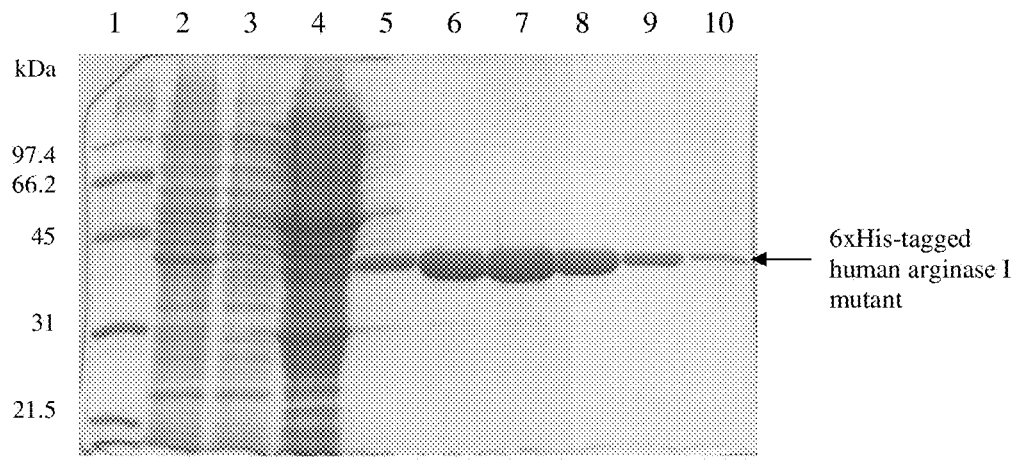
FIG. 7 shows the SDS-PAGE analysis of different fractions involving (A) 6×His-tagged human arginase I mutant and (B) 6×His-tagged *Bacillus caldovelox* arginase mutant.
Figure 7B:
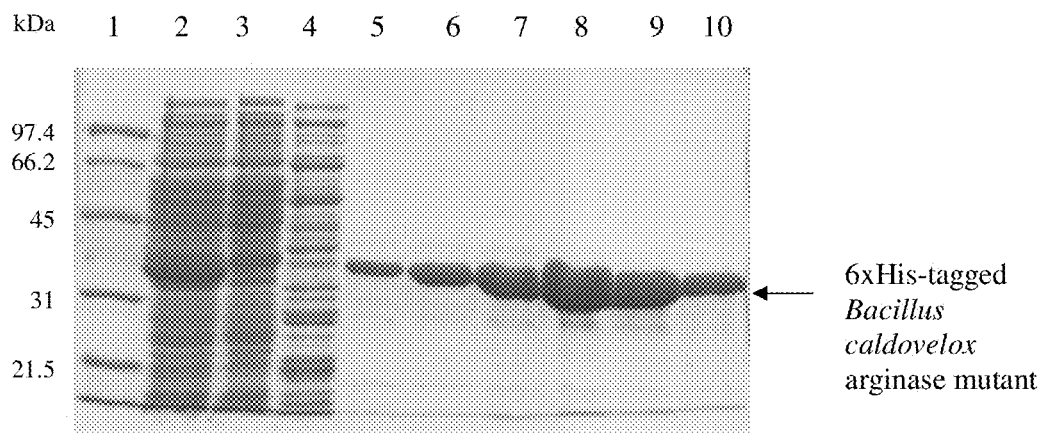

The 6×His-tagged human arginase I is purified by a chelating FF sepharose (GE Healthcare) column (5.0 cm×9 cm; bed volume of 176 mL) equilibrated with Buffer A (0.02 M sodium phosphate, 0.5 M NaCl, pH 7.4). The 6×His-tagged arginase is eluted with a gradient of 0.15 to 0.25 M imidazole (FIG. 6E & FIG. 6F). The flow rate is 20 mL/min. The fractions (FIG. 7A & FIG. 7B) containing purified arginase are collected. The yields of purified arginase are about 280 mg/L cell cultures.

The same procedure as described above for 6×His-tagged human arginase I is also used to obtain purified 6×His-tagged *Bacillus caldovelox* arginase in the present invention.

Site-Directed Pegylation of 6×His-Tagged Arginases

Figure 5A:
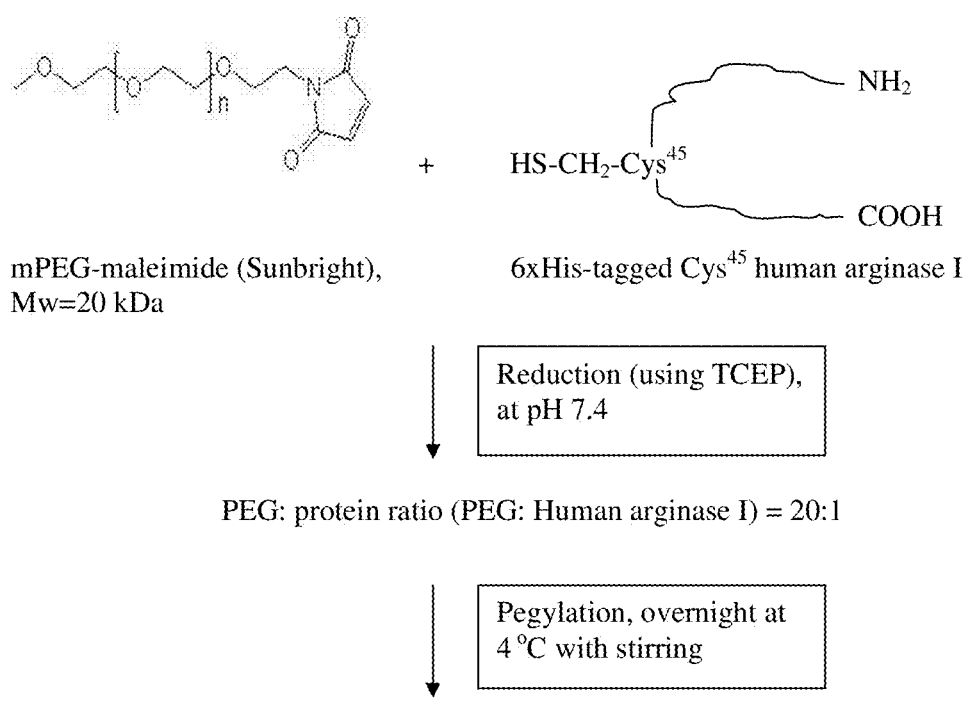
FIG. 5 shows (A) the conjugation procedures for $Cys^{45}$-specific mono-pegylation of the 6×His-tagged human arginase I mutant with a single chain mPEG-maleimide (20 kDa), showing that the double bond of a maleimide undergoes an alkylation reaction with a sulfhydryl group to form a stable thioether bond; and (B) the corresponding procedures for $Cys^{161}$-specific mono-pegylation of the 6×His-tagged Bacillus caldovelox arginase mutant.
Figure 5B:
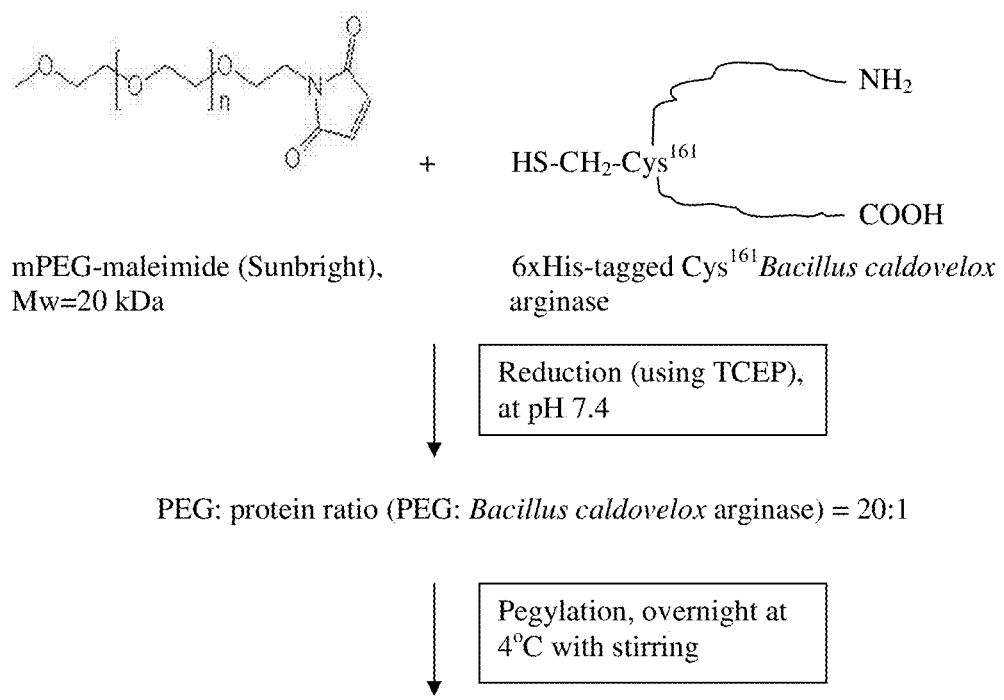

FIG. 5A shows the procedures for conjugating $Cys^{45}$-specific mono-pegylation of the 6×His-tagged human arginase I mutant with a single chain mPEG-maleimide (20 kDa), referred to as "HAI-PEG20". The double bond of a maleimide undergoes an alkylation reaction with a sulfhydryl group to form a stable thioether bond. FIG. 5B shows the conjugation procedures for $Cys^{161}$-specific mono-pegylation of the 6×His-tagged *Bacillus caldovelox* arginase mutant with a single chain mPEG-maleimide (20 kDa), referred to as "BCA-PEG20". One gram of 6×His-tagged arginase is diafiltered into 0.02 M sodium phosphate, 0.5 M NaCl, pH 7.4, using Millipore Tangential Flow Filtration system (500 mL) with 10 K (cut-off) membrane (Millipore). The concentration of arginase is finally diluted to about 2 mg/mL. The reducing agent Tris(2-carboxyethyl)phosphine, TCEP, is added in a molar excess of 10 moles to one mole of arginase for reduction and the solution is gently stirred for 4 hours at room temperature. mPEG-Maleimide or mPEG-MAL (20 kDa) (Sunbright) in a molar excess of 20 moles to one mole of arginase is added to the reduced arginase and stirred for overnight at 4° C.

Figure 8A:
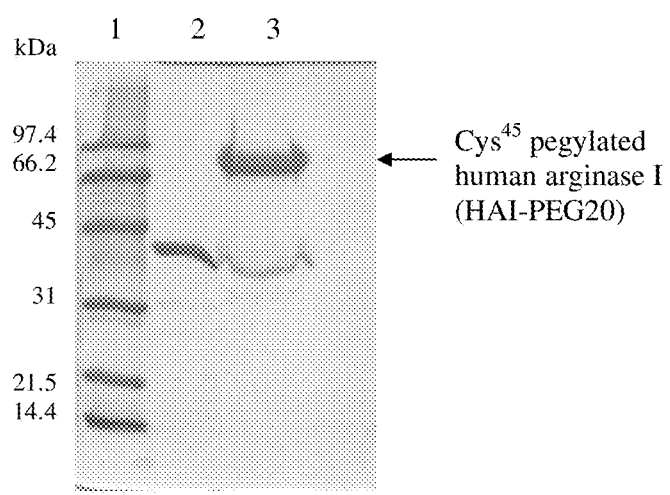
FIG. 8 shows (A) the SDS-PAGE analysis of the unpegylated human arginase I mutant and the $Cys^{45}$ pegylated human arginase I mutant (Lane 1: protein molecular weight marker; Lane 2: unpegylated human arginase I mutant; and Lane 3: $Cys^{45}$ pegylated human arginase I (HAI-PEG20)); (B) the SDS-PAGE analysis of unpegylated *Bacillus caldovelox* arginase mutant and the $Cys^{161}$ pegylated *Bacillus caldovelox* arginase (Lane 1: protein molecular weight marker; Lane 2: the unpegylated *Bacillus caldovelox* arginase mutant; and Lane 3: $Cys^{161}$ pegylated *Bacillus caldovelox* arginase (BCA-PEG20)).
Figure 8B:
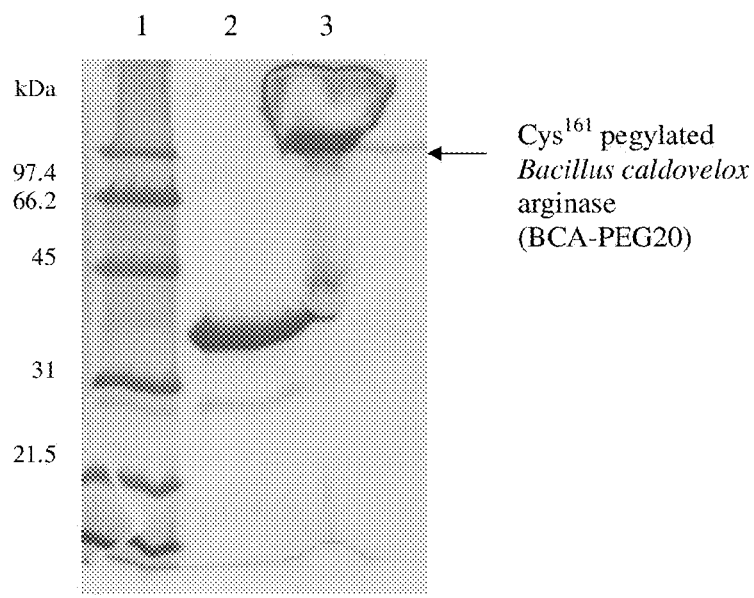

The progress of site-directed pegylation is monitored by SDS-PAGE (FIGS. 8A & 8B). Under the above described conditions, the free sulfhydryl group of cysteine at position 45 on human arginase I is specifically linked via a stable thioether bond to the activated maleimide group of mPEG-MAL (20 kDa). The final product of conjugation comprises predominantly $Cys^{45}$ pegylated human arginase I, unconjugated human arginase I, and mPEG-MAL (20 kDa). Similarly for *Bacillus caldovelox* arginase, the cysteine residue at position 161 is specifically linked via a stable thioether bond to the activated maleimide group of mPEG-MAL (20 kDa).

The mPEG-MAL (20 kDa) pegylated arginase is advantageous over the mPEG-MAL (5 kDa) pegylated arginase in terms of a longer half-time, and advantageous over the mPEG-MAL (40 kDa) pegylated arginase in terms of a better solubility.

Batch Fermentation in a 2-Liter Fermenter

The *E. coli* BL21-DE3 strain containing the arginase gene is stored at −80° C. To prepare the seed inoculum for batch and fed-batch fermentation, 100 µL frozen stock of the aforementioned strain are transferred into 250 mL flask containing 80 mL of fermentation medium. The bacterial culture is cultivated at 37° C. and pH 7.0 in an orbital shaker rotating at 250 rpm. The cultivation is terminated when OD600 nm reaches 5.5-6.0 at about 8-10 hours. The 12 mL (1%) seed inoculum is introduced into the 2-L fermenter containing 1,200 mL autoclaved enriched fermentation medium. The batch fermentation is carried out at a temperature of 37° C. The pH is maintained at 7.0 by adding sodium hydroxide and hydrochloric acid. The dissolved oxygen level is controlled at above 30% air saturation by introducing air at 1-4 L/min and adjusting the stirring rate of the fermenter at 300-1,200 rpm. Isopropyl-beta-D-thiogalacto-P (IPTG) 100 mM, inducer of the protein expression of *Bacillus caldovelox* arginase (BCA), is introduced into the fermentation broth to a final concentration of 0.5 mM when the OD600 nm is about 11.0 at 5 hours. After the IPTG induction, the fermentation continues until about 9 hours when the OD600 nm is about 16.4. The fermentation cells are harvested for separation and purification of BCA at about 4 hours after IPTG induction. The aforementioned strain produces active BCA in an amount of about 105 mg/L of the fermentation medium. The time-course of the fermentation is plotted in FIG. 6A. The history plot of this batch fermentation showing the changes of parameters such as temperature, stirring rate, pH and dissolved oxygen values is depicted in FIG. 6C.

Fed-Batch Fermentation in a 2-L Fermenter

The Fed-batch fermentation with high cell density culture is carried out at 37° C., pH 7.0 and dissolved oxygen is kept above 30% air saturation during the whole fermentation process. The procedure for preparing the seed inoculum is similar to that of the batch fermentation described above. The fermentation is initially started with batch cultivation strategy by introducing 5 mL (1%) seed inoculum into the 2-L fermenter containing 500 mL autoclaved enriched fermentation medium. The dissolved oxygen decreases gradually to around 30% air saturation during the growth phase in batch cultivation period. Once the dissolved oxygen level increases to above 80%, representing the depletion of carbon source, the $PO_2$ stat fed-batch strategy is started with the addition of feeding the enriched medium. In this strategy, the feeding rate is adjusted to maintain the dissolved oxygen level of below 60%, which provides minimal but adequate amount of carbon source during fermentation process. Isopropyl-beta-D-thiogalacto-P (IPTG) 100 mM is introduced into the fermentation broth to a final concentration of 0.5 mM when the OD600 nm is about 100 at 18 hours. After the IPTG induction, the fermentation continues until about 28 hours when the OD600 nm is about 186.8. The fermentation cells are harvested for separation and purification of BCA at about 10 hours after IPTG induction. The aforementioned strain produces active BCA in an amount of about 1,489.6 mg/L of the fermentation medium, which is higher than all the other reported yields of different types of arginase. The time-course of the fermentation is plotted in FIG. 6B. The history plot of this fed-batch fermentation showing the changes of parameters such as temperature, stirring rate, pH and dissolved oxygen values is depicted in FIG. 6D.

Comparison of Batch and Fed-Batch Fermentation

Table 1 below compares the results of batch and fed-batch fermentation. The comparison demonstrates that the fed-batch fermentation is much superior to the batch operation in terms of culture OD600, cell dry weight and yield of arginase per liter culture.

TABLE 1

|  | Batch fermentation | Fed-batch fermentation |
|---|---|---|
| Maximum $OD_{600}$ reached | 16.4 | 186.8 |
| Cell dry weight (g) | 4.9 | 76.6 |
| yield of BCA (mg/L) | 105.0 | 1489.6 |
| yield of BCA (mg/g-cell) | 21.4 | 19.4 |

Purification of Site-Directed Pegylated Arginases

Affinity nickel ion column chromatography is used to separate 6×His-tagged site-directed pegylated arginases from mPEG-MAL (20 kDa) as described as follows. The final products of conjugation are loaded onto a chelating FF sepharose (GE Healthcare) column (5.0 cm×9 cm; bed volume of 176 mL) equilibrated with Buffer A (0.02 M sodium phosphate, 0.5 M NaCl, pH 7.4). The column is washed with 5 column volumes of Buffer A to remove free mPEG-MAL (20 kDa). The pegylated arginase is eluted using a salt gradient from 30% to 100% of Buffer B (0.02 M sodium phosphate, 0.5 M NaCl, 0.5 M imidazole, pH 7.4) for 5 column volumes. The protein content of the eluent is monitored at 280 nm wavelength. The column is eluted at a flow rate of 20 mL/min and the pegylated arginase fractions are collected. The pooled fractions are diafiltered into PBS buffer (Gibco) and concentrated to 4-6 mg/mL. Before animal study, the endotoxin in the protein drug is removed using a Q-filter (Sartoris).

Site-specific Pegylation at Position Equivalent to Cys-45 of Human Arginase (HAI)

As seen in FIG. 19A, *Capra hircus* arginase I (SEQ ID NO: 23), *Heterocephalus glaber* arginase I (SEQ ID NO: 24), *Bos taurus* arginase I (SEQ ID NO: 25), *Sus scrofa* arginase I (SEQ ID NO: 26), *Plecoglossus altivelis* arginase I (SEQ ID NO: 27), *Salmo salar* arginase I (SEQ ID NO: 28), *Oncorhynchus mykiss* arginase I (SEQ ID NO: 29), *Osmerus mordax* arginase I (SEQ ID NO: 30), *Hyriopsis cumingii* arginase I (SEQ ID NO: 31), *Rattus norvegicus* arginase II (SEQ ID NO: 32), *Mus musculus* arginase II (SEQ ID NO: 33), human arginase II (SEQ ID NO: 34), *Bos taurus* arginase II (SEQ ID NO: 35), *Heterocephalus glaber* arginase II (SEQ ID NO: 36), *Pan troglodytes* arginase II (SEQ ID NO: 37), *Oryctolagus cuniculus* arginase II (SEQ ID NO: 38), *Delftia* arginase (SEQ ID NO: 39), *Bacillus coagulans* arginase (SEQ ID NO: 40), *Hoeflea phototrophica* arginase (SEQ ID NO: 41) and *Roseiflexus castenholzii* arginase (SEQ ID NO: 42) possess an equivalent of Cys-45, analogous to the human arginase described above. Using procedures similar to those described above, cysteine residue at position equivalent to Cys-45 can be used and site-specific pegylation can be performed on that site.

Site-specific Pegylation at Position Equivalent to Ser-161 of *Bacillus caldovelox* Arginase (BCA)

Further, as seen in FIG. 19B, the serine residue of arginases of *Bacillus methanolicus* (SEQ ID NO: 43), *Bacillus* sp. NRRL B-14911 (SEQ ID NO: 44), *Planococcus donghaensis* (SEQ ID NO: 45), *Paenibacillus dendritiformis* (SEQ ID NO: 46), *Desmospora* sp. (SEQ ID NO: 47), *Methylobacter tundripaludum* ((SEQ ID NO: 48), *Stenotrophomonas* sp. (SEQ ID NO: 49), *Microbacterium laevamformans* (SEQ ID NO: 50), *Porphyromonas uenonis* (SEQ ID NO: 51), *Agrobacterium* sp. (SEQ ID NO: 52), *Octadecabacter arcticus* (SEQ ID NO: 53), *Agrobacterium tumefaciens* (SEQ ID NO: 54), *Anoxybacillus flavithermus* (SEQ ID NO: 55), *Bacillus pumilus* (SEQ ID NO: 56), *Geobacillus thermoglucosidasius* (SEQ ID NO: 57), *Geobacillus thermoglucosidans* (SEQ ID NO: 58), *Brevibacillus laterosporus* (SEQ ID NO: 59), *Desulfotomaculum ruminis* (SEQ ID NO: 60), *Geobacillus kaustophilus* (SEQ ID NO: 61), *Geobacillus thermoleovorans* (SEQ ID NO: 62), *Geobacillus thermodenitrificans* (SEQ ID NO: 63), *Staphylococcus aureus* (SEQ ID NO: 64), Halophilic archaeon DL31 (SEQ ID NO: 65), *Halopiger xanaduensis* (SEQ ID NO: 66) and *Natrialba magadii* (SEQ ID NO: 67), analogous to Ser-161 of BCA, can be engineered to be a cysteine residue. As set forth above, this creates a site-specific pegylation location in these arginases that can be fabricated according to the above techniques.

Additional Pegylation Sites in Human and *Bacillus caldovelox* Arginases

Additional sites have been identified for site-specific pegylation of human and *B. caldovelox* arginase that do not interfere with the active site of the respective arginases. As seen in FIG. 20, in human arginase, position 168 is substantially equivalent to Ser-161 of *B. caldovelox* arginase. Further, as seen in FIG. 21, in *B. caldovelox* arginase, position 41 can be used for site-specific pegylation (equivalent site of Cys-45 of human arginase I). Though the two enzymes do not share exactly the same amino acid at the position, given the resembling features of the amino acid side chain (human Cys-168 and *B. caldovelox* Ser-161 are both polar side chains, and human Cys-45 and *B. caldovelox* Tyr-41 both have bulky side chains), and the highly similar 3-dimensional structures of the 2 arginases, the results in one enzyme can be extended to the other.

Site-specific Single Pegylation for Human and *Bacillus caldovelox* Arginases at Additional Site Based on the highly similar 3-dimensional structures of BCA and HAI it can be inferred reasonably that the results in BCA can be extrapolated to HAI, indicating that Cys-168 would be a favourable site for PEG attachment far away from the enzyme active site. In this case, Cys-45 and Cys-303 would be substituted with serine to ensure specific attachment of PEG at Cys-168. Conversely, Tyr-41 of BCA can be engineered to a cysteine for site-specific PEG attachment.

Site-Specific Pegylation at Two Sites in Human and *Bacillus caldovelox* Arginases Further to the discussion above, the present invention can also perform site-specific pegylation at two sites on human arginase and at two sites on *B. caldovelox* arginase. That is, the human arginase can be pegylated at position 45 and position 168 while *B. caldovelox* arginase can be pegylated at sites 41 and 161.

Site-specific Pegylation at Two Sites Equivalent to Cys-45 and Cys-168 of Human Argianse As shown in FIG. 19C, arginases from organisms (*Capra hircus* arginase I, *Heterocephalus glaber* arginase I, *Bos taurus* arginase I, *Sus scrofa* arginase I, *Plecoglossus altivelis* arginase I, *Salmo salar* arginase I, *Oncorhynchus mykiss* arginase I, *Osmerus mordax* arginase I, *Hyriopsis cumingii* arginase I, *Rattus norvegicus* arginase II, *Mus musculus* arginase II, human arginase II, *Bos taurus* arginase II, *Heterocephalus glaber* arginase II, *Pan troglodytes* arginase II, *Oryctolagus cuniculus* arginase II) possess two cysteine residues equivalent to Cys-45 and Cys-168 of HAI, which can be used for site-specific pegylation at two sites. Other redundant cysteines in these proteins (e.g. Cys-303 of HAI) will be specifically engineered as serine instead.

Site-Specific Pegylation at Two Sites Equivalent to Tyr-41 and Ser-161 of *Bacillus caldovelox* Arginase As shown in FIG. 19D, arginases of organisms (*Bacillus methanolicus, Desmospora* sp., *Geobacillus thermoglucosidasius, Geobacillus thermoglucosidans, Brevibacillus laterosporus, Geobacillus kaustophilus, Geobacillus thermoleovorans, Geobacillus thermodenitrificans*) possess Tyrosine and Serine equivalent to Tyr-41 and Ser-161 of BCA, which can both be engineered into cysteines for site-specific pegylation at two sites.

Pegylation at Lysine Residues in *Bacillus caldovelox* Arginase

As seen in FIG. 22, various lysine residues (14 shown in FIG. 22) present in *B. caldovelox* arginase are spaced at positions away from the active site and can serve as site-specific pegylation locations.

In Vitro Cytotoxicity of Site-Directed Pegylated Arginases

In vitro cytotoxicity of $Cys^{45}$ pegylated human arginase I and $Cys^{161}$ pegylated *Bacillus caldovelox* arginase are studied by standard MTT assay in different human cancer cells (melanoma, hepatocellular carcinoma, gastric adenocarcinoma, colorectal adenocarcinoma, pancreatic carcinoma, pancreatic adenocarcinoma, and T cell leukaemia)

The known numbers of cells (5000) are incubated for 68 hours in each well of 96-well plate in a 5% $CO_2$ incubator at 37° C. in the presence of different concentrations of $Cys^{45}$ pegylated human arginase I and $Cys^{161}$ pegylated *Bacillus caldovelox* arginase. After 68 hours of drug incubation, 50 µg of the MTT (3-(4, 5-Dimethylthiazol-2-yl)-2,5-diphenyltetrazolium bromide, a tetrazole) solution is added in each well and incubated for another 4 hours. The supernatant is discarded and 100 µL of 10% SDS/0.01 M HCl is added in each well and then incubated overnight. The absorbance is recorded at 540 nm by a microplate reader (Bio-Rad). The concentration of each drug required to inhibit the 50% cell growth ($IC_{50}$) is determined for different cancer cell lines. Experiment is performed in triplicate.

The $IC_{50}$ values of $Cys^{45}$ pegylated human arginase I (HAI-PEG20) and $Cys^{161}$ pegylated *Bacillus caldovelox* arginase (BCA-PEG20) for different cell lines are calculated and the results are listed in Table 2. As *Bacillus caldovelox* arginase is never known for anti-cancer response, it is thus the first time to have demonstrated its anti-cancer properties and efficacies. In various melanoma cell lines (SK-MEL-2, SK-MEL-28, A375), the $IC_{50}$ values of $Cys^{45}$ pegylated human arginase I are lower when compared to those of $Cys^{161}$ pegylated *Bacillus caldovelox* arginase. Among different hepatocellular carcinoma cell lines (HepG2, Hep3B, PLC/PRF/5), HepG2 cells are the most sensitive to both $Cys^{45}$ pegylated human arginase I and $Cys^{161}$ pegylated *Bacillus caldovelox* arginase. Taken together, all liver cancer (HCC) and melanoma cell lines tested are inhibited efficiently by BCA-PEG20 and HAI-PEG20.

$Cys^{161}$ pegylated *Bacillus caldovelox* arginase is also tested for the other five cancer cell lines including gastric adenocarcinoma, colorectal adenocarcinoma, pancreatic carcinoma, pancreatic adenocarcinoma, and T cell leukaemia. For gastric adenocarcinoma cell lines, the $IC_{50}$ of $Cys^{161}$ pegylated *Bacillus caldovelox* arginase for MKN-45 cells (0.798 U/mL) is similar to that for AGS cells (0.662 U/mL). Among different colorectal adenocarcinoma cell lines (WiDr, HT-29, SW1116), WiDr cells and HT-29 cells are more sensitive to $Cys^{161}$ pegylated *Bacillus caldovelox* arginase. When comparing the pancreatic carcinoma cell line (PANC-1) and the pancreatic adenocarcinoma cell line (BxPC-3), the $IC_{50}$ of $Cys^{161}$ pegylated *Bacillus caldovelox* arginase is lower in PANC-1 cells by four-fold. For T cell leukaemia cell line (Jurkat, Clone E6-1), the $IC_{50}$ of $Cys^{161}$ pegylated *Bacillus caldovelox* arginase (0.41 U/mL) is also relatively low when compared to the other cancer cell lines. Taken together, all cancer cell lines tested are sensitive to (and inhibited by) HAI-PEG20 and BCA-PEG20 treatments.

TABLE 2

|  |  | In vitro $IC_{50}$ | | | |
|---|---|---|---|---|---|
|  |  | $Cys^{45}$ pegylated human arginase I | | $Cys^{161}$ pegylated *Bacillus caldovelox* arginase | |
| Tumor | Cell line | U/mL | µg/mL | U/mL | µg/mL |
| Melanoma | SK-MEL-2 | 0.079 | 0.80 | 0.612 | 11.25 |
|  | SK-MEL-28 | 0.064 | 0.65 | 0.910 | 16.72 |
|  | A375 | 0.088 | 0.90 | 0.15 | 2.76 |
| Hepatocellular carcinoma | HepG2 | 0.097 | 0.99 | 2.002 | 36.79 |
|  | Hep3B | 0.290 | 2.95 | 9.1 | 57.68 |
|  | PLC/PRF/5 | 0.94 | 9.56 | 2.376 | 43.67 |
| Gastric adenocarcinoma | MKN-45 | — |  | 0.798 | 14.67 |
|  | AGS | — |  | 0.662 | 12.17 |
| Colorectal adenocarcinoma | WiDr | 0.075 | 0.76 | 0.192 | 3.53 |
|  | HT-29 | — |  | 0.220 | 4.04 |
|  | SW1116 | 0.41 | 4.18 | 1.515 | 27.84 |
| Pancreatic carcinoma | PANC-1 | — |  | 0.263 | 4.84 |
| Pancreatic adenocarcinoma | BxPC-3 | — |  | 0.846 | 15.54 |
| T cell leukemia | Jurkat, Clone E6-1 | — |  | 0.410 | 7.54 |

Depletion of Arginine by Site-Directed Pegylated Arginases

Pharmacodynamics of $Cys^{45}$ pegylated human arginase I and $Cys^{161}$ pegylated *Bacillus caldovelox* arginase are studied using BALB/c normal mice. The study is carried out in conjunction with the pharmacokinetic study (described below). Therefore, the protocol remained the same. Again, the blood samples collected are centrifuged immediately at 13,200 rpm for 5 minutes and the plasma layer are collected for further analysis using the Amino Acid Analyzer (Biochrom 30, Biochrom Ltd., England). For pharmacokinetic study, plasma samples are first purified from urea using molecular sieve centrifugal filter units as sample preparation columns before subjecting to enzymatic activity determinations.

Figure 10A:
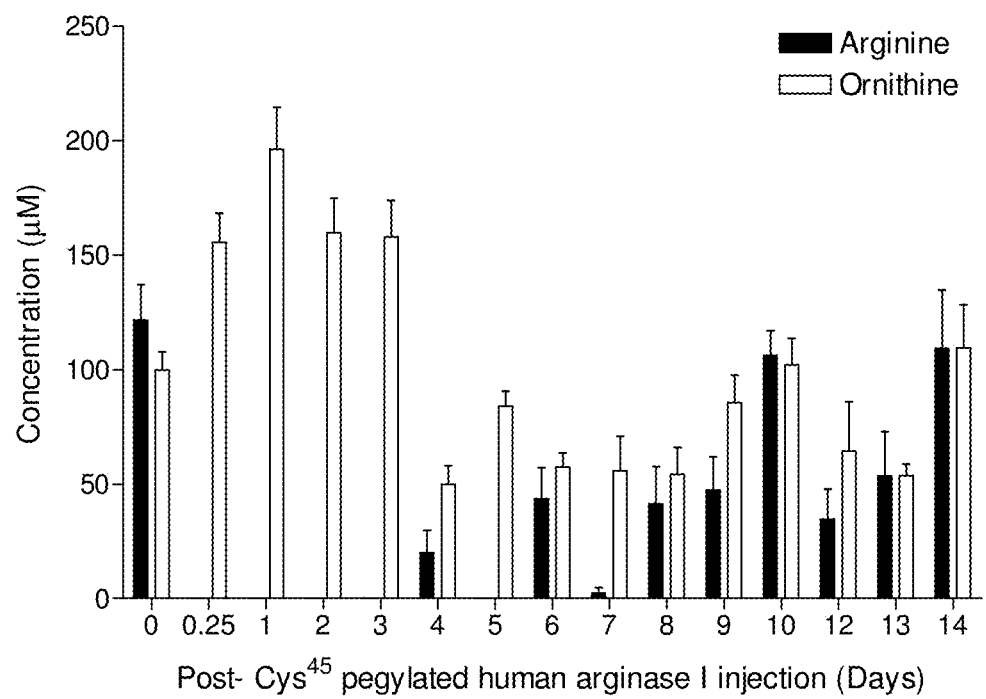
FIG. 10 shows (A) the pharmacodynamic profile of a single dose of $Cys^{45}$ pegylated human arginase I (HAI-PEG20) injected intraperitoneally in BALB/c mice up to Day 14; and (B) the pharmacodynamic profile of a single dose of $Cys^{161}$ pegylated *Bacillus caldovelox* arginase (BCA-PEG20) injected intraperitoneally in BALB/c mice up to Day 14.

As shown in FIG. 10A, ornithine level starts to increase after the injection of $Cys^{45}$ pegylated human arginase I (HAI-PEG20) and stays at a high level (>150 µM) up to Day 3. Arginine is totally depleted starting from 6 hour (Day 0) and starts to appear 6.8±2.3 days after arginase administration. This indicates that HAI-PEG20 depletes blood arginine efficiently.

Figure 10B:
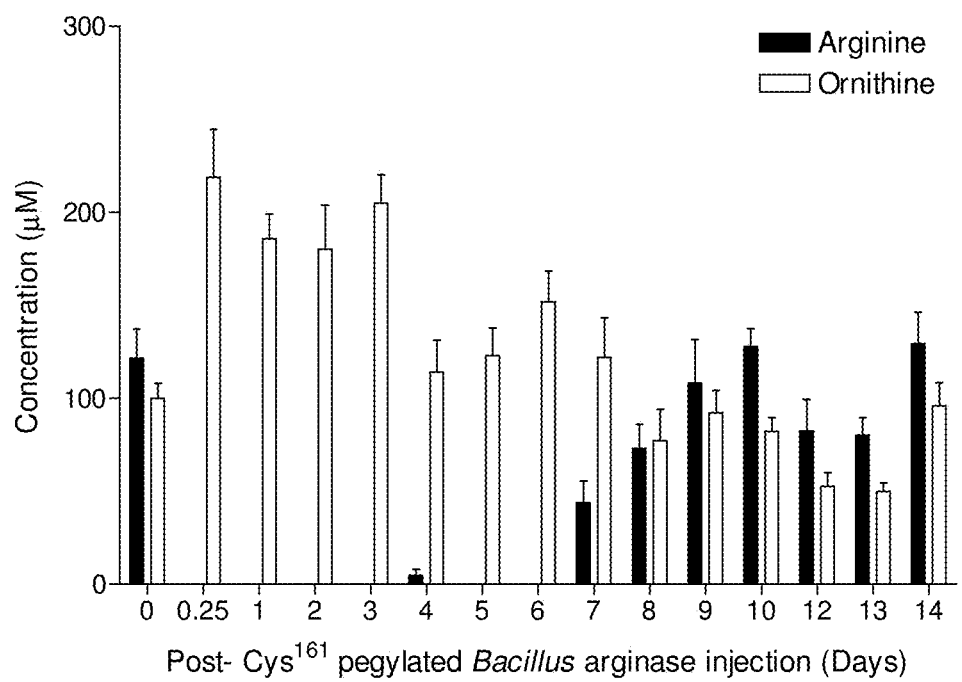

For $Cys^{161}$ pegylated *Bacillus caldovelox* arginase (BCA-PEG20), ornithine level also starts to increase and stays at a high level (>170 µM) up to Day 3 (FIG. 10B). Arginine is totally depleted starting from 6 hour (Day 0) and starts to appear 6.7±2.1 days after arginase administration. This indicates that BCA-PEG20 depletes blood arginine efficiently. Both pegylated arginases ($Cys^{45}$ pegylated human arginase I and $Cys^{161}$ pegylated *Bacillus caldovelox* arginase) display a similar pharmacodynamic profile.

Figure 9A:
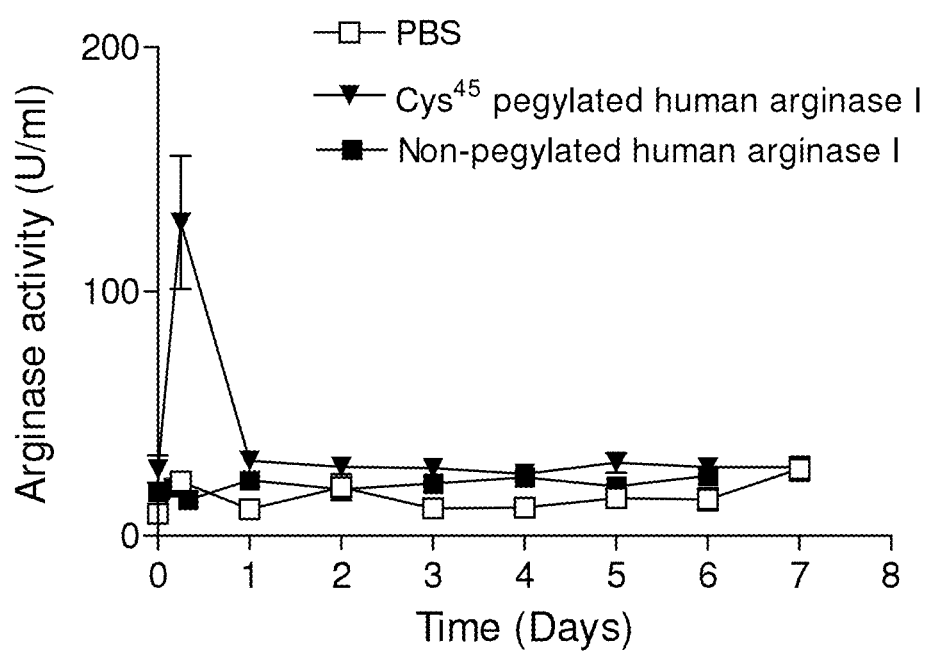
FIG. 9 shows (A) the pharmacokinetic profiles of a single dose of non-pegylated and $Cys^{45}$ pegylated human arginase I (HAI-PEG20) injected intraperitoneally in BALB/c mice; and (B) the pharmacokinetic profiles of a single dose of non-pegylated and $Cys^{161}$ pegylated *Bacillus caldovelox* arginase (BCA-PEG20) injected intraperitoneally in BALB/c mice.
Figure 9B:
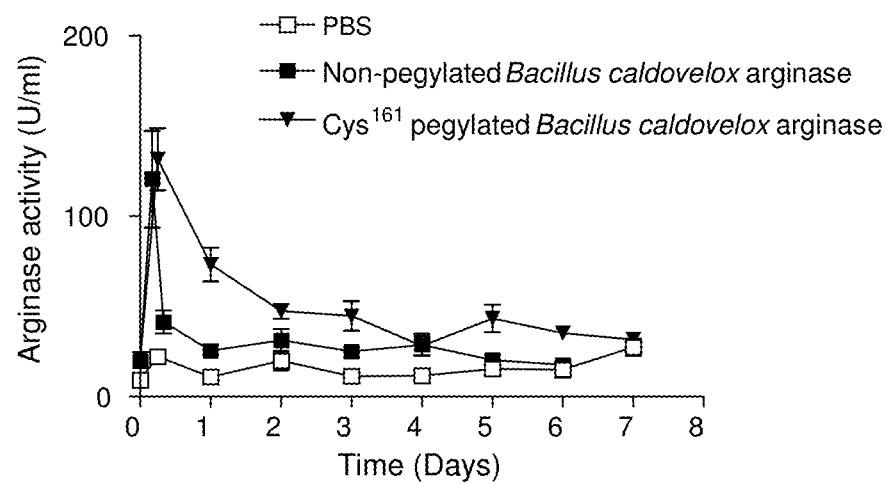

As shown in FIG. 9A, the enzymatic activity of $Cys^{45}$ pegylated human arginase I increases sharply 6 hours after drug administration representing a very fast drug absorption and provides significantly higher drug exposure to the animal as presents by an increase in area under curve for over 3.8 folds in comparison to the unpegylated human arginase I. For $Cys^{161}$ pegylated *Bacillus caldovelox* arginase, plasma drug arginase activity increases sharply 6 hours after drug administration representing a very fast drug absorption follows by a slow drug elimination with a terminal half-life of 83.7±24.4 hours (FIG. 9B). In comparison to unpegylated *Bacillus cal-*

*dovelox* arginase that has a drug elimination half-life of about 7.3±2.3 hours, $Cys^{161}$ pegylated *Bacillus caldovelox* arginase has shown excellent improvement in extension of drug elimination half-life for over 11 folds.

In Vivo Anti-Tumor Efficacy on Liver Cancer

In vivo anti-tumor efficacy of non-pegylated human arginase I (HAI) and $Cys^{45}$ pegylated human arginase I (HAI-PEG20) on liver cancer are studied and compared.

A number of BALB/c nude mice are injected with hepatocellular carcinoma Hep3B cells intraperitoneally (i.p.) and maintained in vivo. Then each of the 30 BALB/c nude mice is injected with about $1\times10^6$ of the in vivo maintained cancer cells to the right axilla subcutaneously. When palpable tumors of about 5 mm in diameter are found, the mice are separated into three different groups (see Table 3). Drugs or PBS buffer are administered intraperitoneally weekly for 8 weeks. Body weights and tumor dimensions (L: length of the longer diameter and W: length of the shorter diameter of the tumor) are measured twice a week. Tumor volume ($\frac{1}{2}\times L\times W^2$) is calculated and plotted against the time of incubation. After 60 days or when tumor diameter reaches about 2.5 cm, the mice are euthanized. Survival rates of the mice are recorded at the end of the study.

TABLE 3

In vivo anti-tumor activity protocol

| Group | Testing drug | Mice | Units/mouse | Route |
|---|---|---|---|---|
| 1 | PBS | 5M5F | n/a | i.p. |
| 2 | Non-pegylated human arginase I | 5M5F | 500 | i.p. |
| 3 | $Cys^{45}$ pegylated human arginase I | 5M5F | 500 | i.p. |

Figure 11A:
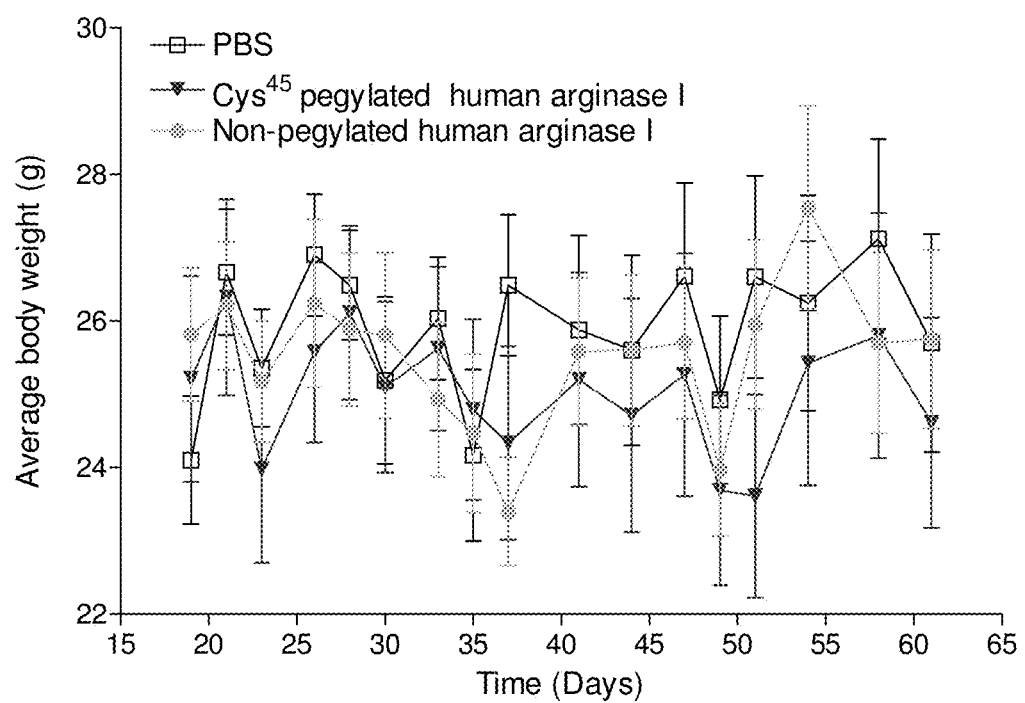
FIG. 11 shows the average body weights (±s.e.m.) of different treatment groups: (A) BALB/c nude mice xenografted with Hep3B human liver cancer cells injected with different drugs; (B) BALB/c nude mice xenografted with MCF-7 human breast cancer cells injected with $Cys^{161}$ pegylated *Bacillus caldovelox* arginase; (C) BALB/c nude mice xenografted with A549 lung cancer cells injected with different drugs; and (D) BALB/c nude mice xenografted with HCT-15 colorectal cancer cells injected with different drugs, during the course of the study.

As shown in FIG. 11A, the average body weights of the PBS control group, the $Cys^{45}$ pegylated human arginase I group, and the non-pegylated human arginase I group are 25.9±0.2 g, 25.0±0.2 g, and 25.5±0.2 g respectively, with no significant change throughout the experiment for each group.

Figure 12A:
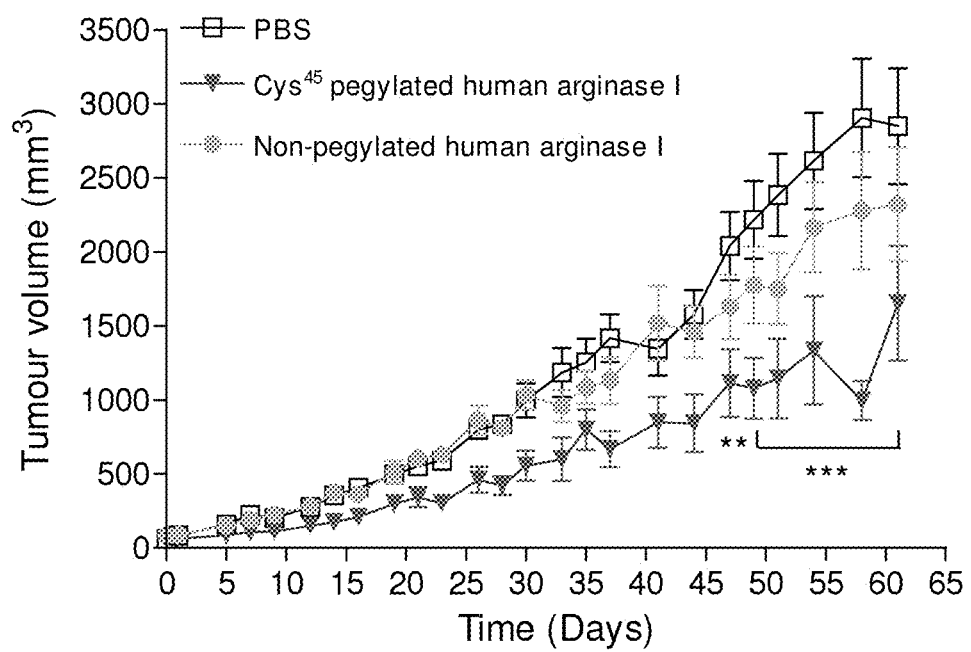
FIG. 12 shows (A) the in vivo activities (efficacies) of non-pegylated and $Cys^{45}$ pegylated human arginase I (HAI-PEG20) in BALB/c nude mice implanted with Hep3B human liver tumor cells subcutaneously, in terms of the tumor volume over the time course; (B) the in vivo activities of $Cys^{161}$ pegylated *Bacillus caldovelox* arginase (BCA-PEG20) in BALB/c nude mice xenografted with MCF-7 human breast cancer cells subcutaneously, in terms of the number of fold increase in the tumor volume over the time course; (C) the in vivo efficacies of $Cys^{161}$ pegylated *Bacillus caldovelox* arginase in BALB/c nude mice bearing A549 lung cancer xenograft subcutaneously; (D) the in vivo efficacies of $Cys^{161}$ pegylated *Bacillus caldovelox* arginase in BALB/c nude mice bearing A549 lung cancer xenograft subcutaneously (data are expressed as mean number of fold increase in tumor volume±s.e.m); (E) the in vivo efficacies of $Cys^{161}$ pegylated *Bacillus caldovelox* arginase in BALB/c nude mice bearing HCT-15 colorectal cancer xenograft subcutaneously; and (F) the in vivo efficacies of $Cys^{161}$ pegylated *Bacillus caldovelox* arginase in BALB/c nude mice bearing HCT-15 colorectal cancer xenograft subcutaneously (data are expressed as mean number of fold increase in tumor volume±s.e.m.).

In terms of the tumor volume, $Cys^{45}$ pegylated human arginase I (HAI-PEG20) significantly reduces the rate of tumor growth starting from Day 47 compared to the PBS control group (p<0.01); while non-pegylated human arginase I (HAI) does not show any significant effect (p>0.05) (FIG. 12A).

In Vivo Anti-Tumor Efficacy on Breast Cancer

In vivo anti-tumor efficacy of $Cys^{161}$ pegylated *Bacillus caldovelox* arginase (BCA-PEG20) on breast cancer is determined next.

Athymic nude BALB/c mice (age of 6-8 weeks) are housed under sterile conditions with 12 hour light-dark cycle and provided with autoclaved feed ad libitum. The mice are acclimated for at least 1 week before the start of experiments. Each nude mouse is injected with $1\times10^6$ MCF-7 human breast cancer cells to the right axilla subcutaneously. When palpable tumors of 5 mm diameter are found, the mice are randomly separated into two different groups (Table 4). Drugs or control vehicle (PBS) are injected intraperitoneally once per week starting from Day 0 for 18 days. Tumor dimensions (L: longest diameter and W: its perpendicular diameter) and body weights are measured on every Mondays, Wednesdays and Fridays with Vernier caliper. Tumor volume is calculated with the formula ($\frac{1}{2}\times L\times W^2$) and number of fold increase in tumor volume is calculated with reference to Day 0. The results are plotted against time. At Day 18 or when tumor diameter reaches 2.5 cm, the mice are euthanized and the final tumor and body weight are recorded.

TABLE 4

In vivo anti-tumor activity protocol

| Group | Testing drug | Units/mouse | route | Mice |
|---|---|---|---|---|
| 1 | PBS (control) | N/A | i.p. | 4M 4F |
| 2 | $Cys^{161}$-pegylated *Bacillus caldovelox* arginase | 250 | i.p. | 4M 4F |

Figure 11B:
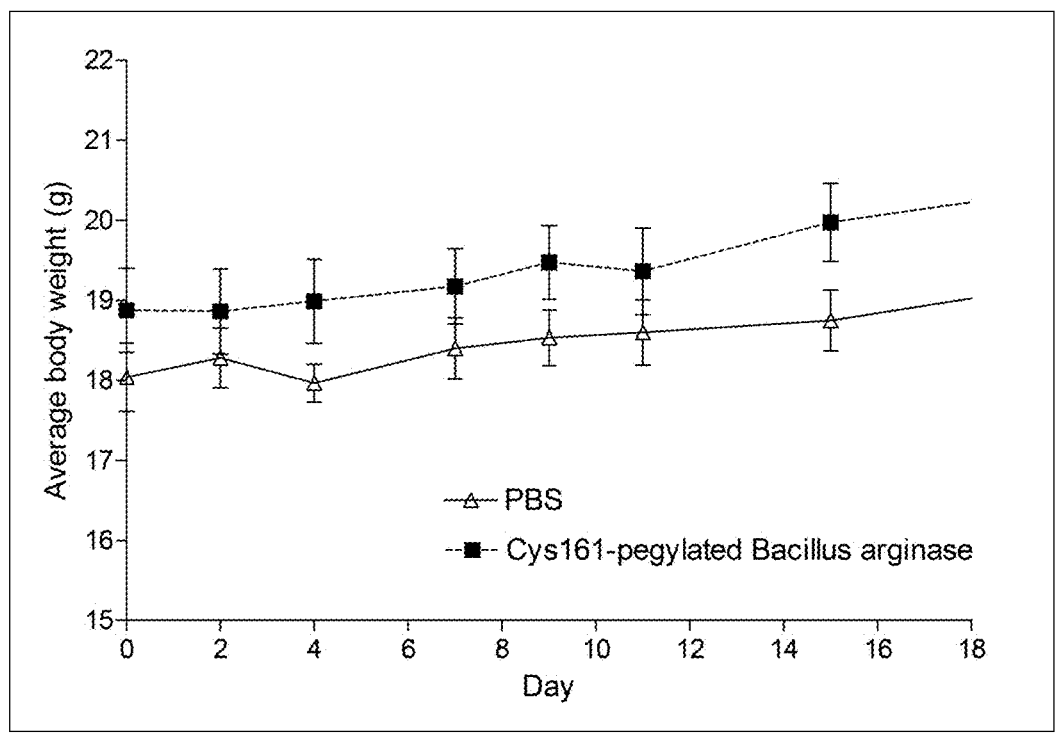
Figure 12B:
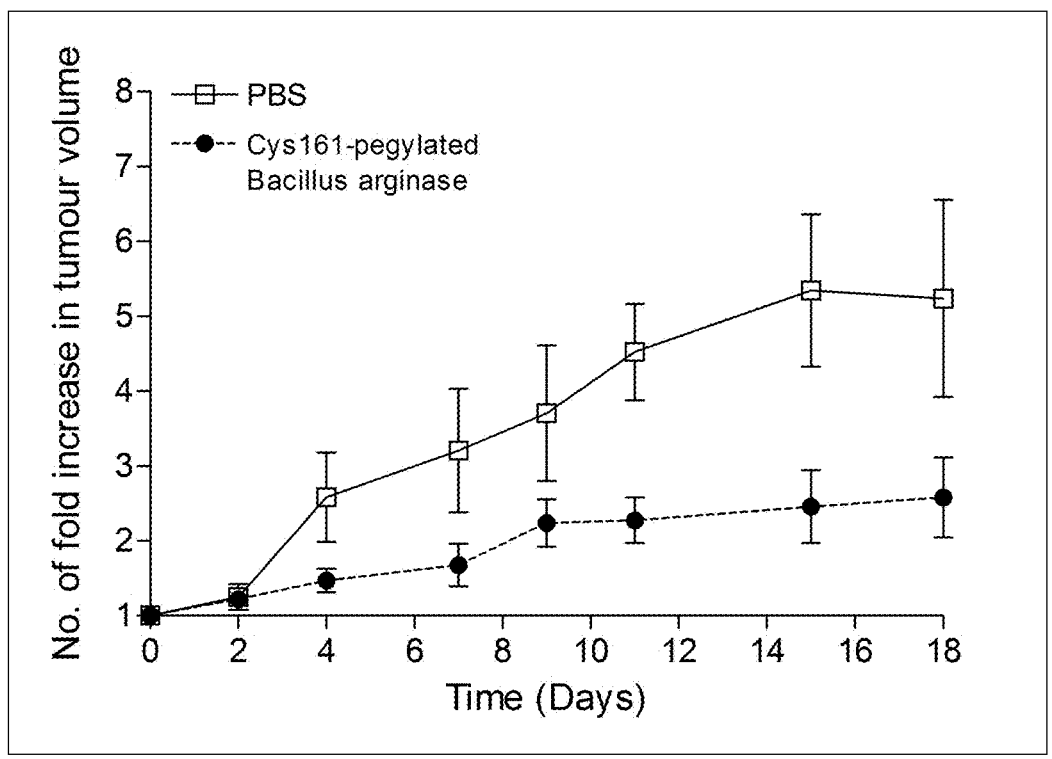

As shown in FIG. 11B, no significant difference in average body weights of the control group (18.76±0.50) and $Cys^{161}$-pegylated *Bacillus caldovelox* arginase (19.76±0.66) is observed throughout the experiment. $Cys^{161}$-pegylated *Bacillus caldovelox* arginase significantly suppresses tumor growth and reduces the number of fold increase in tumor volume in comparison to the PBS control group (2-way ANOVA: p<0.0001, FIG. 12B). Using Bonferroni post-test, the reduction is statistically significant starting from Day 15 (p<0.01) where the reduction is over 2.8 folds.

In Vivo Anti-Tumor Efficacy on Lung Cancer

Athymic nude BALB/c mice (age of 6-8 weeks) are housed under sterile conditions with 12 hour light-dark cycle and provided with autoclaved feed ad libitum. The mice are acclimated for at least 1 week before the start of experiments. Each nude mouse is injected with $5\times10^6$ A549 human lung cancer cells to the right axilla subcutaneously with matrigel growth supplement. When palpable tumors of about 5 mm diameter are found, the mice are randomly separated into three different groups (Table 5). Drugs or control vehicle (PBS) are injected intraperitoneally once per week starting from Day 0. Tumor dimensions (L: longest diameter and W: its perpendicular diameter) and body weights are measured on every Monday, Wednesday and Friday with Vernier caliper. Tumor volume is calculated with the formula ($\frac{1}{2}\times L\times W^2$) and number of fold increase in tumor volume (relative tumor volume) is calculated with reference to Day 0.

TABLE 5

In vivo anti-tumor activity protocol

| Group | Testing drug | Units/mouse | route | Mice |
|---|---|---|---|---|
| 1 | PBS (control) | N/A | i.p. | 5M 5F |
| 2 | Unpegylated *Bacillus caldovelox* arginase | 250 | i.p. | 5M 5F |
| 3 | $Cys^{161}$-pegylated *Bacillus caldovelox* arginase | 250 | i.p. | 5M 5F |

Figure 11C:
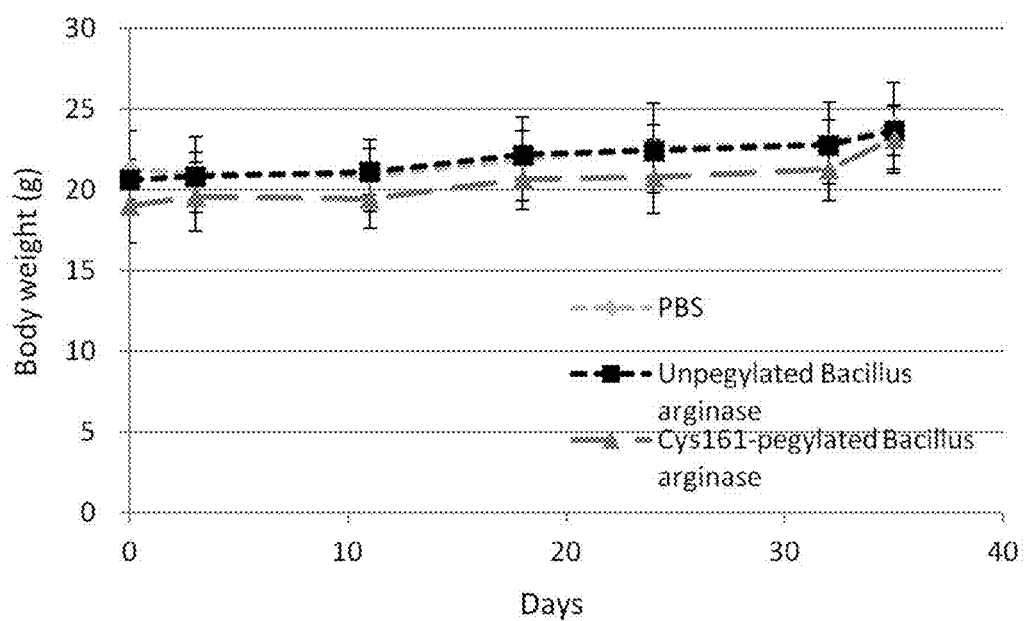

No significant difference in average body weights between different groups is observed throughout the experiment and last recorded as 23.98±2.68 g for the control group, 23.68±1.50 g for the unpegylated *Bacillus caldovelox* arginase and 23.16±2.08 g for the $Cys^{161}$-pegylated *Bacillus caldovelox* arginase at the end of experiment (FIG. 11C).

Figure 12C:
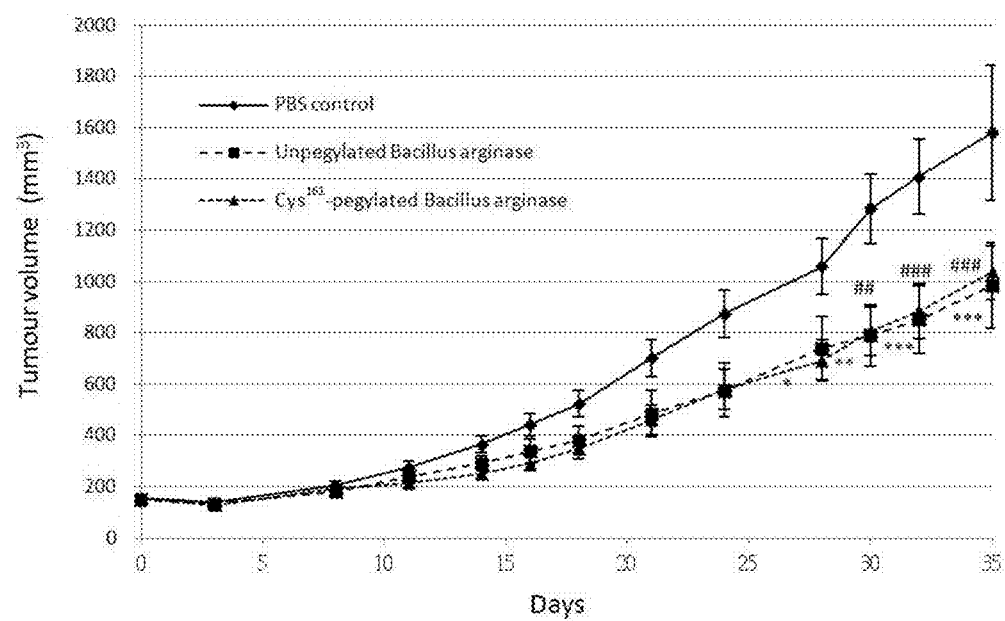
Figure 12D:
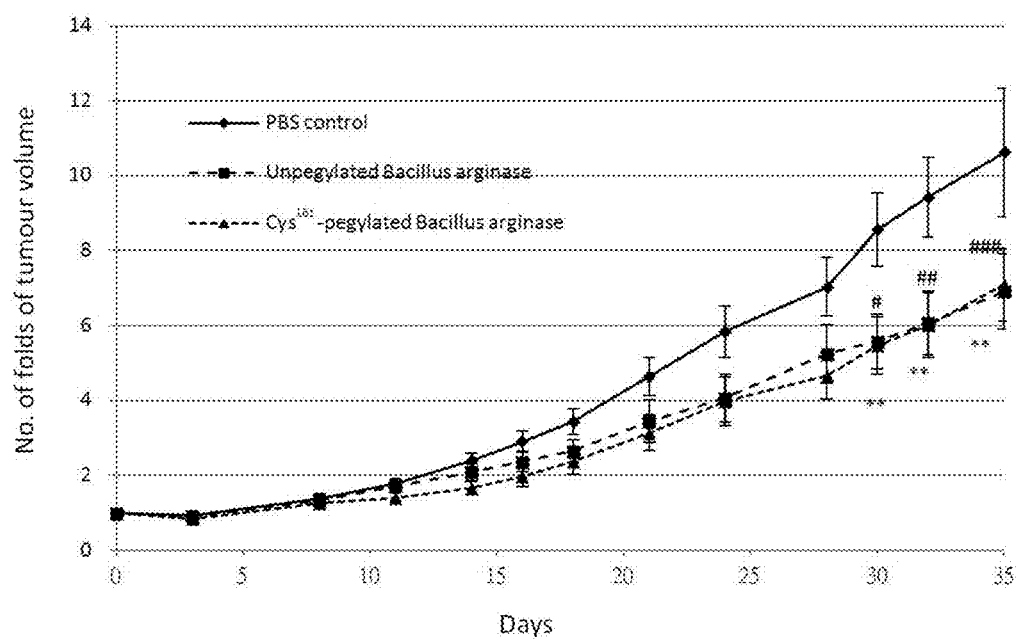

$Cys^{161}$-pegylated *Bacillus caldovelox* arginase (BCA-PEG20) however suppresses tumor growth significantly and statistically in comparison to vehicle control group in terms of progressive changes of tumor volume (FIG. 12C) and number of folds of tumor volume (FIG. 12D). Two-way ANOVA shows p values at <0.0001 for both parameters while Bonferroni post-test indicates the difference to start from Day 28 (p<0.05) to Day 35 (p<0.001) for tumor volume and from Day 30 to Day 35 (p<0.01 for all points) for relative tumor volume. The unpegylated *Bacillus caldovelox* arginase (BCA) at the same dose regime also shows anti-lung cancer effects in a similar extent with statistical significance for both parameters (two-way ANOVA, both with p<0.0001).

In Vivo Anti-Tumor Efficacy on Colorectal Cancer

In vivo anti-tumor efficacy of unpegylated (BCA) and Cys$^{161}$ pegylated *Bacillus caldovelox* arginase (BCA-PEG20) on colorectal cancer is determined as follows.

Athymic nude BALB/c mice (age of 6-8 weeks) are housed under sterile conditions with 12 hour light-dark cycle and provided with autoclaved feed and libitum. The mice are acclimated for at least 1 week before the start of experiments. Each nude mouse is implanted with about 3 mm$^3$ of in vivo maintained HCT-15 human colorectal cancer cells to the right axilla subcutaneously. When stable palpable tumors of about 5 mm diameter are found, the mice are randomly separated into five different groups (Table 6). Intraperitoneal administrations of arginase drugs or control vehicle (PBS) are given twice per week while 5-fluorouracil is given once per week starting from Day 0. Tumor dimensions (L: longest diameter and W: its perpendicular diameter) and body weights are measured on every Monday, Wednesday and Friday with Vernier caliper. Tumor volume is calculated with the formula ($\frac{1}{2} \times L \times W^2$) and number of fold increase in tumor volume (relative tumor volume) is calculated with reference to Day 0. The results are plotted against time. The mice are euthanized at the end of experiment or when tumor diameter reaches 2.5 cm.

TABLE 6

In vivo anti-tumor activity protocol

| Group | Testing drug | Units/mouse | route | Mice |
|---|---|---|---|---|
| 1 | PBS (control) | N/A | i.p. | 4M 4F |
| 2 | Unpegylated *Bacillus caldovelox* arginase | 500 | i.p. | 4M 3F |
| 3 | Cys$^{161}$-pegylated *Bacillus caldovelox* arginase | 250 | i.p. | 4M 3F |
| 4 | Cys$^{161}$-pegylated *Bacillus caldovelox* arginase + 5-Fluorouracil | 250 | i.p. | 4M 3F |
| 5 | 5-Fluorouracil | 10 mg/kg | i.p. | 2M 2F |

Figure 11D:
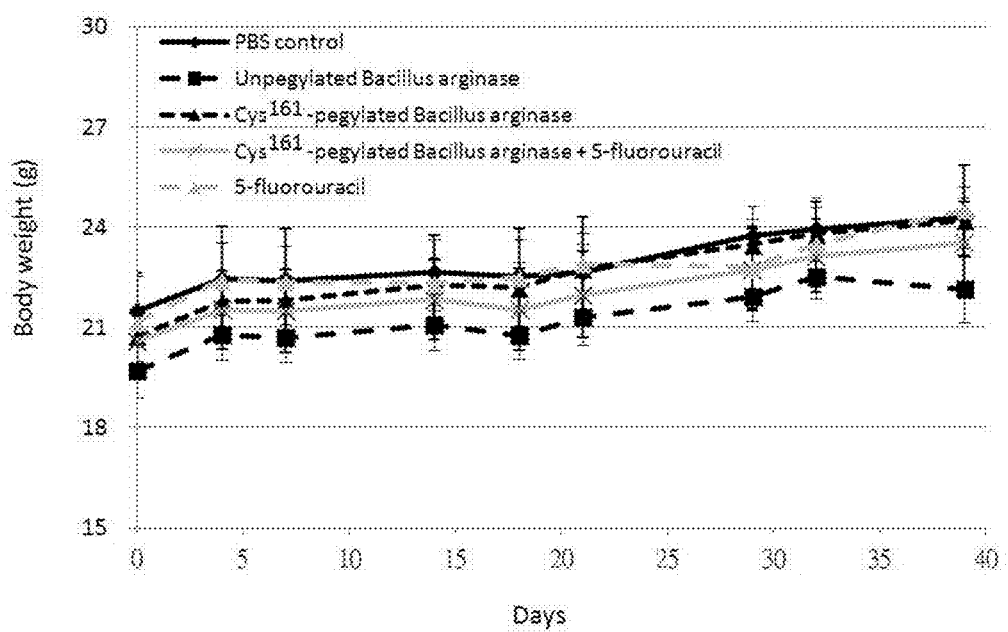

No significant difference in average body weights between different groups is observed throughout the experiment and last recorded as 24.3±0.9 g for the control group, 22.1±1.0 g for the unpegylated *Bacillus caldovelox* arginase group, 24.2±0.7 g for the Cys$^{161}$-pegylated *Bacillus caldovelox* arginase group, 23.5±1.2 g for the Cys$^{161}$-pegylated *Bacillus caldovelox* arginase+5-fluorouracil group and 24.5±1.4 g for the 5-fluorouracil group at the end of experiment (FIG. 11D).

Figure 12E:
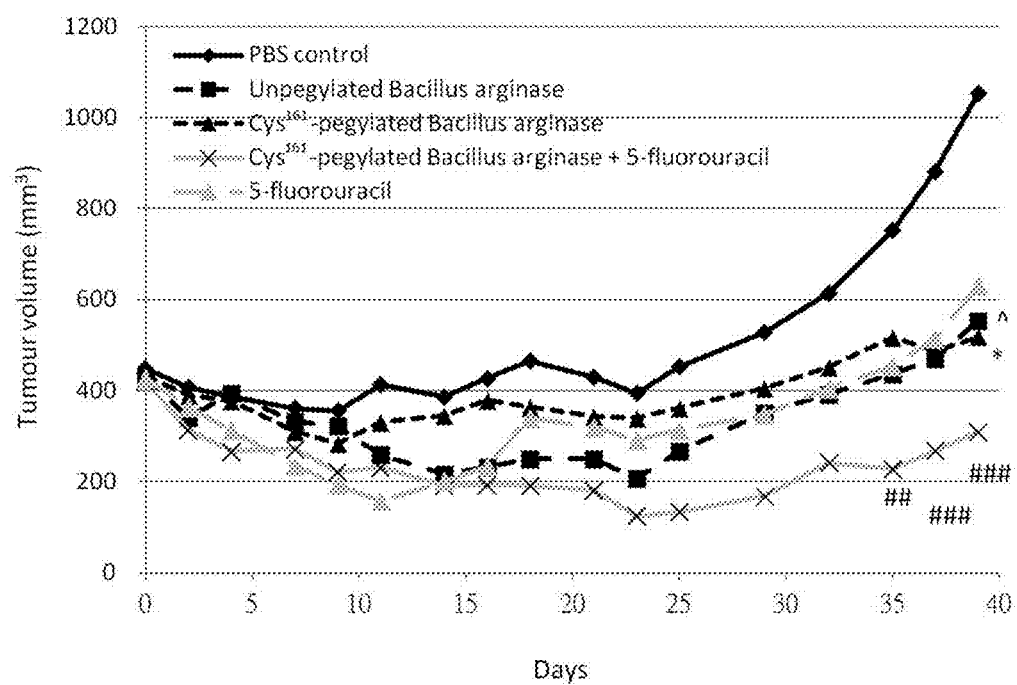
Figure 12F:
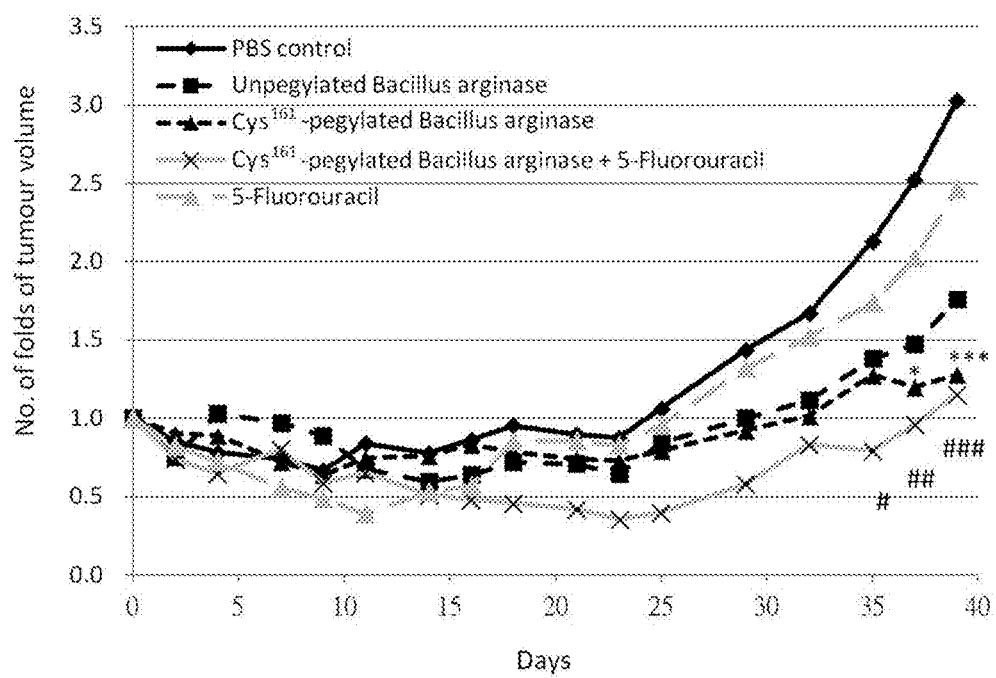

Both Cys$^{161}$-pegylated *Bacillus caldovelox* arginase (BCA-PEG20) and unpegylated *Bacillus caldovelox* arginase (BCA) in all three arginase drugs treated groups suppress tumor growth with statistical significance (FIG. 12E and FIG. 12F). For the drug combination group (Cys$^{161}$-pegylated *Bacillus caldovelox* arginase plus 5-fluorouracil), two-way ANOVA shows significance for number of folds of tumor volume and tumor volume with p<0.0001 in both cases. Bonferroni post-test further pinpoints the significant difference for number of folds of tumor volume to be from Day 36 to Day 40. For Cys$^{161}$-pegylated *Bacillus caldovelox* arginase alone group, two-way ANOVA shows significance for number of folds of tumor volume and tumor volume with p=0.0005 and p=0.0011, respectively. Bonferroni post-test indicates the difference to be from Day 38 to Day 40 for number of folds of tumor volume and on Day 40 for tumor volume. For unpegylated *Bacillus caldovelox* arginase group, the p values for number of folds of tumor volume and tumor volume are 0.0202 and <0.0001, respectively. The 5-fluorouracil group does not show significant tumor suppression in terms of number of folds of tumor volume (FIG. 12F). The drug combination group results in statistically significant lower tumor volume and number of folds of tumor volume than both the Cys$^{161}$-pegylated *Bacillus caldovelox* arginase alone group (p<0.0001 and p=0.0120, respectively) and the 5-fluorouracil alone group (p=0.0158 and p=0.0434, respectively). The results indicate a synergistic therapeutic effect for the Cys$^{161}$-pegylated *Bacillus caldovelox* arginase and 5-fluorouracil.

In Vivo Inhibitory Efficacy on Breast Cancer Metastasis $1 \times 10^5$ cells of a mouse metastatic breast cancer cell line (4T1) are injected orthotopically into the No. 4 inguinal mammary fat pad of wild-type BALB/c mice at the age of 6-8 weeks. When the tumors reach an average of 5 mm, the mice are divided into two different treatment groups (Table 7). BCA-PEG20 (250 U/mouse) or control vehicle (PBS) are injected intraperitoneally twice per week starting from Day 0. Body weight is measured every week. After three weeks, the mice are sacrificed and analyzed for the lung metastasis. The number of lung metastases are counted under a dissecting microscope after rinsing with PBS.

No significant difference in average body weight between different groups is observed throughout the experiment and last recorded as 21.8 g for control group and 21.5 g for the BCA-PEG20 group at the end of experiment.

Results demonstrate that BCA-PEG20 reduces the spontaneous lung tumor nodule formation compared with the PBS vehicle group. The spontaneous lung metastases are too numerous to count in PBS group but only 4 nodules on average are found in the BCA-PEG20 treatment group (Table 8). The result demonstrates that arginine depletion by BCA-PEG20 inhibits breast tumor metastasis.

TABLE 7

In vivo anti-metastasis protocol

| Group | Testing drug | Units/mouse | route | Mice |
|---|---|---|---|---|
| 1 | PBS (control) | N/A | i.p. | 1M |
| 2 | BCA-PEG20 | 250 | i.p. | 2M |

TABLE 8

| Group | Testing drug | Spontaneous lung metastases |
|---|---|---|
| 1 | PBS (control) | TNTC* |
| 2 | BCA-PEG20 | 4 |

*= Too numerous to count

Effect on HIV (HAI-PEG20)

The 50% inhibition concentration (IC$_{50}$) of the Cys$^{45}$ pegylated human arginase I (HAI-PEG20) on human immunodeficiency virus (HIV) is determined as a measurement of its effect on HIV.

The efficiency of an antiviral drug can be estimated using cell culture models for viral replication. The HIV replication assay utilizes H9 cells and HIV-1 strain RF. H9 cells, derived from human T lymphocytes, are highly susceptible to infection by CXCR4-using HIV-1 isolates, and show clear signs of cytopathic effects a few days post infection. HIV-1 strain RF is a CXCR4-using class B isolate that replicates to high levels in H9 cells.

H9 cells are seeded in four 96-well plates at $5 \times 10^4$ viable cells/mL and the cultures incubated at 37° C. The following day, two 96-well plates are inoculated with HIV-1 at 0.005 multiplicity of infection (50 μL per well).

Twenty-four hours after infection, the cells of one infected 96-well plate are treated with the Cys$^{45}$ pegylated human arginase I (HAI-PEG20) diluted to a final concentration of 1 U/mL, 10 U/mL and 50 U/mL in tissue culture medium (10% RPMI). Eight replicates are tested for each drug concentration and 100 µL is added per well.

Azido-thymidine (AZT) is used as a benchmark drug for this assay to ensure that a dose response is obtained. AZT is diluted appropriately (0.01, 0.1 and 1 µg/mL) in 10% RPMI and added to the second infected plate. Eight replicates are tested for each drug concentration and 100 µL is added per well.

A cytotoxicity control is set up in parallel: one 96-well plate of uninfected cells treated with three drug concentrations (1 U/mL, 10 U/mL and 50 U/mL; 8 replicates per drug concentration). This would allow the cytotoxic concentration to be determined ($CC_{50}$).

The remaining 96-well plate is inoculated with tissue culture medium alone to serve as the negative control.

Five days post infection plates are examined for cytopathic effect and the $IC_{50}$ of the drug is determined by comparing syncytial cell number in drug treated and non-treated cells.

Figure 13:
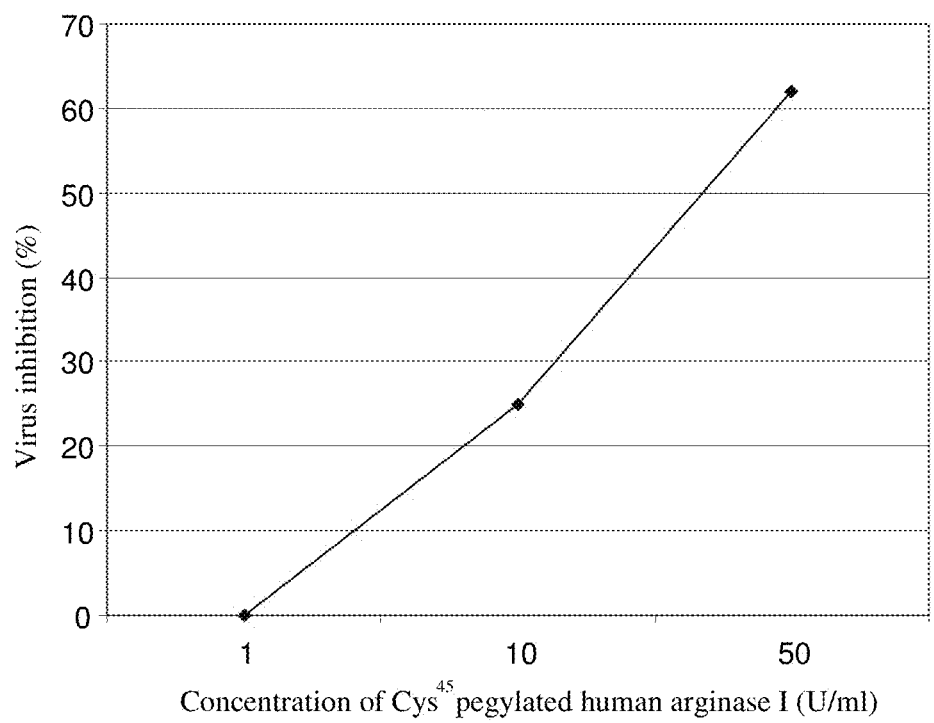
FIG. 13 shows an HIV inhibition assay for $Cys^{45}$ pegylated human arginase I (HAI-PEG20).

The results show that H9 cells inoculated with HIV strain RF have viral infection, whereas H9 cells inoculated with tissue culture medium alone remain healthy throughout the study. Cytopathic effect is observed in the H9 cultures infected with HIV and treated with the Cys$^{45}$ pegylated human arginase I (HAI-PEG20) at all concentrations. Eight out of eight (8/8) infected wells treated with the pegylated enzyme at a final concentration of 1 U/mL display cytopathic effect. For infected wells treated with the enzyme at a final concentration of 10 U/mL, six out of eight (6/8) wells display cytopathic effect. When the drug is tested at the highest final concentration of 50 U/mL, three out of eight (3/8) wells display cytopathic effect. These results are shown in Table 9 and FIG. 13. The $IC_{50}$ of the drug is found to be approximately 37 U/mL.

Figure 14:
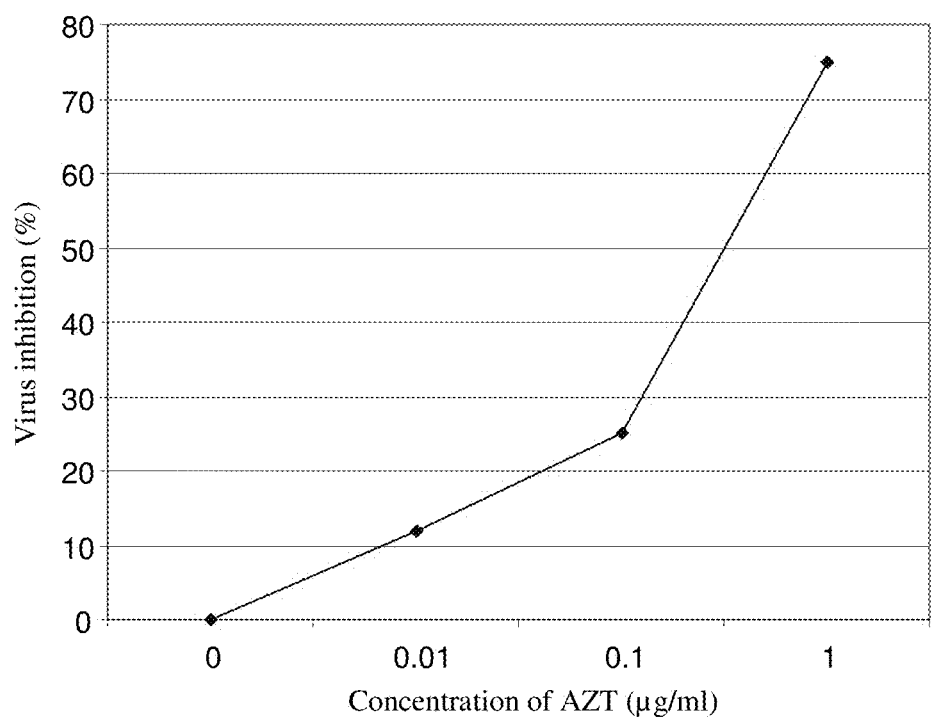
FIG. 14 shows the HIV inhibition assay for azido-thymidine (AZT).

When the benchmark drug AZT is added to infected wells at 0.01 µg/mL, seven out of eight (7/8) wells display cytopathic effect. For infected wells treated with AZT at 0.1 µg/mL, six out of eight (6/8) wells display cytopathic effect and when tested at 1 µg/mL, two out of eight (2/8) wells display cytopathic effect. These results are illustrated in FIG. 14. The $IC_{50}$ of the AZT is found to be 0.58 µg/mL.

TABLE 9

Virus inhibition assay

| Sample | Results |
| --- | --- |
| HIV without Cys$^{45}$ pegylated human arginase I treatment | 24/24 |
| HIV without Cys$^{45}$ pegylated human arginase I treatment (second plate) | 22/24 |
| HIV treated with Cys$^{45}$ pegylated human arginase I (50 U/mL) | 3/8 |
| HIV treated with Cys$^{45}$ pegylated human arginase I (10 U/mL) | 6/8 |
| HIV treated with Cys$^{45}$ pegylated human arginase I (1 U/mL) | 8/8 |
| HIV treated with AZT (0.01 µg/mL) | 7/8 |
| HIV treated with AZT (0.1 µg/mL) | 6/8 |
| HIV treated with AZT (1 µg/mL) | 2/8 |
| Negative control | 0/96 |
| Cytotoxicity control - uninfected cells treated with Cys$^{45}$ pegylated human arginase I (50 U/mL) | 8/8* |
| Cytotoxicity control - uninfected cells treated with Cys$^{45}$ pegylated human arginase I (10 U/mL) | 8/8* |
| Cytotoxicity control - uninfected cells treated with Cys$^{45}$ pegylated human arginase I (1 U/mL) | 8/8* |

Each well is inoculated with 50 µL of HIV at 0.005 multiplicity of infection.
*= cytotoxicity observed in each well, therefore viability counts performed for 1 well for each concentration. The results are recorded as a ratio; e.g. 1/X, where 1 is the number of positive wells/number of wells inoculated.

Figure 15:
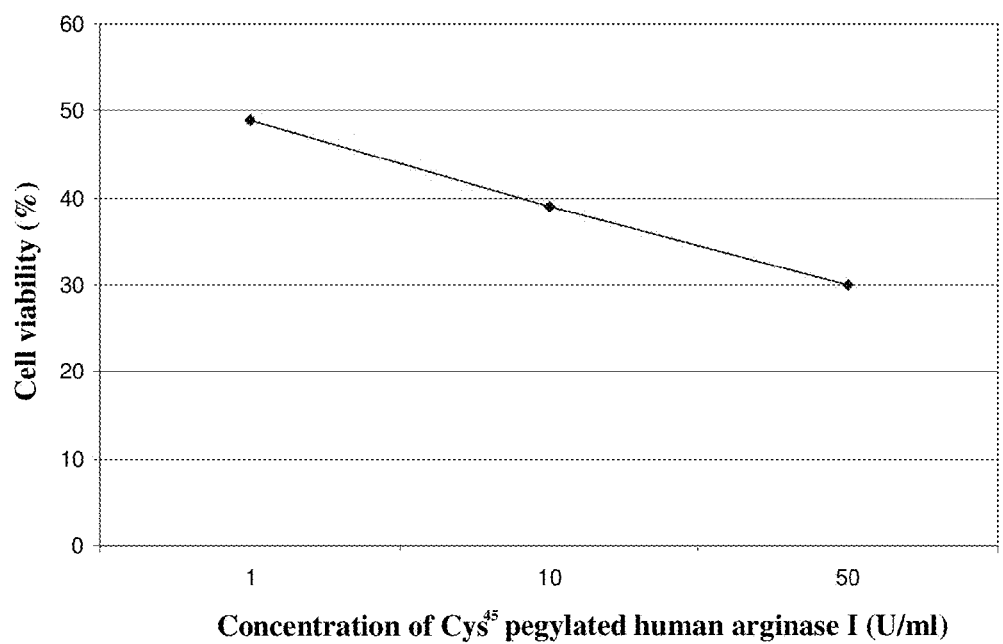
FIG. 15 shows the cytotoxicity of $Cys^{45}$ pegylated human arginase I (HAI-PEG20) in H9 cells inoculated with HIV strain RF.

Table 10 presents the viability counts for the cytotoxicity control. In the cytotoxicity test, all wells display symptoms of cytotoxicity, therefore viability counts are performed on one well for each concentration of Cys$^{45}$ pegylated human arginase I. The two highest concentrations, 50 U/mL and 10 U/mL, result in cell viabilities of 30% and 39%, respectively. For 1 U/mL, cell viability is 58%. Based on these results, cell viability is assessed for all 8 wells and the average is determined to be 48.9%. This approximates to a 50% reduction in cell viability based on the cell viability of cells (96.8%) when cells are seeded onto the 96 well plates. These results are displayed in Table 10 and FIG. 15, clearly demonstrating that HAI-PEG20 has inhibitory effects on HIV replication.

TABLE 10

Cell viability in cytotoxicity control

| Sample | | Live cells | Total cells | % viability | Average % viability |
| --- | --- | --- | --- | --- | --- |
| 50 U/mL - 1 well | | 9 | 30 | 30 | N/A |
| 10 U/mL - 1 well | | 11 | 28 | 39 | N/A |
| 1 U/mL | well 1 | 19 | 33 | 58 | |
| | well 2 | 30 | 63 | 48 | |
| | well 3 | 23 | 59 | 39 | 48.9 |
| | well 4 | 21 | 60 | 35 | |
| | well 5 | 33 | 58 | 57 | |
| | well 6 | 29 | 56 | 52 | |
| | well 7 | 31 | 49 | 63 | |
| | well 8 | 24 | 61 | 39 | |

N/A = not applicable

In Vitro Anti-Cancer Effects

In vitro cancer cell culture studies on the anti-cancer efficacies of different arginine-depleting enzymes are conducted for various cancer types.

Cell Proliferation Assay: For each cancer cell line, cells (5×10$^3$) in 100 µL culture medium are seeded to the wells of a 96-well plate and incubated for 24 hours by standard method. The culture medium is replaced with medium containing different concentrations of one of the arginases of the present invention or wild type human arginase before genetic modification (rhArg) or arginine deiminase (ADI). The plates are incubated for an additional 3 days at 37° C. in an atmosphere of 95% air/5% $CO_2$. The metabolically viable cell fraction is determined by the MTT assay, which is performed to estimate the number of viable cells in the culture. Non-linear regression with Prism 4.0 (Graphpad Software) is used to fit a sigmoidal dose response curve, and the amount of each of the arginine-degrading enzymes (in terms of U/mL or unit/ml or µg/mL) needed to achieve 50% inhibition of cell growth is defined as $IC_{50}$.

RT-PCR studies: Total RNA is extracted from cancer cell lines grown in culture using the Qiagen RNeasy kit. For reverse transcription-polymerase chain reaction (RT-PCR), the RNA is first reverse-transcribed into cDNA by iScript cDNA Synthesis kit (Bio-Rad, CA) according to the manufacturer's instruction. Briefly, 5 μg of total RNA is subjected to reverse transcription (RT) at 42° C. for 30 min. A 2 μL portion of cDNA is then amplified using 50 μL of reaction mixture containing 0.5 units of iTaq DNA polymerase (Bio-Rad, CA). PCR is performed in a DNA thermal MyCycler (Bio-Rad, CA). The following flanking primers are used:

(a) Human ASS (448 bp product):

```
Sense:       5'-GGGGTCCCTGTGAAGGTGACC-3';
Anti-sense:  5'-CGTTCATGCTCACCAGCTC-3'
```

(b) Human ASL (218 bp product):

```
Sense:       5'-CTCCTGATGACCCTCAAGGGA-3';
Anti-sense:  5'-CATCCCTTTGCGGACCAGGTA-3'
```

(c) Human OTC (221 bp product):

```
Sense:       5'-GATTTGGACACCCTGGCTAA-3';
Anti-sense:  5'-GGAGTAGCTGCCTGAAGGTG-3'
```

(d) Human GAPDH (306 bp product):

```
Sense:       5'-AGCCACATCGCTCAGACA-3';
Anti-sense:  5'-GCCCAATACGACCAAATCC-3'
```

The reaction products are subjected to 1% agarose gel electrophoresis. After electrophoresis and staining with ethidium bromide, all PCR product band intensities are analyzed by Lumi-Imager (Boehringer Mannheim, Ind.), and the relative mRNA expression levels are estimated by normalization with the house keeping gene GADPH.

As the results indicate, arginases and ADI are all efficient arginine-degrading enzymes. Unexpectedly, all the cancer cell lines tested in this example are found to be sensitive to the arginases of the present invention but many cancer cell lines are actually resistant to ADI treatment. It is discovered in the present invention that this difference is due to the fact that the arginases of the present invention convert arginine to ornithine and urea while ADI converts it to citrulline and ammonia. Citrulline can be recycled back to arginine if the cancer cells are argininosuccinate synthetase (ASS)-positive and argininosuccinate lyase (ASL)-positive, leading to drug resistance. Most strikingly, if the cancer cells are ornithine transcarbamylase (OTC)-negative, they cannot recycle ornithine back to arginine in the cells even if they are ASS-positive and ASL-positive. This guideline provided by the present invention has been found to be consistent with all our data as well as data from other research groups. Under this guideline, for instance, if the cancer cells are either ASS-negative or ASL-negative or both, they would be arginase-sensitive and ADI-sensitive. On the other hand, if the cancer cells are both ASS-positive and ASL-positive but OTC-negative, they would be arginase-sensitive and ADI-resistant. Therefore, it is believed that the arginases of the present invention have broader anti-cancer applications than ADI. Furthermore, ammonia (product from ADI reaction) is more toxic than urea (product from arginase reaction). Thus, the arginases of the present invention serving as anti-cancer agents are believed to be safer than ADI.

In vitro anti-cancer efficacy results are summarized in Tables 11A-11G. As indicated in Table 11A, all the melanoma cell lines tested are sensitive to arginase treatments. When the arginases of the present invention are added to culture medium, arginine is converted to ornithine and urea. All these cells are OTC-negative and according to the guideline discussed above, these cells cannot recycle the arginase reaction product, ornithine, back to arginine in the cells, and therefore the cells are inhibited due to the lack of arginine. According to the $IC_{50}$ values, all the arginases tested are very effective on the inhibition of cancer cell growth.

Although all the melanoma cell lines tested are all ASS-positive and ASL-positive, the expression levels of ASS are low, which can be confirmed by performing an ASS activity assay. The low ASS expression level explains why these cell lines are all sensitive to ADI treatments. B16 is a mouse melanoma cell line and it is also sensitive to both arginases and ADI. Thus, it is believed that ADI killing the melanoma cells is due to the low level of ASS expression while the arginases of the present invention kill the melanoma cells because they are OTC-negative.

In Table 11B, it is shown that all the leukemia cell lines tested are sensitive to arginase treatments. Some of these cancer cells tested are OTC-negative and according to the guideline discussed above, these cells cannot recycle the arginase reaction product, ornithine, back to arginine in the cells, and therefore the cells are inhibited due to the lack of arginine. According to the $IC_{50}$ values, all the arginases tested are very effective on inhibition of leukemia cancer cell growth. For ADI treatments, all the 4 leukemia cell lines tested are sensitive except the RPMI8226 cell line which is resistant to ADI treatment, which is most likely due to the fact that it is both ASS-positive and ASL-positive. Therefore, for inhibiting leukaemia cells, the arginases are advantageous over ADI.

Table 11C shows that all the colorectal cancer cell lines tested are sensitive to arginase treatments. All these cancer cells tested are OTC-negative. In consistent with the guideline discussed above, these cells cannot recycle the arginase reaction product, ornithine, back to arginine in the cells, and therefore the cells are inhibited due to the lack of arginine. According to the $IC_{50}$ values, all the arginases tested are very effective on the inhibition of colorectal cancer cell growth. For ADI treatments, only 2 colorectal cancer cell lines (WiDr and HT29) tested are sensitive and the other 2 (SW1116 and HCT15) are resistant to ADI treatment, which is most likely due to the fact that they are both ASS-positive and ASL-positive. For HT29, although it is ASS-positive and ASL-positive according to the RT-PCR data, the expression level of ASS is relatively low, as confirmed by performing an ASS activity assay, which explains why this cell line is sensitive to ADI treatment.

Also shown in Table 11C, most strikingly, all the pancreatic cancer cell lines tested are sensitive to the arginase treatments. All these cancer cells tested are OTC-negative. As discussed above, these cells cannot recycle the arginase reaction product, ornithine, back to arginine in the cells, and therefore the cells are inhibited due to the lack of arginine. According to the $IC_{50}$ values, all the arginases tested are very effective on the inhibition of pancreatic cancer cell growth. For ADI treatments, only one pancreatic cancer cell line (Panc1) tested is sensitive and the other 2 (BxPC3 and HPAFII) are resistant to ADI treatment. Clearly, for inhibiting pancreatic cancer cells, arginases are better than ADI.

Table 11D shows that all the gastric cancer cell lines tested are sensitive to arginase treatments. All these cancer cells tested are OTC-negative and thus, as discussed above, these cells cannot recycle the arginase reaction product, ornithine, back to arginine in the cells, and therefore the cells are inhibited due to the lack of arginine. As the $IC_{50}$ values indicate, all the arginases tested are very effective on the inhibition of gastric cancer cell growth. In a sharp contrast, all the gastric cancer cell lines tested are resistant to ADI treatment, which is most likely due to the fact that they are both ASS-positive and ASL-positive. This similar result is obtained for the liver cancer (or HCC) cell lines tested as shown in Table 11E.

Table 11E also shows that the retinoblastoma cancer cell line Y79 tested is sensitive to arginase treatments but resistant to ADI treatment, which is most likely due to the fact that they are both ASS-positive and ASL-positive.

Table 11F shows that the lung cancer cell line A549 tested is sensitive to arginase treatments. These cancer cells tested are OTC-negative. It is also sensitive to ADI treatment, which is most likely due to the fact that they are either ASS-negative or ASL-negative. In contrast, also shown in Table 11F, all the cervical cancer cell lines tested are sensitive to arginase treatments (they are all OTC-negative), but only 2 cervical cancer cell line (SiHa and C-33A) tested are sensitive and the other 3 (HeLa, ME180, CC3) are resistant to ADI treatment, which is most likely due to the fact that they are both ASS-positive and ASL-positive.

The results for breast cancer cells are shown in Table 11G. As it is shown, all the breast cancer cell lines tested are sensitive to arginase treatments (they are all OTC-negative). Strikingly, only one breast cancer cell line (MDA-MB-231) tested is sensitive and the other 3 (MCF-7, ZR-75-1, Hs578T) are resistant to ADI treatments.

Also shown in Table 11G are results for the prostate cancer cell lines, which are found to be sensitive to both arginase and ADI treatments. As discussed above, such results can be explained by the fact that the cell lines are both OTC-negative and ASS-negative.

TABLE 11A

| Type of cancer | Cell line name (medium, source) | BCA U/mL (µg/mL) | HAI U/mL (µg/mL) | rhArg U/mL (µg/mL) | ADI U/mL (µg/mL) | ARG | OTC | ASS | ASL |
|---|---|---|---|---|---|---|---|---|---|
| melanoma | SK-mel-2 (EMEM 10% FBS, 1% PS ATCC) | 0.612 (11.25) | 0.079 (0.80) | 0.0556 (1.31) | 0.0022 (0.082) | − | − | + | + L |
|  | SK-mel-24 (EMEM 10% FBS, 1% PS NCI) |  |  | 0.204 (4.82) | 0.012 (0.45) | − | − | + | + L |
|  | SK-mel-28 (EMEM 10% FBS, 1% PS ATCC) | 0.91 (16.72) | 0.064 (0.65) | 0.0523 (1.233) | 0.00084 (0.031) | − | − | + | + L |
|  | A375 (DMEM 10% FBS, 1% PS ATCC) | 0.15 (2.76) | 0.061 (0.62) | 0.0288 (0.679) | 0.00059 (0.022) | − | − | + | + L |
|  | B16 (DMEM 10% FBS, 1% PS ATCC) |  |  | 0.02 (0.48) | 0.004 (0.11) | − | − | + | + L |

TABLE 11B

| Type of cancer | Cell line name (medium, source) | BCA U/mL (µg/mL) | HAI U/mL (µg/mL) | rhArg U/mL (µg/mL) | ADI U/mL (µg/mL) | ARG | OTC | ASS | ASL |
|---|---|---|---|---|---|---|---|---|---|
| leukemia | HL60 (RPMI 10% FBS, 1% PS ATCC) |  |  | 0.03 (0.679) | 0.016 (0.591) | + | − | − | + |
|  | K562 (RPMI 20% FBS, 1% PS ATCC) |  |  | 0.06 (1.357) | 0.003 (0.085) | − | − | + | − |
|  | RPMI8226 (RPMI 10% FBS, 1% PS ATCC) |  |  | 0.09 (2.036) | R |  |  |  |  |
|  | Jurkat (RPMI 10% FBS, 1% PS ATCC) | 0.41 (7.54) |  | 0.037 (0.86) | 0.002 (0.074) |  |  |  |  |

TABLE 11C

| Type of cancer | Cell line name (medium, source) | BCA U/mL (μg/mL) | HAI U/mL (μg/mL) | rhArg U/mL (μg/mL) | ADI U/mL (μg/mL) | ARG | OTC | ASS | ASL |
|---|---|---|---|---|---|---|---|---|---|
| colorectal | (WiDr DMEM 10% FBS, 1% PS ATCC) | 0.215 (3.96) | 0.075 (0.76) | 0.038 (0.84) | 0.035 (0.9) | + | − | + | − |
| | SW1116 (RPMI 10% FBS, 1% PS ATCC) | 1.417 (20.98) | 0.41 (4.18) | 0.15 (3.394) | R | + | − | + | + |
| | HT29 (DMEM 10% FBS, 1% PS ATCC) | 0.231 (4.24) | | 0.03 (0.679) | 0.032 (0.83) | + | − | + L | + |
| | HCT15 (RPMI 10% FBS, 1% PS ATCC) | | 0.63 (6.44) | 0.083 (1.043) | R | + | − | + | + |
| pancreatic | Panc1 (DMEM 10% FBS, 1% PS ATCC) | 0.263 (4.84) | | 0.09 (2.036) | 0.049 (1.39) | − | − | + L | + |
| | BxPC3 (EMEM 10% FBS, 1% PS ATCC) | 0.846 (15.54) | | 0.08 (1.809) | R | + | − | + | + |
| | HPAFII (DMEM 10% FBS, 1% PS ATCC) | | | 0.86 (19.35) | R | − | − | + | + |

TABLE 11D

| Type of cancer | Cell line name (medium, source) | BCA U/mL (μg/mL) | HAI U/mL (μg/mL) | rhArg U/mL (μg/mL) | ADI U/mL (μg/mL) | ARG | OTC | ASS | ASL |
|---|---|---|---|---|---|---|---|---|---|
| gastric | AGS (RPMI 10% FBS, 1% PS ATCC) | 0.662 (12.17) | | 0.10 (2.262) | R | − | − | + | + |
| | MKN45 (RPMI 10% FBS, 1% PS Riken Cell bank, Japan) | 0.798 (14.67) | | 0.79 (17.873) | R | − | − | + | + |
| | BCG-823 (RPMI 10% FBS, 1% PS Beijing Institute of Cancer Research) | | | 0.11 (2.457) | R | − | − | + | + |

TABLE 11E

| Type of cancer | Cell line name (medium, source) | BCA U/mL (μg/mL) | HAI U/mL (μg/mL) | rhArg U/mL (μg/mL) | ADI U/mL (μg/mL) | ARG | OTC | ASS | ASL |
|---|---|---|---|---|---|---|---|---|---|
| HCC (liver cancer) | PLC/PRF/5 (DMEM 10% FBS, 1% PS ATCC) | 2.376 (43.67) | 0.94 (9.56) | 0.312 (7.07) | R | + | − | + | + |
| | Hep3B (DMEM 10% FBS, 1% PS ATCC) | 9.1 (57.68) | 0.29 (2.95) | 0.65 (15.0) | R | + | − | + | + |
| | HepG2 (DMEM 10% FBS, 1% PS ATCC) | 2.002 (36.79) | 0.097 (0.99) | 0.177 (4.00) | R | + | − | + | + |

TABLE 11E-continued

| Type of cancer | Cell line name (medium, source) | BCA U/mL (μg/mL) | HAI U/mL (μg/mL) | rhArg U/mL (μg/mL) | ADI U/mL (μg/mL) | ARG | OTC | ASS | ASL |
|---|---|---|---|---|---|---|---|---|---|
| | Huh7 (DMEM 10% FBS, 1% PS ATCC) | | | 1.59 (43) | R | + | − | + | + |
| | SK-HEP-1 (DMEM 10% FBS, 1% PS ATCC) | 12.27 (77.79) | 1.725 (6.05) | 0.15 (4) | 0.007 (0.2) | − | − | + L | + |
| retinoblastoma | Y79 (RPMI 10% FBS, 1% PS ATCC) | | | 0.5 (11.3) | R | − | − | + | + |

TABLE 11F

| Type of cancer | Cell line name (medium, source) | BCA U/mL (μg/mL) | HAI U/mL (μg/mL) | rhArg U/mL (μg/mL) | ADI U/mL (μg/mL) | ARG | OTC | ASS | ASL |
|---|---|---|---|---|---|---|---|---|---|
| lung | A549 (DMEM 10% FBS, 1% PS ATCC) | | 0.3294 (2.09) | 0.035 (0.44) | 0.011 (0.29) | − | − | − | + |
| Cervical | HeLa (DMEM 10% FBS, 1% PS ATCC) | 0.719 (13.21) | 0.366 (3.72) | 0.065 (0.82) | R | − | − | + | + |
| | ME180 (DMEM 10% FBS, 1% PS ATCC) | 1.42 (26.16) | 0.214 (2.18) | 0.153 (1.93) | R | − | − | + | + |
| | CC3 (DMEM 10% FBS, 1% PS ATCC) | 0.84 (15.50) | | 0.42 (5.29) | R | − | − | + | + |
| | SiHa (DMEM 10% FBS, 1% PS ATCC) | 0.32 (5.84) | 0.024 (0.24) | 0.03 (0.38) | 0.0025 (0.064) | − | − | − | + |
| | C-33A (DMEM 10% FBS, 1% PS ATCC) | 0.19 (3.55) | 0.033 (0.34) | 0.058 (0.72) | 0.0014 (0.036) | − | − | − | + |

TABLE 11G

| Type of cancer | Cell line name (medium, source) | BCA U/mL (μg/mL) | HAI U/mL (μg/mL) | rhArg U/mL (μg/mL) | ADI U/mL (μg/mL) | ARG | OTC | ASS | ASL |
|---|---|---|---|---|---|---|---|---|---|
| breast | MCF-7 (EMEM 10% FBS, 1% PS ATCC) | 0.05 (0.91) | | 0.28 (6.36) | R | − | − | + | + |
| | ZR-75-1 (DMEM 10% FBS, 1% PS ATCC) | | | 0.14 (3.18) | R | − | − | + | + |
| | Hs578T (DMEM 10% FBS, 1% PS, 10 μg/ml insulin NCI) | | | 3.75 (85.2) | | | − | + | + |
| | MDA-MB-231 (DMEM 10% FBS, 1% PS NCI) | 0.22 (4.11) | 0.273 | 0.44 (10.0) | 0.16 (5.93) | − | − | + L | + |
| | 4T1 | 0.68 | 0.058 | 0.023 (0.29) | 0.0007 (0.017) | | | | |
| Prostate | PC3 (DMEM 10% FBS, 1% PS ATCC) | 0.263 (4.84) | 0.40 (4.07) | 0.08 (1.47) | 0.0025 (0.064) | − | − | − | + |
| | LNCap (EMEM 10% FBS, 1% PS ATCC) | 2.119 (38.94) | 0.47 (4.78) | 0.41 (5.16) | 0.13 (3.34) | | | | |

For Table 11A to Table 11G, "+"=mRNA is detected by RT-PCR, indicating the corresponding gene is expressed; "−"=mRNA is not detected by RT-PCR, indicating the gene is not expressed; "R" indicates that the cell line is ADI-resistant and the $IC_{50}$ value cannot be estimated; and "L" indicates that the cell line has a relatively low level of ASS expression and therefore the cell line is still ADI-sensitive.

Figure 18:
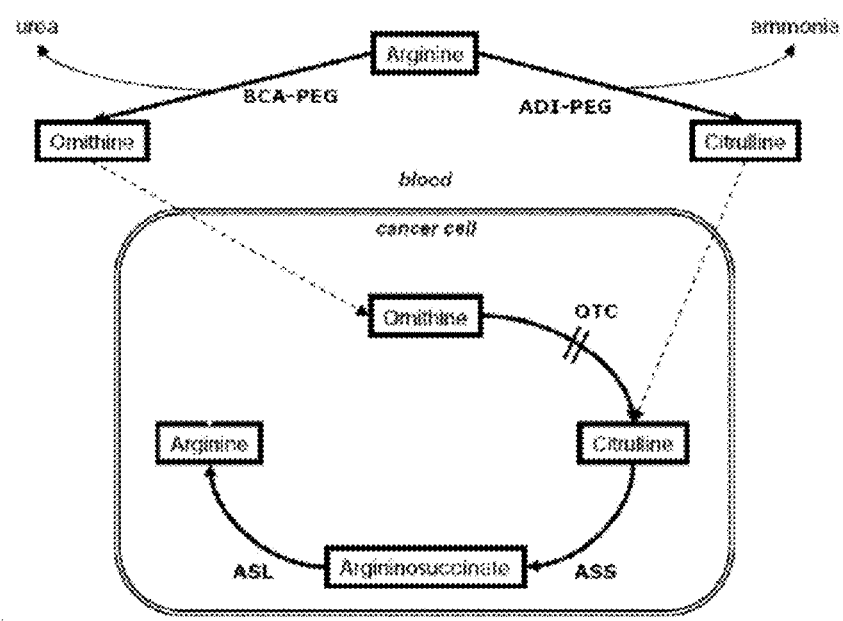
FIG. 18 illustrates a hypothesis and working model for cancer cells that are OTC-negative.

While not wish to be bound by the following hypothesis and working models, it is believed that the following hypothesis and working models are consistent with the experimental data of the present invention and thus are useful guides for further utilization of the inventions disclosed herewith (also see FIG. 18).

Hypothesis and working model explaining why OTC-negative cancer cells are arginase-sensitive but can be ADI-resistant. When arginase is added in the culture medium or pegylated arginase is injected in the blood (in the body), arginine is converted into ornithine and urea by the arginase enzymatic reaction. Ornithine formed then passes into the cancer cells. Unlike normal cells, cancer cells grow rapidly and require much more arginine than normal cells for protein synthesis and other cellular processes. If the cancer cells are OTC-positive, ASS-positive and ASL-positive, ornithine can be recycled back into arginine. Therefore, cancer cells still have arginine and they are not arginine-deficient and cancer growth is not inhibited. On the other hand, cancer cells that are OTC-negative or ASS-negative or ASL-negative or any combination of these deficiencies or low expression level of any of these genes, the synthesis (or recycle) pathway from ornithine to arginine is blocked and therefore cancer cells are lack of arginine and cancer cell growth is thus inhibited and cancer cell death may occur.

Hypothesis and working model for liver cancer cells that are OTC-negative are also provided. The model relates to urea cycle gene expression and resistance towards pegylated arginine deiminase (ADI-PEG) and pegylated *Bacillus caldovelox* arginase (BCA-PEG20). Liver cancer cells express the urea cycle enzymes argininosuccinate synthetase (ASS), argininosuccinate lyase (ASL) and arginase (ARG), but lack ornithine transcarbamylase (OTC). BCA-PEG20 in the bloodstream depletes arginine and produces ornithine, which enters the cell but fails to be recycled via the urea cycle owing to the absence of OTC. ADI-PEG converts arginine to citrulline, which can be readily converted back to arginine by ASS and ASL after uptake into liver cancer cells. Therefore, in this model, the liver cancer cells are sensitive to BCA-PEG20 treatment (inhibited by BCA-PEG20) but resistant to ADI-PEG treatment.

Hypothesis and working model for cancer cells that are OTC-negative are also provided. The model relates to gene expression in cancer cells and resistance towards pegylated arginine deiminase (ADI-PEG) and pegylated *Bacillus caldovelox* arginase (BCA-PEG20). For cancer cells that do not express arginase (ARG), cancer cells express the enzymes argininosuccinate synthetase (ASS), argininosuccinate lyase (ASL), but lack ornithine transcarbamylase (OTC). BCA-PEG20 in the bloodstream depletes arginine and produces ornithine, which enters the cell but fails to be recycled owing to the absence of OTC. ADI-PEG converts arginine to citrulline, which can be readily converted back to arginine by ASS and ASL after uptake into the cancer cells. Therefore, in this model, the cancer cells are sensitive to BCA-PEG20 treatment (inhibited by BCA-PEG20) but resistant to ADI-PEG treatment. This model can be applied to cancer cells in general.

Method of Further Enhancing Arginase Activity by Using Cobalt as Metal Cofactor

The native metal cofactor of arginase is manganese ($Mn^{2+}$). It is surprisingly discovered by the present invention that replacing the manganese with cobalt dramatically enhances the enzyme's activity. Either *Bacillus caldovelox* arginase (BCA) or the human arginase I (HAI) is expressed as described previously. The purification method is the same as described before except 10 mM of metal ion ($CoSO_4$ or $MnSO_4$) is added into the purified protein elution from Nickel affinity chromatography instead of added before Nickel affinity chromatography. Eluted factions containing the arginase enzyme are incubated with 10 mM metal for 15 mM at 50~55° C., followed by filtration through a 0.45 μm syringe filter. Then the solution is exchanged with storage buffer by ultrafiltration.

Figure 16:
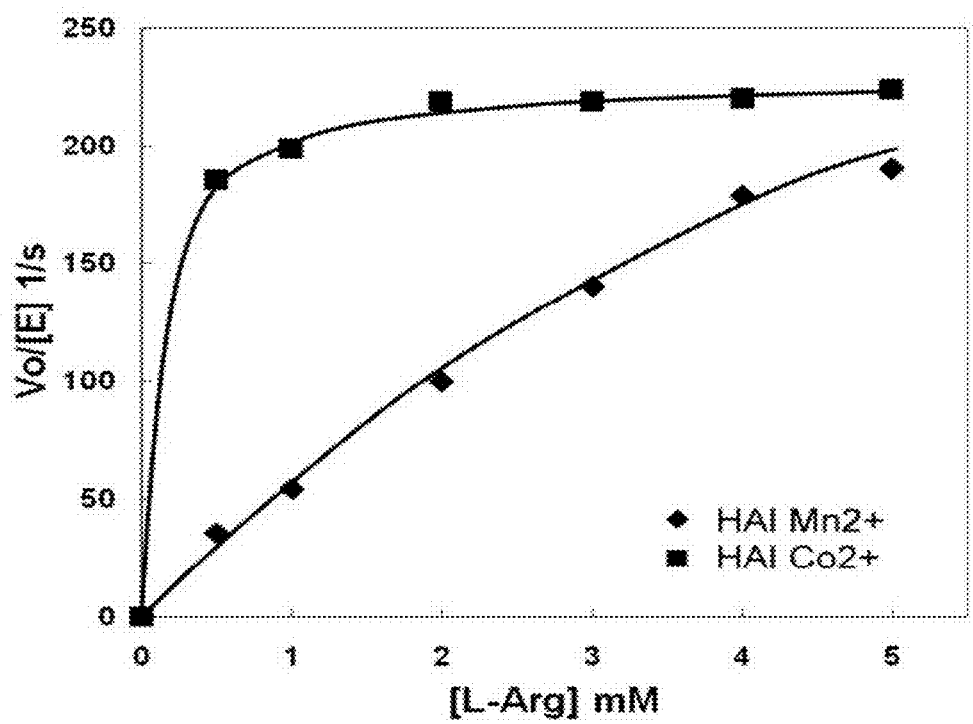
FIG. 16 shows a comparison of steady-state kinetics of human arginase I with different metal cofactors, i.e., $Mn^{2+}$ and $Co^{2+}$.

Diacetylmonoxine (DAMO) assay is used to determine the kinetic parameters of human arginase I with different metal cofactors. All enzymatic reactions are carried out at pH 7.4. The results are shown in FIG. 16. The steady-state kinetics of human arginase I (HAI) substituted with $Mn^{2+}$ or $Co^{2+}$ are measured in sodium phosphate buffer pH 7.4, 25° C. The $K_m$ of HAI with $Mn^{2+}$ (HAI $Mn^{2+}$) and HAI with $Co^{2+}$ (HAI $Co^{2+}$) are 1.83 mM and 0.19 mM respectively. Since the Km value is improved about 10-fold in HAI $Co^{2+}$, its specific activity is improved 10-fold and is a much more efficient drug to deplete arginine than HAI $Mn^{2+}$.

Enhancing Arginase Activity by Further Genetic Modification

To determine if modifying the amino acid residues around the active bind site of arginase would enhance its enzymatic activity, the amino acid residues at positions 15, 20, 102, 123, 127, 132, 133, 134, 137, 140, 141, 142, 143, 171, 174, 176, 177, 185, 224, 238, 240, 242 and 270 of $Cys^{161}$ *Bacillus caldovelox* arginase are further mutated and replaced with other amino acid residues as shown in Table 12. The mutants are cloned, their enzymatic activities are measured and compared with $Cys^{161}$ *Bacillus caldovelox* arginase. Among all mutants, only 9 of them show an increase in enzymatic activity when compared with BCA before modification, they are V20S, V20G, V20P, V127S, M141L, M141A, L171F, I185V and V238T (Table 13).

TABLE 12

| | Position | Original amino acid residue | Amino acid residues replaced |
|---|---|---|---|
| 1 | 15 | Q | K, N, M, I, T, R, S, Q, H, L, P, E, D, V, A, G |
| 2 | 20 | V | S, I, T, R, L, P, G, V, A |
| 3 | 102 | A | S, I, T, R, L, P, G, V, A, C, F |
| 4 | 123 | A | S, T, G, A |
| 5 | 127 | V | R, S, M, I, T, W, C, L, F, S, R, L, P |
| 6 | 132 | T | K, N, M, I, T, R, S, Q, H, L, P, R, E, D, V, A, G |
| 7 | 133 | S | T |
| 8 | 134 | P | S, I, T, G, V, A |
| 9 | 137 | N | Q |
| 10 | 140 | G | A |
| 11 | 141 | M | S, I, T, R, L, P, G, V, A |
| 12 | 142 | P | S, I, T, R, L, P, G, V, A, C, F |
| 13 | 143 | L | S, I, T, R, L, P, G, V, A, C, F |
| 14 | 171 | L | S, I, T, R, L, P, G, V, A, C, F |
| 15 | 174 | V | T, M, I, P, L, V |
| 16 | 176 | S | K, N, I, T, Q, H, L, P, E, D, V, A |
| 17 | 177 | L | T, I, P, L, A, V |
| 18 | 185 | I | D, V, A, Y, F, S, H, L, P |
| 19 | 224 | S | G, A, C, S |
| 20 | 238 | V | T, I, P, L, A, V |
| 21 | 240 | T | D, A, G, N, T, S, Y, C |
| 22 | 242 | V | S, I, T, R, L, P, G, V, A |
| 23 | 270 | V | S, I, T, R, L, P, G, V, A |

TABLE 13

| Clone | Enzymatic Activity |
|---|---|
| BCA before modification | ++ |
| V20S | ++++ |
| V20G | ++++ |
| V20P | +++++ |
| V127S | +++ |
| M141L | +++ |
| M141A | ++++ |
| L171F | +++ |
| I185V | +++ |
| V238T | +++ | mg/mL water-soluble MTT reagent is added to 100 μL culture medium and incubated at 37° C. for 4 hours. MTT is chemically reduced by cells into purple formazan, which is then dissolved by acidified SDS (0.01 N HCl in 10% SDS) in tissue culture medium. Concentration of the cleavage product formazan is then measured by reading its absorbance with a spectrophotometer with a 570 nm filter. Cell proliferation data are expressed as a percentage of control. Non-linear regression is used to fit a sigmoidal dose response curve with Prism 4.0 (Graphpad Software), and the amount of protein drug needed to achieve 50% cell growth inhibition is defined as $IC_{50}$. The results are shown in Table 14. The corresponding enzymatic activities are shown in Table 15.

TABLE 14

$IC_{50}$ of BCA and BCA mutant V20P in different kinds of cancer cells

| | | $IC_{50}$ Value | | | | Fold of Difference | |
|---|---|---|---|---|---|---|---|
| | | BCA | | BCA mutant V20P | | (BCA/BCA mutant V20P) | |
| | | (U/mL) | (mg/mL) | (U/mL) | (mg/mL) | (U/mL) | (mg/mL) |
| HCT-15 | Colon | 15.62 | 0.0916 | 7.34 | 0.0132 | 2.13 | 6.96 |
| Jurkat | Leukemia | 6.84 | 0.0401 | 0.90 | 0.0016 | 7.60 | 24.85 |
| MCF-7 | Breast | 5.51 | 0.0323 | 2.87 | 0.0051 | 1.92 | 6.28 |
| SK-MEL-28 | Melanoma | 3.35 | 0.0197 | 1.52 | 0.0027 | 2.20 | 7.21 |
| HEK293 | Kidney | 3.86 | 0.0226 | 3.40 | 0.0061 | 1.14 | 3.71 |
| A549 | Lung | 2.67 | 0.0157 | 1.64 | 0.0029 | 1.63 | 5.32 |
| Hep3B | Liver | 9.42 | 0.0552 | 9.43 | 0.0169 | 1.00 | 3.27 |
| Hela | Cervical | 2.83 | 0.0166 | 1.37 | 0.0025 | 2.07 | 6.75 |
| PANC-1 | Pancreatic | 1.20 | 0.0070 | 0.87 | 0.0016 | 1.38 | 4.51 |

Figure 17:
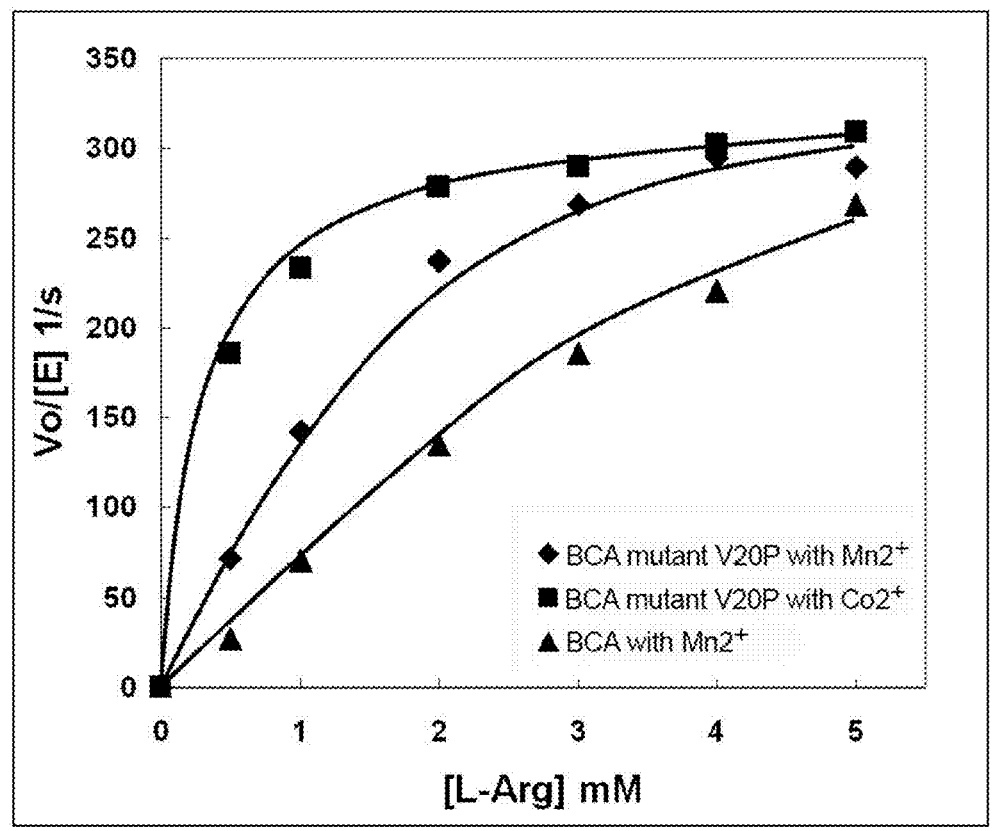
FIG. 17 shows a comparison of steady-state kinetics of the V20P mutant of $Cys^{161}$ *Bacillus caldovelox* arginase (BCA mutant V20P) and the $Cys^{161}$ *Bacillus caldovelox* arginase (BCA) substituted with $Mn^{2+}$ or $Co^{2+}$.

As shown in Table 13, it is surprisingly discovered by the present invention that the position 20 of BCA can be substituted with valine to improve enzyme activity, the mutated strain is referred to as "BCA mutant V20P". Steady-state kinetics of the BCA mutant V20P and BCA with $Mn^{2+}$ or $Co^{2+}$ are measured in sodium phosphate buffer pH 7.4, 25° C. and are shown in FIG. 17. The Km values of BCA mutant V20P with $Mn^{2+}$ and BCA mutant V20P with $Co^{2+}$ are about 1.29 mM and 0.18 mM respectively. The Km of BCA with $Mn^{2+}$ is about 3.2 mM. Therefore, the BCA mutant V20P with $Co^{2+}$ as cofactor (Km=0.18 mM) is a much more efficient drug to deplete arginine than the BCA with $Mn^{2+}$ (Km=3.2 mM).

In Vitro Cancer Cell Line Studies Using BCA Mutant V20P

Cell proliferation assay is conducted as follows.

$2.5 \times 10^3$ SK-MEL-28 (EMEM), $5 \times 10^3$ HEK293 (EMEM), MCF-7 (EMEM), HCT-15 (RPMI), Hep3B (DMEM), PANC-1 (DMEM), Hela (DMEM) and A549 (DMEM) cells are seeded to each well of a 96-well plate in 100 μL culture medium and are allowed to adhere to the plate overnight. On the next day, the culture medium is replaced with medium containing different concentrations of BCA and BCA mutant V20P protein drug. $2 \times 10^4$ Jurkat (RPMI) floating cells are seeded to each well of a 96-well plate in 50 μL culture medium at the day of adding protein drug and different concentrations of protein drug in 50 μL are added directly to each well. The cells are allowed to incubate for an additional 3 days at 37° C. in an atmosphere of 95% air/5% $CO_2$. MTT cell proliferation assay (Invitrogen) is then performed to estimate the number of viable cells in the culture. In brief, 10 μL of 5

TABLE 15

Specific activity of the proteins

| | Protein concentration (mg/mL) | Specific activity (U/mg) | Enzyme activity (U/mL) |
|---|---|---|---|
| BCA | 3.046 | 170.47 | 519.3 |
| BCA mutant V20P | 2.63 | 557.3 | 1465.7 |

Pegylation of BCA Mutant V20P

BCA mutant V20P is pegylated with a single chain mPEG-maleimide (20 kDa), referred to as "BCA-V20P-PEG20". The double bond of a maleimide undergoes an alkylation reaction with a sulfhydryl group to form a stable thioether bond. One gram of BCA mutant V20P is diafiltered into 0.02 M sodium phosphate, 0.5 M NaCl, pH 7.4, using Millipore Tangential Flow Filtration system (500 mL) with 10 K (cut-off) membrane (Millipore). The concentration of arginase is finally diluted to about 2 mg/mL. The reducing agent Tris(2-carboxyethyl)phosphine, TCEP, is added in a molar excess of 10 moles to one mole of arginase for reduction and the solution is gently stirred for 4 hours at room temperature. mPEG-Maleimide or mPEG-MAL (20 kDa) (Sunbright) in a molar excess of 20 moles to one mole of arginase is added to the reduced arginase and stirred for overnight at 4° C. The progress of site-directed pegylation is monitored by SDS-PAGE (FIG. 23). Under the above described conditions, the free sulfhydryl group of cysteine at position 161 on BCA mutant V20P is specifically linked via a stable thioether bond to the activated maleimide group of mPEG-MAL (20 kDa). Enzymatic activity of unpegylated BCA mutant V20P and $Cys^{161}$ pegylated BCA mutant V20P are measured and shown in Table 16.

TABLE 16

| | Specific activity (U/mg) |
|---|---|
| Unpegylated BCA mutant V20P | 566.58 |
| Cys$^{161}$ pegylated BCA mutant V20P | 499.41 |

The results show that BCA mutant V20P is much more efficient in killing various types of cancer cells in in vitro drug efficacy studies and can be pegylated without significant loss of activity While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A pharmaceutical composition for treating an arginine-dependent disease comprising a polyethylene glycol-arginase conjugate having a polyethylene glycol moiety covalently attached to a genetically-modified *Sus scrofa* arginase, wherein said genetically-modified *Sus scrofa* arginase has a single cysteine residue for covalently attaching to the polyethylene glycol moiety, wherein said single cysteine residue is located at a distance away from the active binding site of the genetically-modified *Sus scrofa* arginase such that the polyethylene glycol attachment does not interfere with the active site, wherein the polyethylene glycol moiety has a molecular weight of 10,000-30,000 Da,
   wherein the genetically-modified *Sus scrofa* arginase comprises all of SEQ ID No: 26 except for substitutions at positions 54, 119, 168 and 303 of SEQ ID NO: 26 and the single cysteine for the attachment of the polyethylene glycol moiety is at a position corresponding to position 45 of SEQ ID NO: 26.

2. The pharmaceutical composition of claim 1 further comprising a therapeutic agent for treating an arginine-dependent disease.

3. The pharmaceutical composition of claim 2 wherein the therapeutic agent is for treating cancer.

4. The pharmaceutical composition of claim 1 wherein the polyethylene glycol is a single chain or branched chain polyethylene glycol.

5. A method for treating an arginine-dependent disease comprising administering the pharmaceutical composition of claim 1 in combination with an anti-neoplastic compound to a subject in needs thereof, wherein said subject comprises human and other organisms.

* * * * *